(12) United States Patent
Palombella et al.

(10) Patent No.: US 6,818,427 B1
(45) Date of Patent: Nov. 16, 2004

(54) MEKK1 MOLECULES AND USES THEREOF

(75) Inventors: Vito J. Palombella, Needham, MA (US); Sha-Mei Liao, Lexington, MA (US)

(73) Assignee: Millennium Pharmaceuticals, Inc., Cambridge, MA (US)

( * ) Notice: Subject to any disclaimer, the term of this patent is extended or adjusted under 35 U.S.C. 154(b) by 340 days.

(21) Appl. No.: 09/697,898

(22) Filed: Oct. 27, 2000

(51) Int. Cl.$^7$ .......................... C12N 9/12; C12N 1/21; C12N 5/10; C12N 15/52; C07H 21/04

(52) U.S. Cl. ................. 435/194; 435/252.3; 435/320.1; 435/325; 536/23.2

(58) Field of Search .......................... 435/69.7, 252.3, 435/320.1, 325, 194; 536/23.2, 23.5, 23.4

(56) References Cited

U.S. PATENT DOCUMENTS 6,168,950 B1 * 1/2001 Monia et al. ............... 435/375

FOREIGN PATENT DOCUMENTS

WO    WO 97/35014    9/1997

OTHER PUBLICATIONS

Xia et al. (1998) Genes and Development, vol. 12, pp. 3369–3381.*
Angel P and Karin M, "The role of Jun, Fos and the AP–1 complex in cell–proliferation and transformation" Biochim Biophys Acta. 1991 1072(2–3): 129–57.
Arkin AP and Youvan DC, "An algorithm for protein engineering: simulations of recursive ensemble mutagenesis " Proc Natl Acad Sci U S A. 1992 89(16): 7811–5.
Blank JL et al., "Molecular cloning of mitogen–activated protein/ERK kinase kinases (MEKK) 2 and 3" J Biol Chem. 1996 271(10): 5361–8.
Cardone MH et al., "The regulation of anoikis: MEKK–1 activation requires cleavage by caspases" Cell. 1997 90(2): 315–23.
Deak JC and Templeton DJ, "Regulation of the activity of MEK kinase 1 (MEKK1) by autophosphorylation within the kinase activation domain" Biochem J. 1997 322: 185–92.
Delagrave S et al., "Recursive ensemble mutagenesis" Protein Eng. 1993 6(3): 327–31.
Gerwins P et al., "Cloning of a novel mitogen–activated protein kinase kinase kinase, MEKK4, that selectively regulats the c–Jun amino terminal kinase pathway" J Biol Chem. 1997 272(13): 8288–95.
Gottschalk LR et al., "Molecular regulation of the human IL–3 gene: inducible T cell–restricted expression requires intact AP–1 and Elf–1 nuclear protein binding sites" J Exp Med. 1993 178(5): 1681–92.
Ishizuka T et al., "Aggregation of the F∝RI on mast cells stimulates c–Jun amino–terminal kinase activity" J Biol Chem. 1996 271 (22): 12762–6.

Kaga S et al., "Activation of p21–CDC42/Rac–activated kinases by CD28 signaling: p21–activated kinase (PAK) and MEK kinase 1 (MEKK1) may mediate the interplay between CD3 and CD28 signals" J Immunol. 1998 160(9): 4182–9.
Lam KS "Application of combinatorial library methods in cancer reserach and drug discovery" Anticancer Drug Des. 1997 12(3): 145–67.
Lang–Carter CA and Johnson GL Ras–dependent growth factor regulation of MEK kinase in PC12 cells Science 1994 265(5177): 1458–61.
Lange–Carter CA et al., "A divergence in the MAP kinase regulatory network defined by MEK kinase and Raf" Science. 1993 260(5106):315–9.
Lee FS et al., "Activation of the IκBα alpha kinase complex by MEKK1, a kinase of the JNK pathway" Cell 197 88(2): 213–22.
McConnell HM et al., "The cytosensor microphysiometer: biological applications of silicon technology" Science 1992 257(5078): 1906–12.
Nolan GP, "NF–AT–AP–1 and Rel–bZIP: hybrid vigor and binding under the influence" Cell 1994 77(6): 795–8 Review.
Rao A, "NF–ATp: a transcription factor required for the co–ordinate induction of several cytokine genes" Immunol Today 1994 15(6): 274–81 Review.
Schlesinger TK et al., "The TAO of MEKK" Front Biosci. 1998 3:D1181–6 Review.
Siow YL et al., "Identification of two essential phosphorylated threonine residues in the catalytic domain of Mekk1" J Biol Chem. 1997 272(12): 7586–94.
Sonnhammer EL et al., "Pfam: a comprehensive database of protein domain families based on seed alignments" Proteins 1997 28(3): 405–20.
Suto MJ and Ransone LJ, "Novel approaches for the treatment of inflammatory diseases: inhibitors of NF–κB and AP–1" Curr. Pharm. Design 1997 3(5): 515–528.
Townsley FM et al., "Dominant–negative cyclin–selective ubiquitin carrier protein E2–C/UbcH10 blocks cells in metaphase" Proc Natl Acad Sci U S A. 1997 94(6): 2362–7.
Wang CY eta l., "Activation of the granulocyte–macrophage colony–stimulating factor promoter in T cells requires cooperative binding of Elf–1 and AP–1 transcription factors" Mol Cell Biol. 1994 14(2): 1153–9.

(List continued on next page.)

Primary Examiner—Elizabeth Slobodyansky
(74) Attorney, Agent, or Firm—Millennium Pharmaceuticals, Inc.

(57) ABSTRACT

The invention provides full-length, human isolated nucleic acids molecules, designated MEKK1 nucleic acid molecules, which encode a MEKK family member. The invention also provides antisense nucleic acid molecules, recombinant expression vectors containing MEKK1 nucleic acid molecules, host cells into which the expression vectors have been introduced, and nonhuman transgenic animals in which a MEKK1 gene has been introduced or disrupted. The invention still further provides isolated MEKK1 proteins, fusion proteins, antigenic peptides and anti-MEKK1 antibodies. Diagnostic methods utilizing compositions of the invention are also provided.

20 Claims, 8 Drawing Sheets

OTHER PUBLICATIONS

Wang XS et al., "Molecular cloning and characterization of a novel protein kinase with a catalytic domain homologous to mitogen–activated protein kinase kinase" J Biol Chem. 1996 271(49): 31607–11.

Wang XS et al., "MAPKKK6, a novel mitogen–activated protein kinase kinase kinase, that associates with MAPKKK5" Biochem Biophys Res Commun. 1998 253(1): 33–7.

Widmann C et al., "MEK kinase 1, a substrate for DEVD–directed caspases, is involved in genotoxin–induced apoptosis" Mol Cell Biol. 1998 18(4): 2416–29.

Winston BW et al., "Tumor necrosis factor alpha rapidly activates the mitogen–activated protein kinase (MAPK) cascade in a MAPK kinase kinase–dependent, c–Raf–1–independent fashion in mouse macrophages" Proc Natl Acad Sci U S A . 1995 92(5): 1614–8.

* cited by examiner

FIGURE 1

```
            M   A   A   A   A   G   N   R   A   S   S   S   G   F   P   G   A   R    18
     gagaaa ATG GCG GCG GCG GCG GGG AAT CGC GCC TCG TCG TCG GGA TTC CCG GGC GCC AGG    60

A   T   S   P   E   A   G   G   G   G   A   L   K   A   S   S   A   P   A    38
     GCT ACG AGC CCT GAG GCA GGC GGC GGA GGA GCC CTC AAG GCG AGC AGC GCG CCC GCG   120

A   A   A   G   L   L   R   E   A   G   S   G   G   R   E   R   A   D   W   R    58
     GCT GCC GCG GGA CTG CTG CGG GAG GCG GGC AGC GGG GGC CGC GAG CGG GCG GAC TGG CGG   180

R   R   Q   L   R   K   V   R   S   V   E   L   D   Q   L   P   E   Q   P   L    78
     CGG CGG CAG CTG CGC AAA GTG CGG AGT GTG GAG CTG GAC CAG CTG CCT GAG CAG CCG CTC   240

F   L   A   A   S   P   P   A   S   S   T   S   P   S   P   E   P   A   D   A    98
     TTC CTT GCC GCC TCA CCG CCG GCC TCC TCG ACT TCC CCG TCG CCG GAG CCC GCG GAC GCA   300

A   G   S   G   T   G   F   Q   P   V   A   V   P   P   P   H   G   A   A   S   118
     GCG GGG AGT GGG ACC GGC TTC CAG CCT GTG GCG GTG CCG CCG CCC CAC GGA GCC GCG AGC   360

R   G   G   A   H   L   T   E   S   V   A   A   P   D   S   G   A   S   S   P   138
     CGC GGC GGC GCC CAC CTT ACC GAG TCG GTG GCG GCG CCG GAC AGC GGC GCC TCG AGT CCC   420

A   A   A   E   P   G   E   K   R   A   P   A   A   E   P   S   P   A   A   A   158
     GCA GCG GCC GAG CCC GGG GAG AAG CGG GCG CCC GCC GCC GAG CCG TCT CCT GCA GCG GCC   480

P   A   G   R   E   M   E   N   K   E   T   L   K   G   L   H   K   M   D   D   178
     CCC GCC GGT CGT GAG ATG GAG AAT AAA GAA ACT CTC AAA GGG TTG CAC AAG ATG GAT GAT   540

R   P   E   E   R   M   I   R   E   K   L   K   A   T   C   M   P   A   W   K   198
     CGT CCA GAG GAA CGA ATG ATC AGG GAG AAA CTG AAG GCA ACC TGT ATG CCA GCC TGG AAG   600

H   E   W   L   E   R   R   N   R   R   G   P   V   V   V   K   P   I   P   V   218
     CAC GAA TGG TTG GAA AGG AGA AAT AGG CGA GGG CCT GTG GTG GTA AAA CCA ATC CCA GTT   660

K   G   D   G   S   E   M   N   H   L   A   A   E   S   P   G   E   V   Q   A   238
     AAA GGA GAT GGA TCT GAA ATG AAT CAC TTA GCA GCT GAG TCT CCA GGA GAG GTC CAG GCA   720

S   A   A   S   P   A   S   K   G   R   R   S   P   S   P   G   N   S   P   S   258
     AGT GCG GCT TCA CCA GCT TCC AAA GGC CGA CGC AGT CCT TCT CCT GGC AAC TCC CCA TCA   780

G   R   T   V   K   S   E   S   P   G   V   R   R   K   R   V   S   P   V   P   278
     GGT CGC ACA GTG AAA TCA GAA TCT CCA GGA GTA AGG AGA AAA AGA GTT TCC CCA GTG CCT   840

F   Q   S   G   R   I   T   P   P   R   R   A   P   S   P   D   G   F   S   P   298
     TTT CAG AGT GGC AGA ATC ACA CCA CCC CGA AGA GCC CCT TCA CCA GAT GGC TTC TCA CCA   900

Y   S   P   E   E   T   N   R   R   V   N   K   V   M   R   A   R   L   Y   L   318
     TAT AGC CCT GAG GAA ACA AAC CGC CGT GTT AAC AAA GTG ATG CGG GCC AGA CTG TAC TTA   960

L   Q   Q   I   G   P   N   S   F   L   I   G   D   S   P   D   N   K   Y   338
     CTG CAG CAG ATA GGG CCT AAC TCT TTC CTG ATT GGA GGA GAC AGC CCA GAC AAT AAA TAC  1020

R   V   F   I   G   P   Q   N   C   S   C   A   R   G   T   F   C   I   H   L   358
     CGG GTG TTT ATT GGG CCT CAG AAC TGC AGC TGT GCA CGT GGA ACA TTC TGT ATT CAT CTG  1080

L   F   V   M   L   R   V   F   Q   L   E   P   S   D   P   M   L   W   R   K   378
     CTA TTT GTG ATG CTC CGG GTG TTT CAA CTA GAA CCT TCA GAC CCA ATG TTA TGG AGA AAA  1140

T   L   K   N   F   E   V   E   S   L   F   Q   K   Y   H   S   R   S   S   398
     ACT TTA AAG AAT TTT GAG GTT GAG AGT TTG TTC CAG AAA TAT CAC AGT AGG CGT AGC TCA  1200

R   I   K   A   P   S   R   N   T   I   Q   K   F   V   S   R   M   S   N   S   418
     AGG ATC AAA GCT CCA TCT CGT AAC ACC ATC CAG AAG TTT GTT TCA CGC ATG TCA AAT TCT  1260

H   T   L   S   S   S   S   T   S   T   S   S   S   E   N   S   I   K   D   E   438
     CAT ACA TTG TCA TCA TCT AGT ACT TCT ACG TCT AGT TCA GAA AAC AGC ATA AAG GAT GAA  1320

E   E   Q   M   C   P   I   C   L   L   G   M   L   D   E   E   S   L   T   V   458
     GAG GAA CAG ATG TGT CCT ATT TGC TTG TTG GGC ATG CTT GAT GAA GAA AGT CTT ACA GTG  1380
```

FIGURE 1, cont'd

```
       C   E   D   G   C   R   N   K   L   H   H   H   C   M   S   I   W   A   E   E   478
      TGT GAA GAC GGC TGC AGG AAC AAG CTG CAC CAC CAC TGC ATG TCA ATT TGG GCA GAA GAG 1440

C   R   R   N   R   E   P   L   I   C   P   L   C   R   S   K   W   R   S   H   498
      TGT AGA AGA AAT AGA GAA CCT TTA ATA TGT CCC CTT TGT AGA TCT AAG TGG AGA TCT CAT 1500

D   F   Y   S   H   E   L   S   S   P   V   D   S   P   S   S   L   R   A   A   518
      GAT TTC TAC AGC CAC GAG TTG TCA AGT CCT GTG GAT TCC CCT TCT TCC CTC AGA GCT GCA 1560

Q   Q   Q   T   V   Q   Q   Q   P   L   A   G   S   R   R   N   Q   E   S   N   538
      CAG CAG CAA ACC GTA CAG CAG CAG CCT TTG GCT GGA TCA CGA AGG AAT CAA GAG AGC AAT 1620

F   N   L   T   H   Y   G   T   Q   Q   I   P   P   A   Y   K   D   L   A   E   558
      TTT AAC CTT ACT CAT TAT GGA ACT CAG CAA ATC CCT CCT GCT TAC AAA GAT TTA GCT GAG 1680

P   W   I   Q   V   F   G   M   E   L   V   G   C   L   F   S   R   N   W   N   578
      CCA TGG ATT CAG GTG TTT GGA ATG GAA CTC GTT GGC TGC TTA TTT TCT AGA AAC TGG AAT 1740

V   R   E   M   A   L   R   R   L   S   H   D   V   S   G   A   L   L   L   A   598
      GTG AGA GAG ATG GCC CTC AGG CGT CTT TCC CAT GAT GTC AGT GGG GCC CTG CTG TTG GCA 1800

N   G   E   S   T   G   N   S   G   G   S   S   G   S   S   P   S   G   G   A   618
      AAT GGG GAG AGC ACT GGA AAT TCT GGG GGC AGC AGT GGA AGC AGC CCG AGT GGG GGA GCC 1860

T   S   G   S   S   Q   T   S   I   S   G   D   V   V   E   A   C   C   S   V   638
      ACC AGT GGG TCT TCC CAG ACC AGT ATC TCA GGA GAT GTG GTG GAG GCA TGC TGC AGC GTT 1920

L   S   M   V   C   A   D   P   V   Y   K   V   Y   V   A   L   K   T   L       658
      CTG TCA ATG GTC TGT GCT GAC CCT GTC TAC AAA GTG TAC GTT GCT GCT TTA AAA ACA TTG 1980

R   A   M   L   V   Y   T   P   C   H   S   L   A   E   R   I   K   L   Q   R   678
      AGA GCC ATG CTG GTA TAT ACT CCT TGC CAC AGT TTA GCG GAA AGA ATC AAA CTT CAG AGA 2040

L   L   Q   P   V   V   D   T   I   L   V   K   C   A   D   A   N   S   R   T   698
      CTT CTC CAG CCA GTT GTA GAC ACC ATC CTA GTC AAA TGT GCA GAT GCC AAT AGC CGC ACA 2100

S   Q   L   S   I   S   T   L   L   E   L   C   K   G   Q   A   G   E   L   A   718
      AGT CAG CTG TCC ATA TCA ACA CTG TTG GAA CTG TGC AAA GGC CAA GCA GGA GAG TTG GCA 2160

V   G   R   E   I   L   K   A   G   S   I   G   I   G   G   V   D   Y   V   L   738
      GTT GGC AGA GAA ATA CTA AAA GCT GGA TCC ATT GGT ATT GGT GGT GTT GAT TAT GTC TTA 2220

N   C   I   L   G   N   Q   T   E   S   N   N   W   Q   E   L   L   G   R   L   758
      AAT TGT ATT CTT GGA AAC CAA ACT GAA TCA AAC AAT TGG CAA GAA CTT CTT GGC CGC CTT 2280

C   L   I   D   R   L   L   E   F   P   A   E   F   Y   P   H   I   V   S       778
      TGT CTT ATA GAT AGA CTG TTG TTG GAA TTT CCT GCT GAA TTT TAT CCT CAT ATT GTC AGT 2340

T   D   V   S   Q   A   E   P   V   E   I   R   Y   K   K   L   L   S   L   L   798
      ACT GAT GTT TCA CAA GCT GAG CCT GTT GAA ATC AGG TAT AAG AAG CTG CTG TCC CTC TTA 2400

T   F   A   L   Q   S   I   D   N   S   H   S   M   V   G   K   L   S   R   R   818
      ACC TTT GCT TTG CAG TCC ATT GAT AAT TCC CAC TCA ATG GTT GGC AAA CTT TCC AGA AGG 2460

I   Y   L   S   S   A   R   M   V   T   T   V   P   H   V   F   S   K   L   L   838
      ATC TAC TTG AGT TCT GCA AGA ATG GTT ACT ACA GTA CCC CAT GTG TTT TCA AAA CTG TTA 2520

E   M   L   S   V   S   S   T   H   F   T   R   M   R   R   R   L   M   A       858
      GAA ATG CTG AGT GTT TCC AGT TCC ACT CAC TTC ACC AGG ATG CGT CGC CGT TTG ATG GCT 2580

I   A   D   E   V   E   I   A   E   A   I   Q   L   G   V   E   D   T   L   D   878
      ATT GCA GAT GAG GTG GAA ATT GCC GAA GCC ATC CAG TTG GGC GTA GAA GAC ACT TTG GAT 2640

G   Q   Q   D   S   F   L   Q   A   S   V   P   N   N   Y   L   E   T   T   E   898
      GGT CAA CAG GAC AGC TTC TTG CAG GCA TCT GTT CCC AAC AAC TAT CTG GAA ACC ACA GAG 2700

N   S   S   P   E   C   T   V   H   L   E   K   T   G   K   G   L   C   A   T   918
      AAC AGT TCC CCT GAG TGC ACA GTC CAT TTA GAG AAA ACT GGA AAA GGA TTA TGT GCT ACA 2760
```

FIGURE 1, cont'd

```
  K   L   S   A   S   S   E   D   I   S   E   R   L   A   S   I   S   V   G   P    938
AAA TTG AGT GCC AGT TCA GAG GAC ATT TCT GAG AGA CTG GCC AGC ATT TCA GTA GGA CCT   2820

S   S   S   T   T   T   T   T   T   T   E   Q   P   K   P   M   V   Q   T        958
TCT AGT TCA ACA ACA ACA ACA ACA ACA ACA GAG CAA CCA AAG CCA ATG GTT CAA ACA       2880

K   G   R   P   H   S   Q   C   L   N   S   S   P   L   S   H   H   S   Q   L    978
AAA GGC AGA CCC CAC AGT CAG TGT TTG AAC TCC TCT CCT TTA TCT CAT CAT TCC CAA TTA   2940

M   F   P   A   L   S   T   P   S   S   S   T   P   S   V   P   A   G   T   A    998
ATG TTT CCA GCC TTG TCA ACC CCT TCT TCT TCT ACC CCA TCT GTA CCA GCT GGC ACT GCA   3000

T   D   V   S   K   H   R   L   Q   G   F   I   P   C   R   I   P   S   A   S   1018
ACA GAT GTC TCT AAG CAT AGA CTT CAG GGA TTC ATT CCC TGC AGA ATA CCT TCT GCA TCT   3060

P   Q   T   Q   R   K   F   S   L   Q   F   H   R   N   C   P   E   N   K   D   1038
CCT CAA ACA CAG CGC AAG TTT TCT CTA CAA TTC CAC AGA AAC TGT CCT GAA AAC AAA GAC   3120

S   D   K   L   S   P   V   F   T   Q   S   R   P   L   P   S   S   N   I   H   1058
TCA GAT AAA CTT TCC CCA GTC TTT ACT CAG TCA AGA CCC TTG CCC TCC AGT AAC ATA CAC   3180

R   P   K   P   S   R   P   T   P   G   N   T   S   K   Q   G   D   P   S   K   1078
AGG CCA AAG CCA TCT AGA CCT ACC CCA GGT AAT ACA AGT AAA CAG GGA GAT CCC TCA AAA   3240

N   S   M   T   L   D   L   N   S   S   S   K   C   D   D   S   F   G   C   S   1098
AAT AGC ATG ACA CTT GAT CTG AAC AGT AGT TCC AAA TGT GAT GAC AGC TTT GGC TGT AGC   3300

S   N   S   S   N   A   V   I   P   S   D   E   T   V   F   T   P   V   E   E   1118
AGC AAT AGT AGT AAT GCT GTT ATA CCC AGT GAC GAG ACA GTG TTC ACC CCA GTA GAG GAG   3360

K   C   R   L   D   V   N   T   E   L   N   S   S   I   E   D   L   L   E   A   1138
AAA TGC AGA TTA GAT GTC AAT ACA GAG CTC AAC TCC AGT ATT GAG GAC CTT CTT GAA GCA   3420

S   M   P   S   S   D   T   T   V   T   F   K   S   E   V   A   V   L   S   P   1158
TCT ATG CCT TCA AGT GAT ACA ACA GTA ACT TTT AAG TCA GAA GTT GCT GTC CTG TCT CCT   3480

E   K   A   E   N   D   D   T   Y   K   D   D   V   N   H   N   Q   K   C   K   1178
GAA AAG GCT GAA AAT GAT GAT ACC TAC AAA GAT GAT GTG AAT CAT AAT CAA AAG TGC AAA   3540

E   K   M   E   A   E   E   E   A   L   A   I   A   M   A   M   S   A   S       1198
GAG AAG ATG GAA GCT GAA GAA GAA GAA GCT TTA GCA ATT GCC ATG GCA ATG TCA GCG TCT   3600

Q   D   A   L   P   I   V   P   Q   L   Q   V   E   N   G   E   D   I   I   I   1218
CAG GAT GCC CTC CCC ATA GTT CCT CAG CTG CAG GTT GAA AAT GGA GAA GAT ATC ATC ATT   3660

I   Q   Q   D   T   P   E   T   L   P   G   H   T   K   A   K   Q   P   Y   R   1238
ATT CAA CAG GAT ACA CCA GAG ACT CTA CCA GGA CAT ACC AAA GCA AAA CAA CCG TAT AGA   3720

E   D   T   E   W   L   K   G   Q   Q   I   G   L   G   A   F   S   S   C   Y   1258
GAA GAC ACT GAA TGG CTG AAA GGT CAA CAG ATA GGC CTT GGA GCA TTT TCT TCT TGT TAT   3780

Q   A   Q   D   V   G   T   G   T   L   M   A   V   K   Q   V   T   Y   V   R   1278
CAG GCT CAA GAT GTG GGA ACT GGA ACT TTA ATG GCT GTT AAA CAG GTG ACT TAT GTC AGA   3840

N   T   S   S   E   Q   E   E   V   V   E   A   L   R   E   E   I   R   M   M   1298
AAC ACA TCT TCT GAG CAA GAA GAA GTA GTA GAA GCA CTA AGA GAA GAG ATA AGA ATG ATG   3900

S   H   L   N   H   P   N   I   I   R   M   L   G   A   T   C   E   K   S   N   1318
AGC CAT CTG AAT CAT CCA AAC ATC ATT AGG ATG TTG GGA GCC ACG TGT GAG AAG AGC AAT   3960

Y   N   L   F   I   E   W   M   A   G   G   S   V   A   H   L   L   S   K   Y   1338
TAC AAT CTC TTC ATT GAA TGG ATG GCA GGG GGA TCG GTG GCT CAT TTG CTG AGT AAA TAT   4020

G   A   F   K   E   S   V   V   I   N   Y   T   E   Q   L   L   R   G   L   S   1358
GGA GCC TTC AAA GAA TCA GTA GTT ATT AAC TAC ACT GAA CAG TTA CTC CGT GGC CTT TCG   4080

Y   L   H   E   N   Q   I   I   H   R   D   V   K   G   A   N   L   L   I   D   1378
TAT CTC CAT GAA AAC CAA ATC ATT CAC AGA GAT GTC AAA GGT GCC AAT TTG CTA ATT GAC   4140
```

FIGURE 1, cont'd

```
  S   T   G   Q   R   L   R   I   A   D   F   G   A   A   A   R   L   A   S   K   1398
AGC ACT GGT CAG AGA CTA AGA ATT GCA GAT TTT GGA GCT GCA GCC AGG TTG GCA TCA AAA 4200

G   T   G   A   G   E   F   Q   G   Q   L   L   G   T   I   A   F   M   A   P   1418
GGA ACT GGT GCA GGA GAG TTT CAG GGA CAA TTA CTG GGG ACA ATT GCA TTT ATG GCA CCT 4260

E   V   L   R   G   Q   Q   Y   G   R   S   C   D   V   W   S   V   G   C   A   1438
GAG GTA CTA AGA GGT CAA CAG TAT GGA AGG AGC TGT GAT GTA TGG AGT GTT GGC TGT GCT 4320

I   I   E   M   A   C   A   K   P   P   W   N   A   E   K   H   S   N   H   L   1458
ATT ATA GAA ATG GCT TGT GCA AAA CCA CCA TGG AAT GCA GAA AAA CAC TCC AAT CAT CTT 4380

A   L   I   F   K   I   A   S   A   T   T   A   P   S   I   P   S   H   L   S   1478
GCT TTG ATA TTT AAG ATT GCT AGT GCA ACT ACT GCT CCA TCG ATC CCT TCA CAT TTG TCT 4440

P   G   L   R   D   V   A   L   R   C   L   E   L   Q   P   Q   D   R   P   P   1498
CCT GGT TTA CGA GAT GTG GCT CTT CGT TGT TTA GAA CTT CAA CCT CAG GAC AGA CCT CCA 4500

S   R   E   L   L   K   H   P   V   F   R   T   T   W   *                       1512
TCA AGA GAG CTA CTG AAG CAT CCA GTC TTT CGT ACT ACA TGG TAG ccaattatgcagatcaa 4562 ctacagtagaaacaggatgctcaacaagagaaaaaaaacttgtggggaaccacattgatattctactggcca 4634
tgatgccactgaacagctatgaacgaggccagtggggaacccttacctaagtatgtgattgacaaatcatga 4706
tctgtacctaagctcagtatgcaaaagcccaaactagtgcagaaactgtaaactgtgcctttcaaagaactg 4778
gccctaggtgaacaggaaaacaatgaagtttgcatgactaaattgcagaagcataatttttttttttttggag 4850
cacttttcagcaatattagcggctgaggggctcaggatctatttaatatttcaattattcttccatttca 4922
tatagtgatcacaagcagggggttctgcaattccgttcaaattttttgtcactggctataaaatcagtatct 4994
gcctcttttaggtcagagtatgctatgagtagcaatacatacatatattttaaaagttgatacttctttat 5066
gacccacagttgacctttatttttcttaaataccagggcagttgtggctcattgtgcattttactgttggccc 5138
attcatttcgttttggaaattatggttttgtatttcatgtttatttacattcattttttgtttattcaggg 5210
aaagctgatctttttttttcaaaccaaaaaaaaaaa                                      5245
```

FIGURE 2

MEKK1 MOLECULES AND USES THEREOF

FIELD OF THE INVENTION

The invention relates to the identification of isolated, full-length human MEKK1 nucleic acid molecules encoding MEKK1 proteins, and methods of using the nucleic acid molecules and proteins.

BACKGROUND OF THE INVENTION

Controlling the state of phosphorylation is an important mechanism by which signaling molecules regulate the activity of other proteins. One common theme in such molecular signaling is the so-called kinase cascade, in which a linear series of kinases is activated by phosphorylation by upstream kinases. The mitogen-activated protein kinase (MAPK) pathway is one such example of a kinase cascade.

MAPKs are activated and phosphorylated by MAPK kinases (MKKs). The MKKs, in turn, are activated and phosphorylated by serine/threonine kinases (MKKKs), which themselves may be activated and phosphorylated by MKKK kinases (MKKKKs). There are currently over ten different groups of kinases covering more than twenty-two different genes that act upstream of one another and regulate the MKKs. One family, the MAPK/ERK kinase kinases (MEKKs) directly activate and phosphorylate specific MKKs. (Schlesinger et al., Front Biosci. 3:d1181–1186 (1998).)

MEKKs are activated by a number of diverse extracellular stimuli, indicating that not only can these molecules affect a wide variety of downstream activity, but they can also react to a diverse array of extracellular stimuli. For example, both EGF receptor stimulation and TNF a lead to an increase in MEKK1 activity. (Lange-Carter et al., Science 265:1458–1461 (1994); Winston et al., Proc. Natl. Acad. Sci., 92:1614–1618 (1995); Ishizuka et al., J. Biol. Chem. 271:12762–12766 (1996); Kaga et al., J. Immunol. 160:4182–4189 (1998).) MEKK1 is also activated in response to DNA damaging stresses such as UV irradiation, etoposide, cisplatin, and mitomycin C. (Widmann et al., Mol Cell. Biol. 18:2416–2429 (1998); Cardone et al., Cell 90:315–323 (1997).)

To date, six different MEKK genes have been at least partially cloned in mammalian cells. (Lange-Carter et al., Science 260:315–319 (1993); Blank et al., J. Biol. Chem. 271:5361–5368 (1996); Gerwins et al., J. Biol. Chem. 272:8288–8295 (1997); Wang et al., J. Biol. Chem 271:31607–31611 (1996); Wang et al., Biochem. Biophys. Res. Commun. 253:33–37 (1998).) There are a number of functional motifs found within the N-terminal regulatory domains of, at least, MEKK1 and MEKK4. Both molecules contain putative pleckstrin homology domains. Pleckstrin domains associate with polyphosphoinositides and mediate localization to specific regions of the plasma membrane. MEKK1 and MEKK4 also contain proline rich regions at the N-terminus, which may be of functional significance. Proline rich regions have been shown to be important for binding proteins that contain Src homology 3 (SH3) domains. Moreover, with regard to MEKK1, 14-3-3 proteins bind at the N-terminal regulatory domain. Although 14-3-3 association does not appear to dramatically affect MEKK activity, 14-3-3 proteins are important for MEKK regulation by mediating interactions with other regulatory proteins and for controlling subcellular localization of these kinases.

MEKK1 is important in regulating cell survival and apoptosis. MEKK1 is a substrate for caspases, a family of proteases required for apoptosis. The apoptotic signaling appears to be dependent on cleavage of MEKK1 and subsequent caspase activation, as cleavage resistant mutants do not induce apoptosis. Thus, MEKK1 plays a critical role in regulating cell survival and death, acting as a molecular switch when cleaved by caspases. Cleavage by a caspase changes MEKK1 from a survival promoting kinase to an effector of cell death.

MEKK1 activates both the Activator Protein-1 (AP-1) stress response pathway and the NFκB pathway. The transcription factor AP-1 is a critical regulator of T-cell activation, cytokine production, including IL-2, IL-3, and GM-CSF, and the production of metalloproteinases. (Gottschalf et al., J. Exp. Med. 178:1681 (1993); Want et al., J. Mol. Cell. Biol. 14:11153 (1994); Rao, Immunol. Today 15:274 (1994); Angel et al., Biochem. Biophys. Acta. 1072:129 (1991).) With regard to cytokine regulation, AP-1 mediates positive transactivation independently or in association with NF-AT (Nolan, Cell 77:795 (1994)). AP-1 activity is induced by many stimuli, including the phorbol ester tumor promoter 12-0-tetradecanoylphorbol-13-acetate (TPA), growth factors, cytokines, T-cell activators, neurotransmitters, and UV irradiation. AP-1 is composed of dimers of different members of the Fos and Jun family of proteins. AP-1 activity is regulated at the level of both C-Jun and C-Fos transcription and by post-translational modification of their protein products by phosphorylation and dephosphorylation.

Moreover, independent of its MAPK activity, MEKK1 also plays another role in regulating transcription factor NFκB, which is a dimer maintained in the cytoplasm via an inhibitory regulatory subunit, IκB. (Lee et al., Cell 88:213 (1997).) Upon stimulation with specific cytokines or environmental stresses, IκB is phosphorylated by IκB kinase which induces proteolytic degradation of IκB, thereby releasing NFκB to translocate to the nucleus effecting changes in transcription. (PCT Publication No. WO 97/35014.) Over expression of MEKK1 activates NFκB.

The two transcription factors, NFκB and AP1, have been shown to regulate the production of many proinflammatory cytokines and related proteins that are elevated in immunoinflammatory diseases. These transcription factors regulate IL-1, IL-2, TNF α, IL-6, and IL-8 levels in a variety of cell types. NFκB and other related transcription factor complexes are involved in the rapid induction of genes whose products function in protective and proliferative responses upon exposure of cells to external stimuli. Similarly, AP-1 has a significant role in the regulation of IL-2 transcription during T-cell activation. Thus, the role of NFκB and AP-1 is to act as a transducer of certain stimuli that lead to immune, inflammatory, and acute phase responses and, when overactivated, can lead to a disease state (Suto et al., Current Pharm. Design 3:515–528 (1997). No known antiinflammatory or autoimmune drugs have been specifically developed clinically as inhibitors of NFκB or AP-1. Therefore, a critical need exists for new therapies to treat immunoinflammatory and autoimmune disorders.

Prior to the instant invention, cloning efforts to obtain the full-length human MEKK1 gene have been unsuccessful for several reasons. Earlier efforts by others failed to identify the full-length cDNA. In some instances, the libraries that were screened were 5'-stressed and would not have expressed a full-length coding region. Specifically, the 5' region of the gene proved difficult to clone for reasons that were, until now, unclear. Other attempts using reverse PCR methodology were also unsuccessful.

Nevertheless, in order to completely understand MEKK1 biology and to develop potential regulators or modulators of MEKK1, the full-length MEKK1 nucleic acid molecule had to be cloned and isolated. There is a need, 9 therefore, to identify and clone the full-length MEKK1 nucleic acid to further understand and exploit the role of MEKK1.

SUMMARY OF THE INVENTION

The present invention is based, in part, on the discovery of a novel fill-length human gene referred to herein as "MEKK1". The polynucleotide sequence of a cDNA encoding a MEKK1 polypeptide is shown in SEQ ID NO:1, and the amino acid sequence of a MEKK1 polypeptide is shoen in SEQ ID NO:2. In addition, the polynucleotide sequence of the coding region is from nucleotide 7 to nucleotide 4545 of SEQ ID NO:1.

Accordingly, in a first aspect, the invention features a full-length nucleic acid molecule which encodes a MEKK1 protein or polypeptide, e.g., a biologically active portion of the MEKK1 protein. In a preferred embodiment the isolated nucleic acid molecule encodes a polypeptide having the amino acid sequence of SEQ ID NO:2. In other embodiments, the invention provides isolated MEKK1 nucleic acid molecules having the polynucleotide sequence shown in SEQ ID NO:1, or nucleotide 7 to nucleotide 4545 of SEQ ID NO:1, or the sequence of the DNA insert of the plasmid deposited with ATCC Accession Number PTA-1836. In still other embodiments, the invention provides nucleic acid molecules that are substantially identical (e.g., naturally occurring allelic variants) to the nucleotide sequence shown in SEQ ID NO:1, or nucleotide 7 to nucleotide 4545 of SEQ ID NO:1, or the sequence of the DNA insert of the plasmid deposited with ATCC Accession Number PTA-1836. In other embodiments, the invention provides a nucleic acid molecule which hybridizes under stringent hybridization conditions to a nucleic acid molecule comprising the polynucleotide sequence of SEQ ID NO:1 or the sequence of the DNA insert of the plasmid deposited with ATCC Accession Number PTA-1836, wherein the nucleic acid encodes a full-length MEKK1 protein or an active fragment thereof.

In a related embodiment of the first aspect, the invention further provides nucleic acid constructs which include a MEKK1 nucleic acid molecule described herein. In certain embodiments, the nucleic acid molecules of the invention are operatively linked to native or heterologous regulatory sequences. Also included are vectors and host cells containing the MEKK1 nucleic acid molecules of the invention, e.g., vectors and host cells suitable for producing MEKK1 nucleic acid molecules and polypeptides.

In another related embodiment of the first aspect, the invention provides nucleic acid fragments suitable as primers or hybridization probes for the detection of MEKK1-encoding nucleic acids.

In still another related embodiment of the first aspect, isolated nucleic acid molecules that are antisense to a MEKK1 encoding nucleic acid molecule are provided.

In a second aspect, the invention features MEKK1 polypeptides, and biologically active or antigenic fragments thereof, that are useful, e.g., as reagents or targets, in assays applicable to treatment and diagnosis of MEKK1 mediated or related disorders. In another embodiment, the invention provides MEKK1 polypeptides having a MEKK1 activity. Preferred polypeptides are MEKK1 proteins including at least one processed/cleaved domain, e.g., amino acid residues 876–1512 of SEQ ID NO:2, and/or one kinase or catalytic domain, e.g., amino acid residues 1191–1512 of SEQ ID NO:2, and, preferably, having a MEKK1 activity, e.g., a MEKK1 activity as described herein.

In another embodiment of the second aspect, the invention provides MEKK1 polypeptides, e.g., a MEKK1 polypeptide having the amino acid sequence shown in SEQ ID NO:2; the amino acid sequence encoded by the cDNA insert of the plasmid deposited with ATCC Accession Number PTA-1836; an amino acid sequence that is substantially identical to the amino acid sequence shown in SEQ ID NO:2; or an amino acid sequence encoded by a nucleic acid molecule having a polynucleotide sequence which hybridizes under stringent hybridization conditions to a nucleic acid molecule comprising the polynucleotide sequence of SEQ ID NO:1 or nucleotide 7 to nucleotide 4545 of SEQ ID NO:1, or the sequence of the DNA insert of the plasmid deposited with ATCC Accession Number PTA-1836, wherein the nucleic acid encodes a full length MEKK1 protein or an active fragment thereof.

In a related embodiment of the second aspect, the invention further provides nucleic acid constructs that include a MEKK1 nucleic acid molecule described herein.

In a related embodiment of the second aspect, the invention provides MEKK1 polypeptides or fragments operatively linked to non-MEKK1 polypeptides to form fusion proteins.

In a third aspect, the invention features antibodies and antigen-binding fragments thereof, that react with, or more preferably specifically bind MEKK1 polypeptides.

In a fourth aspect, the invention provides methods of screening for compounds that modulate the expression or activity of the MEKK1 polypeptides or nucleic acids.

In a fifth aspect, the invention provides a process for modulating MEKK1 polypeptide or nucleic acid expression or activity, e.g., using the aforementioned screened compounds. In certain embodiments, the methods involve treatment of conditions related to aberrant activity or expression of the MEKK1 polypeptides or nucleic acids, such as conditions involving aberrant or deficient cellular adhesion, proliferation or differentiation.

The invention also provides assays for determining the activity of, or the presence or absence of, MEKK1 polypeptides or nucleic acid molecules in a biological sample, including for disease diagnosis.

In a sixth aspect, the invention provides assays for determining the presence or absence of a genetic alteration in a MEKK1 polypeptide or nucleic acid molecule, including for disease diagnosis.

It is to be understood from the foregoing general description that the following detailed description is exemplary and explanatory, and intended to provide further explanation of the invention claimed.

BRIEF DESCRIPTION OF THE DRAWINGS

The accompanying drawings are included to provide a further understanding of the invention, and are incorporated in, and constitute a part of this specification that illustrate several embodiments of the invention, and together with the description serve to explain the principles of the invention.

FIG. 1 depicts the nucleic acid sequence (SEQ ID NO:1) of human MEKK1 and the predicted amino acid sequence (SEQ ID NO:2) of human MEKK1. The methionine-initiated open reading frame of human MEKK1 starts at nucleotide 7 and goes to nucleotide 4545 of SEQ ID NO:1.

FIG. 2 depicts a summary of the alignment of the human MEKK1 protein (SEQ ID NO:2) with a partial human MEKK1 protein (GenBank Accession Number AF04283), (SEQ ID NO:3) rat MEKK1 (GenBank Accession Number U48596) (SEQ ID NO:4), and mouse MEKK1 (GenBank Accession Number AF 117340.1) (SEQ ID NO:5).

DETAILED DESCRIPTION

Figure 3:
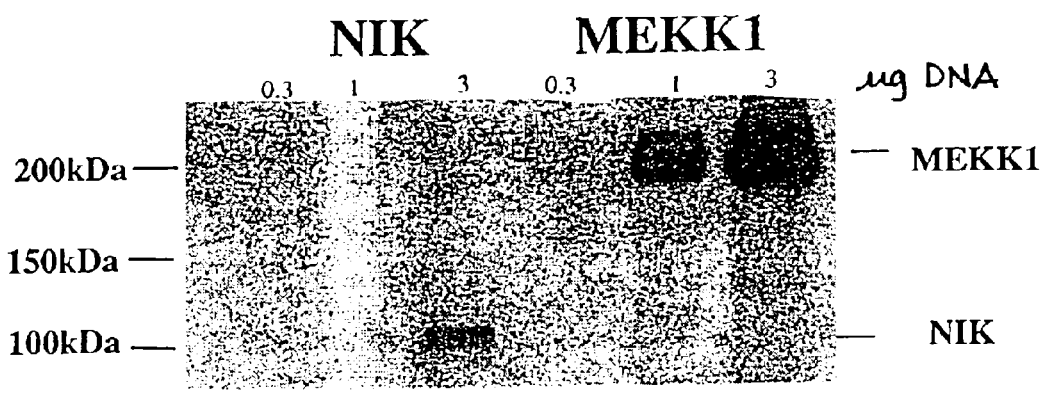
FIG. 3 shows the results of a Western blot for MEKK1 and NIK protein expression levels using an antiflag antibody.

The patent applications, patents and literature references cited herein indicate the knowledge of those of ordinary skill in this field and are hereby incorporated by reference in their entirety. In the case of inconsistencies between any reference cited herein and the specific teachings of the present disclosure, this disclosure will prevail. Similarly, any inconsistencies between an art-understood meaning of a term and a meaning of a term as specifically taught in the present disclosure will be resolved in favor of this disclosure.

The human full-length MEKK1 nucleic acid sequence (FIG. 1; SEQ ID NO:1), which is approximately 5245 nucleotides long including untranslated regions, contains a predicted methionine-initiated coding sequence of about 4536 nucleotides (nucleotides 7–4545 of SEQ ID NO:1. As used herein, "MEKK1 nucleic acid" and "MEKK1 gene" comprise nucleic acid sequences 1–5245 of SEQ ID NO:1. The coding sequence encodes a 1512 amino acid protein (SEQ ID NO:2). The open reading frame (ORF) analysis of the human MEKK1 protein of SEQ ID NO:2 indicates that the protein does not include a signal sequence nor does it include any transmembrane domains.

Human MEKK1 contains an activation loop between the kinase subdomain VII and VIII, specifically the two threonine amino acid residues 1400 and 1412. (Deak et al., *Biochem. J.* 322:185–192 (1997); and Siow et al., *J. Biol. Chem.* 272:75867594 (1997).) The ORF analysis of human MEKK1 also showed the following sites:

one predicted glycosaminoglycan attachment site (PS00002) at about amino acids 101 to 104 of SEQ ID NO:2;

four predicted cAMP- and cGMP-dependent protein kinase phosphorylation sites (PS00004) at about amino acids 272 to 275, 395 to 398, 585 to 588, 1023 to 1026 of SEQ ID NO:2;

twenty-two predicted protein kinase C phosphorylation sites (PS00005) at about amino acids 169 to 171, 258 to 260, 261 to 263, 281 to 283, 304 to 306, 379 to 381, 394 to 396, 397 to 399, 434 to 436, 514 to 516, 531 to 533, 657 to 659, 816 to 818, 823 to 825, 911 to 913, 928 to 930, 1021 to 1023, 1039 to 1041, 1070 to 1072, 1088 to 1090, 1148 to 1150, and 1166 to 1168 of SEQ ID NO:2;

nineteen predicted casein kinase II phosphorylation sites (PS00006) located at about amino acids 20 to 23, 232 to 235, 300 to 303, 429 to 432, 434 to 437, 457 to 460, 507 to 510, 660 to 672, 705 to 708, 782 to 785, 900 to 903, 923 to 926, 947 to 950, 997 to 1000, 1089 to 1092, 1114 to 1117, 1130 to 1133, 1166 to 1169, and 1280 to 1283 of SEQ ID NO:2;

one predicted tyrosine kinase phosphorylation site (PS00007) at about amino acids 1160 to 1167 of SEQ ID NO:2;

twenty-three predicted N-myristoylation sites (PS00008) from about amino acid 6 to 11, 16 to 21, 25 to 30, 100 to 105, 121 to 126, 222 to 227, 254 to a 259, 530 to 535, 570 to 575, 604 to 609, 611 to 616, 617 to 622, 872 to 877, 879 to 884, 914 to 919, 1096 to 1101, 1246 to 1251, 1252 to 1257, 1266 to 1271, 1328 to 1333, 1399 to 1404, 1407 to 1412, 1423 to 1428 of SEQ ID NO:2; and one amidation site (PS00009) from about amino acid residue 246 to 249 of SEQ ID NO: 2.

For general information regarding PFAM identifiers, PS prefix and PF prefix domain identification numbers, refer to Sonnhammer et al., *Protein* 28:405–420 (1997).

A plasmid containing the nucleotide sequence encoding human MEKK1 was deposited with American Type Culture Collection (ATCC), 10801 University Boulevard, Manassas, Va. 20110-2209, on May 18, 2000 and assigned Accession Number PTA-1836. This deposit will be maintained under the terms of the Budapest Treaty on the International Recognition of the Deposit of Microorganisms for the Purposes of Patent Procedure. This deposit was made merely as a convenience for those of skill in the art and is not an admission that a deposit is required under 35 U.S.C. §112.

The cloning method used herein was successful, compared to other methods tried previously in the art, for several reasons. Among these reasons were the screening of a lambda gt11 phage library. Second, the cDNA library used herein had a large insert, 5'-stretched, which enabled more full-length clones to be identified. Finally, the cDNA was made from normal human cDNA, while others in the art had unsuccessfully used three tumor cell lines to try and piece together the sequence.

The MEKK1 protein contains a significant number of structural characteristics in common within the kinase catalytic domain with other members of the MEKK family. The term "family", when referring to the protein and nucleic acid molecules of the invention, means two or more proteins or nucleic acid molecules having a common structural domain or motif and having sufficient amino acid or nucleotide sequence homology as defined herein. Such family members can be naturally or non-naturally occurring and can be from either the same or different species. For example, a family can contain a first protein of human origin as well as other distinct proteins of human origin, or alternatively, can contain homologues of non-human origin, e.g., rat or mouse proteins. Members of a family can also have common functional characteristics.

In some embodiments, a MEKK1 protein includes at least one phosphorylation site, for example, 1, 2, 3, 4, 5, 6, 7, 8, 9, 10, 11, 12, 13, 14, 15, 16, 17, 18, 19, 20, 21, 22 or more protein kinase C phosphorylation sites; and 1, 2, 3, 4, 5, 6, 7, 8, 9, 10, 11, 12, 13, 14, 15, 16, 17, 18, 19 or more casein kinase II phosphorylation sites; 1, 2, 3, 4 or more CAMP- and cGMP-dependent protein kinase phosphorylation sites; and at least one tyrosine kinase phosphorylation site. The MEKK1 protein can additionally include at least one, glycosaminoglycan attachment site; at least 1, 2, 3, 4, 5, 6, 7, 8, 9, 10, and preferably eighteen to twenty-three N-myristoylation sites; and at least one amidation site.

As the MEKK1 polypeptides of the invention may modulate MEKK1-mediated activities, they may be useful for developing novel diagnostic and therapeutic agents for MEKK1-mediated or related disorders, as described below.

As used herein, a "MEKK1 activity", "biological activity of MEKK1", or "functional activity of MEKK1", refers to an activity exerted by a MEKK1 protein, polypeptide, or nucleic acid molecule on, e.g., a MEKK1-responsive cell or on a MEKK1 substrate, e.g., a protein substrate, as determined in vivo or in vitro. In one embodiment, a MEKK1 activity is a direct activity, such as an association with a MEKK1 target molecule. A "target molecule" or "binding partner" is a molecule with which a MEKK1 protein binds or interacts in nature. A MEKK1 activity can also be an indirect activity, e.g., a cellular signaling activity mediated by interaction of the MEKK1 protein with a MEKK1 receptor.

A MEKK1 protein of the invention may display activities including mediating (1) activation of IκB kinase which leads to NFκB activation; (2) activation of ERK1 and ERK2 and activation of the c-Myc transcription factor independent of JNK activity; (3) apoptosis by both JNK-dependent and JNK-independent mechanisms; and (4) AP-1 activation via JNK-dependent pathway. For example, MEKK1 proteins may regulate processes involved, for example, in embryonic development or tissue differentiation. Examples of such embryonic development and tissue differentiation include neural development (such as axonal growth and/or guidance or growth), as well as tissue maintenance and function. In addition, MEKK1 may be involved in pathological conditions, such as neuronal degeneration, neoplastic transformation, and tumor progression.

Based on the above-described sequence similarities, the MEKK1 molecules of the present invention are predicted in some instances to have similar biological activities as other MEKK family members. Thus, the MEKK1 molecules and modulators of MEKK1 (particularly inhibitors of MEKK1) can serve as novel diagnostic targets and therapeutic agents for controlling protein-protein interaction disorders and signal transduction disorders, such as cellular proliferative and/or differentiative disorders selected from the group consisting of hyperplasia, neoplasia, and cancer, as well as degenerative diseases, such a neurodegenerative diseases, autoimmune diseases, inflammatory conditions, and allergic responses.

Examples of cellular proliferative and/or differentiative disorders include cancer, e.g., carcinoma, sarcoma, metastatic disorders or hematopoietic neoplastic disorders, e.g., leukemias. A metastatic tumor can arise from a multitude of primary tumor types, including, but not limited to, those of prostate, colon, lung, breast and liver origin.

As used herein, the terms "cancer", "hyperproliferative" and "neoplastic" refer to cells having the capacity for autonomous growth, i.e., an abnormal state or condition characterized by rapidly proliferating cell growth. Hyperproliferative and neoplastic disease states may be categorized as pathologic, i.e., characterizing or constituting a disease state, or may be categorized as non-pathologic, i.e., a deviation from normal but not associated with a: disease state. The term is meant to include all types of cancerous growths or oncogenic processes, and metastatic tissues or malignantly transformed cells, tissues, or organs, irrespective of histopathologic type or stage of invasiveness. "Pathologic hyperproliferative" cells occur in disease states characterized by malignant tumor growth. Examples of non-pathologic hyperproliferative cells include proliferation of cells associated with wound repair.

The terms "cancer" or "neoplasms" include malignancies of the various organ systems, including, for example, lung, breast, thyroid, lymphoid system, gastrointestinal system, and genito-urinary tract, as well as adenocarcinomas, which include malignancies such as most colon cancers, renal-cell carcinoma, prostate cancer and/or testicular tumors, non-small cell carcinoma of the lung, cancer of the small intestine and cancer of the esophagus.

The term "carcinoma" is art recognized and refers to malignancies of epithelial or endocrine tissues including respiratory system carcinomas, gastrointestinal system carcinomas, genitourinary system carcinomas, testicular carcinomas, breast carcinomas, prostatic carcinomas, endocrine system carcinomas, and melanomas. Exemplary carcinomas include those forming from tissue of the cervix, lung, prostate, breast, head and neck, colon and ovary. The term also includes carcinosarcomas, e.g., which include malignant tumors composed of carcinomatous and sarcomatous tissues. An "adenocarcinoma" refers to a carcinoma derived from glandular tissue or in which the tumor cells form recognizable glandular structures.

The term "sarcoma" is art recognized and refers to malignant tumors of mesenchymal derivation.

Additional examples of proliferative disorders include hematopoietic neoplastic disorders. As used herein, the term "hematopoietic neoplastic disorders" includes diseases involving hyperplastic/neoplastic cells of hematopoietic origin, e.g., arising from myeloid, lymphoid or erythroid lineages, or precursor cells thereof. Preferably, the diseases arise from poorly differentiated acute leukemias, e.g., erythroblastic leukemia and acute megakaryoblastic leukemia. Additional exemplary myeloid disorders include, but are not limited to, acute promyeloid leukemia (APML), acute myelogenous leukemia (AML) and chronic myelogenous leukemia (CML) (reviewed in Vaickus, L. (1991) *Crit Rev. in Oncol./Hemotol.* 11:267–97); lymphoid malignancies include, but are not limited to acute lymphoblastic leukemia (ALL) which includes B-lineage ALL and T-lineage ALL, chronic lymphocytic leukemia (CLL), prolymphocytic leukemia (PLL), hairy cell leukemia (HLL) and Waldenstrom's macroglobulinemia (WM). Additional forms of malignant lymphomas include, but are not limited to, non-Hodgkin lymphoma and variants thereof, peripheral T cell lymphomas, adult T cell leukemia/lymphoma (ATL), cutaneous T-cell lymphoma (CTCL), large granular lymphocytic leukemia (LGF), Hodgkin's disease, and Reed-Sternberg disease.

Examples of inflammatory conditions within the scope of the invention include, but are not limited to, asthma and chronic obstructive pulmonary disease, rheumatoid arthritis, multiple sclerosis, inflammatory bowel disease, e.g., Crohn's disease and ulcerative colitis, and complications arising from organ transplantation.

The MEKK1 protein, and derivatives and other variants of the sequence in SEQ ID NO:2 thereof, are collectively referred to as "polypeptides or proteins of the invention" or "MEKK1 polypeptides or proteins". Nucleic acid molecules encoding such polypeptides or proteins are collectively referred to as "nucleic acids of the invention" or "MEKK1 nucleic acids." MEKK1 molecules refer to MEKK1 nucleic acids, polypeptides, and antibodies.

As used herein, the term "nucleic acid molecule" includes DNA molecules (e.g., a cDNA or genomic DNA) and RNA molecules (e.g., an mRNA) and analogs of the DNA or RNA generated, e.g., by the use of nucleotide analogs. The nucleic acid molecule can be single-stranded or double-stranded, but preferably is double-stranded DNA.

The term "isolated or purified nucleic acid molecule" includes nucleic acid molecules which are separated from other nucleic acid molecules which are present in the natural source of the nucleic acid. For example, with regard to genomic DNA, the term "isolated" includes nucleic acid molecules which are separated from the chromosome with which the genomic DNA is naturally associated. Preferably, an "isolated" nucleic acid is free of sequences which naturally flank the nucleic acid (i.e., sequences located at the 5' and/or 3' ends of the nucleic acid) in the genomic DNA of the organism from which the nucleic acid is derived. For example, in various embodiments, the isolated nucleic acid molecule can contain less than about 5 kb, 4 kb, 3 kb, 2 kb, 1 kb, 0.5 kb or 0.1 kb of 5' and/or 3' nucleotide sequences which naturally flank the nucleic acid molecule in genomic DNA of the cell from which the nucleic acid is derived. Moreover, an "isolated" nucleic acid molecule, such as a cDNA molecule, can be substantially free of other cellular material, or culture medium when produced by recombinant techniques, or substantially free of chemical precursors or other chemicals when chemically synthesized.

As used herein, the term "hybridizes under stringent conditions" describes conditions for hybridization and washing. Stringent conditions are known to those skilled in the art and can be found, e.g., in *Current Protocols in Molecular Biology*, John Wiley & Sons, N.Y. (1989), 6.3.1–6.3.6. Aqueous and nonaqueous methods are described in that reference and either can be used. A preferred example of stringent hybridization conditions are hybridization in 6× sodium chloride/sodium citrate (SSC) at about 45° C., followed by one or more washes in 0.2×SSC, 0.1% SDS at 50° C. Another example of stringent hybridization conditions are hybridization in 6× sodium chloride/sodium citrate (SSC) at about 45° C., followed by one or more washes in 0.2×SSC, 0.1% SDS at 55° C. A further example of stringent hybridization conditions are hybridization in 6× sodium chloride/sodium citrate (SSC) at about 45° C., followed by one or more washes in 0.2×SSC, 0.1% SDS at 60° C. Preferably, stringent hybridization conditions are hybridization in 6× sodium chloride/sodium citrate (SSC) at about 45° C., followed by one or more washes in 0.2×SSC, 0.1% SDS at 65° C. Particularly preferred stringency conditions (and the conditions that should be used if the practitioner is uncertain about what conditions should be applied to determine if a molecule is within a hybridization limitation of the invention) are 0.5M Sodium Phosphate, 7% SDS at 65° C., followed by one or more washes at 0.2×SSC, 1% SDS at 65° C. Preferably, an isolated nucleic acid molecule of the invention that hybridizes under stringent conditions to the sequence of SEQ ID NO:1 or nucleotide 7 to nucleotide 4545 of SEQ ID NO:1, corresponds to a naturally-occurring nucleic acid molecule.

As used herein, a "naturally-occurring" nucleic acid molecule refers to an RNA or DNA molecule having a nucleotide sequence that occurs in nature (e.g., encodes a natural protein).

As used herein, the terms "gene" and "recombinant gene" refer to nucleic acid molecules which include an open reading frame encoding a MEKK1 protein, preferably a mammalian MEKK1 protein, and can further include non-coding regulatory sequences, and introns.

An "isolated" or "purified" polypeptide or protein is substantially free of cellular material or other contaminating proteins from the cell or tissue source from which the protein is derived, or substantially free from chemical precursors or other chemicals when chemically synthesized. In one embodiment, the language "substantially free" means preparation of MEKK1 protein having less than about 30%, 20%, 10% and more preferably 5% (by dry weight), of non-MEKK1 protein (also referred to herein as a "contaminating protein"), or of chemical precursors or non-MEKK1 chemicals. When the MEKK1 protein, or a biologically active portion thereof, is recombinantly produced, it is also preferably substantially free of culture medium, i.e., culture medium represents less than about 20%, more preferably less than about 10%, and most preferably less than about 5% of the volume of the protein preparation. The invention includes isolated or purified preparations of at least 0.01, 0.1, 1.0, and 10 milligrams in dry weight.

A "non-essential" amino acid residue is a residue that can be altered from the wild-type sequence of MEKK1 (e.g., the sequence of SEQ ID NO:1 or nucleotide 7 to nucleotide 4545 of SEQ ID NO:1, or the nucleotide sequence of the DNA insert of the plasmid deposited with ATCC as Accession Number PTA-1836) without abolishing or, more preferably, without substantially altering a biological activity of MEKK1, whereas an "essential" amino acid residue results in such a change. For example, amino acid residues that are conserved among the polypeptides of the present invention are predicted to be particularly unamenable to alteration.

A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g. aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, a predicted nonessential amino acid residue in a MEKK1 protein is preferably replaced with another amino acid residue from the same side chain family. Alternatively, in another embodiment, mutations can be introduced randomly along all or part of a MEKK1 coding sequence, such as by saturation mutagenesis, and the resultant mutant polypeptides can be screened for MEKK1 biological activity to identify mutant polypeptides that retain activity. Following mutagenesis of SEQ ID NO:1 or nucleotide 7 to nucleotide 4545 of SEQ ID NO:1, or the nucleotide sequence of the DNA insert of the plasmid deposited with ATCC as Accession Number PTA-1836, the encoded protein can be expressed recombinantly and the activity of the protein can be determined.

As used herein, a "biologically active portion" of a MEKK1 protein includes a fragment of a MEKK1 protein which participates in an interaction between a MEKK1 molecule and a non-MEKK1 molecule. Biologically active portions of a MEKK1 protein include peptides comprising amino acid sequences sufficiently homologous to, or derived from, the amino acid sequence of the MEKK1 protein, e.g., the amino acid sequence shown in SEQ ID NO:2, which include less amino acids than the full-length MEKK1 proteins, and exhibit at least one activity of a MEKK1 protein. Typically, biologically active portions comprise a domain or motif with at least one activity of the MEKK1 protein, e.g., signal transduction, cell-cell adhesion, cell migration, patterning, cellular growth and/or differentiation. A biologically active portion of a MEKK1 protein can be a polypeptide which is, for example, 10, 25, 50, 100, 200 or more amino acids in length. Biologically active portions of a MEKK1 protein can be used as targets for developing agents which modulate a MEKK1 mediated activity, e.g., protein-protein interaction, cell-cell adhesion, or signal transduction.

Calculations of homology or sequence identity between sequences (the terms are used interchangeably herein) are performed as follows.

To determine the percent identity of two amino acid sequences, or of two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). In a preferred embodiment, the length of a reference sequence aligned for comparison purposes is at least 30%, preferably at least 40%, more preferably at least 50%, even more preferably at least 60%, and even more preferably at least 70%, 80%, 90%, 95%, 96%, 97%, 98%, 99%, or 100% of the length of the reference sequence (e.g., when aligning a second sequence to the MEKK1 amino acid sequence of SEQ ID NO:2 having 1512 amino acid residues, at least 1450, preferably at least 1475, more preferably at least 1490, even more preferably at least 1500, and even more preferably at least 1506, or 1512 amino acid residues are aligned). The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences, taking into account the number of gaps, and the length of each gap, which need to be introduced for optimal alignment of the two sequences.

The comparison of sequences and determination of percent identity between two sequences can be accomplished using a mathematical algorithm. In a preferred embodiment, the percent identity between two amino acid sequences is determined using the Needleman and Wunsch (*J. Mol. Biol.* (48):444–453 (1970)) algorithm which has been incorporated into the GAP program in the GCG software package, using either a Blossum 62 matrix or a PAM250 matrix, and a gap weight of 16, 14, 12, 10, 8, 6, or 4 and a length weight of 1, 2, 3, 4, 5, or 6. In yet another preferred embodiment, the percent identity between two nucleotide sequences is determined using the GAP program in the GCG software package, using a NWSgapdna.CMP matrix and a gap weight of 40, 50, 60, 70, or 80 and a length weight of 1, 2, 3, 4, 5, or 6. A particularly preferred set of parameters (and the one that should be used if the practitioner is uncertain about what parameters should be applied to determine if a molecule is within a sequence identity or homology limitation of the invention) are a Blossum 62 scoring matrix with a gap penalty of 12, a gap extend penalty of 4, and a frameshift gap penalty of 5.

The percent identity between two amino acid or nucleotide sequences can be determined using the algorithm of E. Meyers and W. Miller (CABIOS, 4:11–17 (1989)) which has been incorporated into the ALIGN program (version 2.0), using a PAM120 weight residue table, a gap length penalty of 12 and a penalty of 4.

The nucleic acid and protein sequences described herein can be used as a "query sequence" to perform a search against public databases to, for example, identify other family members or related sequences. Such searches can be performed using the NBLAST and XBLAST programs (version 2.0) of Altschul et al., *J. Mol. Biol.* 215:403–10 (1990). BLAST nucleotide searches can be performed with the NBLAST program, score=100, wordlength=12 to obtain nucleotide sequences homologous to MEKK1 nucleic acid molecules of the invention. BLAST protein searches can be performed with the XBLAST program, score=50, wordlength=3 to obtain amino acid sequences homologous to MEKK1 protein molecules of the invention. To obtain gapped alignments for comparison purposes, Gapped BLAST can be utilized as described in Altschul et al., *Nucleic Acids Res.* 25(17):3389–3402 (1997). When utilizing BLAST and Gapped BLAST programs, the default parameters of the respective programs (e.g., XBLAST and NBLAST) can be used.

"Misexpression" or "aberrant expression", as used herein, refers to a non-wild type pattern of gene expression, at the RNA or protein level. It includes expression at non-wild type levels, i.e., over- or under-expression; a pattern of expression that differs from wild type in terms of the time or stage a, at which the gene is expressed, e.g., increased or decreased expression (as compared with wild type) at a predetermined developmental period or stage; a pattern of expression that differs from wild type in terms of decreased expression (as compared with wild type) in a predetermined cell type or tissue type; a pattern of expression that differs from wild type in terms of the splicing size, amino acid sequence, post-transitional modification, or biological activity of the expressed polypeptide; a pattern of expression that differs from wild type in terms of the effect of an environmental stimulus or extracellular stimulus on expression of the gene, e.g., a pattern of increased or decreased expression (as compared with wild type) in the presence of an increase or decrease in the strength of the stimulus.

"Subject", as used herein, can refer to a mammal, e.g., a human, or to an experimental or animal or disease model. The subject can also be a non-human animal, e.g., a horse, cow, goat, or other domestic animal.

A "purified preparation of cells", as used herein, refers to, in the case of plant or animal cells, an in vitro preparation of cells and not an entire intact plant or animal. In the case of cultured cells or microbial cells, it consists of a preparation of at least 10% and more preferably 50% of the subject cells.

Various aspects and embodiments of the invention are described in further detail below.

Isolated Nucleic Acid Molecules

In one aspect, the invention provides, an isolated or purified, nucleic acid molecule that encodes a MEKK1 polypeptide described herein, e.g., a full-length MEKK1 protein or a fragment thereof, e.g., a biologically active portion of MEKK1 protein. Also included is a nucleic acid fragment suitable for use as a hybridization probe, which can be used, e.g., to a identify nucleic acid molecule encoding a polypeptide of the invention, MEKK1 mRNA, and fragments suitable for use as primers, e.g., PCR primers for the amplification or mutation of nucleic acid molecules.

In one embodiment, an isolated nucleic acid molecule of the invention includes the nucleotide sequence shown in SEQ ID NO:1, or the nucleotide sequence of the DNA insert of the plasmid deposited with ATCC as Accession Number PTA-1836, or a portion of any of these nucleotide sequences. In one embodiment, the nucleic acid molecule includes sequences encoding the human MEKK1 protein (i.e., "the coding region", from nucleotides 7–4539 of SEQ ID NO:1), as well as 5' untranslated sequence corresponding to nucleotides 1–6 of SEQ ID NO:1 and 3' untranslated sequence corresponding to nucleotides 4546 to 5245 of SEQ ID NO:1. Alternatively, the nucleic acid molecule can include only the coding region of SEQ ID NO:1 (e.g., nucleotides 7–4545, and, e.g., no flanking sequences which normally accompany the subject sequence. In another embodiment, the nucleic acid molecule encodes a sequence corresponding to the mature protein from about amino acid 1 to amino acid 1512 of SEQ ID NO:2.

In another embodiment, an isolated nucleic acid molecule of the invention includes a nucleic acid molecule which is a complement of the nucleotide sequence shown in SEQ ID NO:1 or nucleotide 7 to nucleotide 4545 of SEQ ID NO: 1, or the nucleotide sequence of the cDNA insert of the plasmid deposited with ATCC as Accession Number PTA-1836, or a portion or fragment of any of these nucleotide sequences. In other embodiments, the nucleic acid molecule of the invention is sufficiently complementary to the nucleotide sequence shown in SEQ ID NO:1 or nucleotide 7 to nucleotide 4545 of SEQ ID NO:1, or the nucleotide sequence of the cDNA insert of the plasmid deposited with ATCC as Accession Number PITA-1836 such that it can hybridize to the nucleotide sequence shown in SEQ ID NO:1 or nucleotide 7 to nucleotide 4545 of SEQ ID NO:1, or the nucleotide sequence of the cDNA insert of the plasmid deposited with ATCC as Accession Number PTA-1836, thereby forming a stable duplex.

In one embodiment, an isolated nucleic acid molecule of the present invention includes a nucleotide sequence which is at least about: 60%, 65%, 70%, 75%, 80%, 85%, 90%, 91%, 92%, 93%, 94%, 95%, 96%, 97%, 98%, 99%, or more homologous to the entire length of the nucleotide sequence shown in SEQ ID NO:1 or nucleotide 7 to nucleotide 4545 of SEQ ID NO:1, or the entire length of the nucleotide sequence of the cDNA insert of the plasmid deposited with ATCC as Accession Number PTA-1836, or a portion, preferably of the same length, of any of these nucleotide sequence.

MEKK1 Nucleic Acid Fragments

A nucleic acid molecule of the invention can include only a portion of the nucleic acid sequence of SEQ ID NO:1 or nucleotide 7 to nucleotide 4545 of SEQ ID NO:1, or the nucleotide sequence of the cDNA insert of the plasmid deposited with ATCC as Accession Number PTA-1836. For example, such a nucleic acid molecule can include a fragment that can be used as a probe or primer or a fragment encoding a portion of a MEKK1 protein, e.g., an immunogenic or biologically active portion of a MEKK1 protein. A fragment can comprise nucleotides 3576–4542 of SEQ ID NO:1, which encodes a kinase or catalytic domain of human MEKK1. A fragment can comprise nucleotides 2632–4542 of SEQ ID NO:1, which encodes a cleaved/processed domain of human MEKK1. The nucleotide sequence determined from the cloning of the MEKK1 gene allows for the generation of probes and primers designed for use in identifying and/or cloning other MEKK1 family members, or fragments thereof, as well as MEKK1 homologues, or fragments thereof, from other species.

In another embodiment, a nucleic acid molecule includes a nucleotide sequence that includes part, or all, of the coding region and extends into either (or both) the 5' or 3' noncoding region. Thus, the following nucleic acid molecules are provided:

a nucleic add molecule comprising from about 10 to about 64 contiguous nucleotides from the nucleic acid sequence (SEQ ID NO:6) ATGGCGGCGGCG-GCGGGGAATCGCGCCTCGTCGGGATTC-CCGGGCGCCA GGGCTA and having at least 80% homology to the nucleic acid sequence shown in SEQ ID NO:1;

a nucleic acid molecule comprising from about 10 to about 64 contiguous nucleotides from the nucleic acid sequence (SEQ ID NO:7) GAGAAAATGGCGGCG-GCGGCGGGGAATCGCGCCTCGTCGGGAT-TCCCGG GCGCCAGGGCTA and having at least 80% homology to the nucleic acid sequence shown in SEQ ID NO:1;

a nucleic acid molecule comprising the nucleic acid sequence (SEQ ID NO:8) GCGCGCCCGCG and having at least 80% homology to the nucleic add sequence shown in SEQ ID NO:1;

a nucleic acid molecule comprising the nucleic acid sequence (SEQ ID NO:9) CCGCGAGCCGCG-GCGGC and having at least 80% homology to the nucleic acid sequence shown in SEQ ID NO:1;

a nucleic acid molecule comprising the nucleic acid sequence CTACGTCTA and having at least 80% homology to the nucleic acid sequence shown in SEQ ID NO:1;

a nucleic acid molecule comprising the nucleic acid sequence CCAGTTCCA and having at least 80% homology to the nucleic acid sequence shown in SEQ ID NO:1;

a nucleic acid molecule comprising the nucleic acid sequence GCTATRGC and having at least 80% homology to the nucleic acid sequence shown in SEQ ID NO:1;

a nucleic acid molecule comprising the nucleic acid sequence (SEQ ID NO:10) TTTGGATGGTCA and having at least 80% homology to the nucleic acid sequence shown in SEQ ID NO:1;

a nucleic acid molecule comprising the nucleic acid sequence (SEQ ID NO:11) GGACAGCTTC and having at least 80% homology to the nucleic acid sequence shown in SEQ ID NO:1;

a nucleic acid molecule comprising the nucleic acid sequence (SEQ ID NO:12) CCCCTGAGTGC and having at least 80% homology to the nucleic acid sequence shown in SEQ ID NO:1;

a nucleic acid molecule comprising the nucleic acid sequence (SEQ ID NO:13) GCCAGCATTT and having at least 80% homology to the nucleic acid sequence shown in SEQ ID NO:1;

a nucleic acid molecule comprising the nucleic acid sequence (SEQ ID NO:14) CATCTAGACCT and having at least 80% homology to the nucleic acid sequence shown in SEQ ID NO:1;

a nucleic acid molecule comprising the nucleic acid sequence (SEQ ID NO:15) GGCTGTAGCA and having at least 80% homology to the nucleic acid sequence shown in SEQ ID NO:1;

a nucleic acid molecule comprising the nucleic acid sequence (SEQ ID NO 16) GTAATGCTGT and having at least 80% homology to the nucleic acid sequence shown in SEQ ID NO:1;

a nucleic acid molecule comprising the nucleic acid sequence CCCAGTGAC and having at least 80% homology to the nucleic acid sequence shown in SEQ ID NO:1;

a nucleic acid molecule comprising the nucleic acid sequence (SEQ ID NO:17) GGATGCCCTCCCCAT and having at least 80% homology to the nucleic acid sequence shown in SEQ ID NO:1;

a nucleic acid molecule comprising the nucleic acid sequence GGCCTTTCG and having at least 80% homology to the nucleic acid sequence shown in SEQ ID NO:1.

A nucleic acid fragment can include a sequence encoding a domain, region, or functional site described herein. A nucleic acid fragment can also include one or more domain, region, or functional site described herein. Thus, for example, a nucleic acid fragment can contain a sequence encoding a protein kinase domain.

MEKK1 probes and primers are provided. Typically a probe/primer is an isolated or purified oligonucleotide. The oligonucleotide typically includes a region of nucleotide sequence that hybridizes under stringent conditions to at least about 7, 12 or 15, preferably about 20 or 25, more preferably about 30, 35, 40, 45, 50, 55, 60, 65, or 75 consecutive nucleotides of a sense or antisense sequence of SEQ ID NO:1 or nucleotide 7 to nucleotide 4545 of SEQ ID NO:1, or the nucleotide sequence of the DNA insert of the plasmid deposited with ATCC as Accession Number PTA-1836, or of a naturally occurring allelic variant or mutant of SEQ RD NO: 1 or nucleotide 7 to nucleotide 4545 of SEQ ID NO: 1, or the nucleotide sequence of the DNA insert of the plasmid deposited with ATCC as Accession Number PTA-1836.

In a preferred embodiment the nucleic acid is a probe which is at least 5 or 10, and less than 200, more preferably less than 100, or less than 50, base pairs in length. It should be identical, or differ by 1, or less than in 5 or 10 bases, from a sequence disclosed herein. If alignment is needed for this comparison the sequences should be aligned for maximum homology. "Looped" out sequences from deletions or insertions, or mismatches, are considered differences.

In another embodiment, a set of primers is provided, e.g., primers suitable for use in a PCR, which can be used to amplify a nucleic acid sequence which encodes a selected region of a MEKK1 sequence, e.g., a domain, region, site or other sequence described herein. The primers should be at least 5, 10, or 50 base pairs in length and less than 100, or less than 200, base pairs in length. The primers should be identical, or differ by one base from a sequence disclosed herein or from a naturally occurring variant, e.g., primers suitable for amplifying all or a portion of any of the following regions are provided:

a kinase or catalytic domain comprising amino acids 1191 to 1512 of SEQ ID NO:2; and a processed or cleaved domain comprising amino acids 876 to 1512 of SEQ ID NO:2.

A nucleic acid fragment can encode an epitope bearing region of a polypeptide described herein.

A nucleic acid fragment encoding a "biologically active portion of a MEKK1 polypeptide" can be prepared by isolating a portion of the nucleotide sequence of SEQ ID NO:1 or nucleotide 7 to nucleotide 4545 of SEQ ID NO:13, or the nucleotide sequence of the cDNA insert of the plasmid deposited with ATCC as Accession Number PTA-1836, which encodes a polypeptide having a MEKK1 biological activity (e.g., the biological activities of the MEKK1 proteins are described herein), expressing the encoded portion of the MEKK1 protein (e.g., by recombinant expression in vitro) and assessing the activity of the encoded portion of the MEKK1 protein. For example, a nucleic acid fragment encoding a biologically active portion of MEKK1 includes a protein kinase domain, e.g., amino acid residues 1191 to 1512 of SEQ ID NO:2. A nucleic acid fragment encoding a biologically active portion of a MEKK1 polypeptide, may comprise a nucleotide sequence which is greater than 900 or more nucleotides in length.

MEKK1 Nucleic Acid Variants

The invention further encompasses nucleic acid molecules that differ from the nucleotide sequence shown in SEQ ID NO:1 or nucleotide 7 to nucleotide 4545 of SEQ ID NO:1, or the nucleotide sequence of the cDNA insert of the plasmid deposited with ATCC as Accession Number PTA-1836. Such differences can be due to degeneracy of the genetic code and result in a nucleic acid which encodes the same MEKK1 proteins as those encoded by the nucleotide sequence disclosed herein. In another embodiment, an isolated nucleic acid molecule of the invention has a nucleotide sequence encoding a protein having an amino acid sequence which differs, by at least 1, but less than 5, 10, 20, 50, 75, or 100 amino acid residues from that shown in SEQ ID NO:2. If alignment is needed for this comparison the sequences should be aligned for maximum homology. "Looped" out sequences from deletions or insertions, or mismatches, are considered differences.

Nucleic acids of the inventor can be chosen for having codons, which are preferred, or non-preferred, for a particular expression system. For example, the nucleic acid can be one in which at least one codon, preferably, at least 10% or 20% of the codons, has been altered such that the sequence is optimized for expression in bacteria, e.g., *E. coli*, yeast, human, insect, or mammalian cells, e.g., Chinese hamster ovary (CHO) or SV40 transformed simian (COS) cells.

Nucleic acid variants can be naturally occurring, such as allelic variants (same locus), homologs (different locus), and orthologs (different organism), or can be non-naturally occurring. Non-naturally occurring variants can be made by mutagenesis techniques, including those applied to polynucleotides, cells, or organisms. The variants can contain nucleotide substitutions, deletions, inversions and insertions. Variation can occur in either or both the coding and non-coding regions. The variations can produce both conservative and non-conservative amino acid substitutions, as compared to the encoded product.

The invention further encompasses nucleic acid molecules that differ from the nucleotide sequence shown in SEQ ID NO:1 or nucleotide 7 to nucleotide 4545 of SEQ ID NO: 1, or the nucleotide sequence of the cDNA insert of the plasmid deposited with ATCC as Accession Number PTA-1836. Such differences can be due to degeneracy of the genetic code and result in a nucleic acid which encodes the same MEKK1 proteins as those encoded by the nucleotide sequence disclosed herein. In another embodiment, an isolated nucleic acid molecule of the invention has a nucleotide sequence encoding a protein having an amino acid sequence which differs, by at least 1, but less than 5, 10, 20, 50, 75, or 100 amino acid residues from that shown in SEQ ID NO:2. If alignment is needed for this comparison the sequences should be aligned for maximum homology. "Looped" out sequences from deletions or insertions, or mismatches, are considered differences.

Orthologs, homologs, and allelic variants can be identified using methods known in the art. These variants comprise a nucleotide sequence encoding a polypeptide that is 50%, at least about 55%, typically at least about 70–75%, more typically at least about 80–85%, and most typically at least about 90–95% or more, identical to the amino acid sequence shown in SEQ ID NO:2 or a fragment of this sequence. Such nucleic acid molecules can readily be identified as being able to hybridize under stringent conditions, to the nucleotide sequence shown in SEQ ID NO:1 or nucleotide 7 to nucleotide 4545 of SEQ ID NO:1 or a fragment of the sequence. Nucleic acid molecules corresponding to orthologs, homologs, and allelic variants of the MEKK1 cDNAs of the invention can further be isolated by mapping to the same chromosome or locus as the MEKK1 gene.

Preferred variants include those that are correlated with protein binding activities.

The invention also provides allelic variants of human MEKK1. An "allelic variant," as used herein, is a protein having at least about 75% amino acid sequence, preferably at least about 85%, more preferably at least about 95%, and most preferably at least about 99% identity to the amino acid sequence of MEKK1, or to a fragment thereof, or to a protein conjugate thereof which retains the biological activity of MEKK1. Allelic variants of MEKK1 include both functional and non-functional proteins. Functional allelic variants are naturally occurring amino acid sequence variants of the MEKK1 protein within a population that maintain the ability to bind MEKK1 binding partners. Functional allelic variants will typically contain only conservative substitution of one or more amino acids of SEQ ID NO:2, or substitution, deletion or insertion of non-critical residues in non-critical regions of the protein. Non-functional allelic variants are naturally-occurring amino acid sequence variants of the MEKK1, e.g., human MEKK1, protein within a population that do not have the ability to bind MEKK1 binding partners. Non-functional allelic variants will typically contain a non-conservative substitution, a deletion, or insertion, or premature truncation of the amino acid sequence of SEQ ID NO:2, or a substitution, insertion, or deletion in critical residues or critical regions of the protein.

This aspect of the inventions further includes MEKK1 allelic variant expression elements. Such elements include, without limitation, isolated or recombinant nucleic acid sequences encoding MEKK1; or nucleic acid sequences specifically homologous or complementary thereof, vectors comprising and such any such nucleic acid sequences, and recombinant expression vectors which express MEKK1 or antisense transcripts or dominant mutants thereof.

Moreover, nucleic acid molecules encoding other MEKK1 family members and, thus, which have a nucleotide sequence which differs from the MEKK1 sequences of SEQ ID NO:1 or nucleotide 7 to nucleotide 4545 of SEQ ID NO:13, or the nucleotide sequence of the cDNA insert of the plasmid deposited with ATCC as Accession Number PTA-1836 are intended to be within the scope of the invention.

"Dominant negative mutant" as used herein refers to a nucleic acid coding region sequence which has been changed with regard to at least one position in the sequence, relative to the corresponding wild type native version, preferably at a position which encodes a changed amino acid residue position at an active site required for biological and/or pharmacological activity in the native peptide. Dominant negative mutant embodiments of the invention, for example, include peptides comprising a sequence as depicted in SEQ ID No:2, wherein one or more positions corresponding to SEQ ID NO:2, e.g., lysine at position 1273, are substituted or deleted. Dominant negative mutants are, moreover, defined to be included within the scope of the disclosure of the variants sections above. Such dominant negative mutants can be prepared by art recognized procedures (see, e.g., Townsley et al., *Proc. Natl. Acad. Sci.*, USA. 94:2362–2367 (1997)).

Antisense Nucleic Acid Molecules, Ribozymes and Modified MEKK1 Nucleic Acid Molecules In another aspect, the invention features, an isolated nucleic acid molecule which is antisense to MEKK1. An "antisense" nucleic acid can include a nucleotide sequence which is complementary to a "sense" nucleic acid encoding a protein, e.g., complementary to the coding strand of a double-stranded cDNA molecule or complementary to an mRNA sequence. The antisense nucleic acid can be complementary to an entire MEKK1 coding strand, or to only a portion thereof (e.g., the coding region of human MEKK1 corresponding to nucleotide 7 to nucleotide 4545 of SEQ ID NO:1. In another embodiment, the antisense nucleic acid molecule is antisense to a "noncoding region" of the coding strand of a nucleotide sequence encoding MEKK1 (e.g., the 5' and 3' untranslated regions).

An antisense nucleic acid can be designed such that it is complementary to the entire coding region of MEKK1 mRNA, but more preferably is an oligonucleotide which is antisense to only a portion of the coding or noncoding region of MEKK1 mRNA. For example, the antisense oligonucleotide can be complementary to the region surrounding the translation start site of MEKK1 mRNA, e.g., between the −10 and +10 regions of the target gene nucleotide sequence of interest. An antisense oligonucleotide can be, for example, about 7, 10, 15, 20, 25, 30, 35, 40, 45, 50, 55, 60, 65, 70, 75, 80, or more nucleotides in length.

An antisense nucleic acid of the invention can be constructed using chemical synthesis and enzymatic ligation reactions using procedures known in the art. For example, an antisense nucleic acid (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids, e.g., phosphorothioate derivatives and acridine substituted nucleotides can be used. The antisense nucleic acid also can be produced biologically using an expression vector into which a nucleic acid has been subcloned in an antisense orientation (i.e., RNA transcribed from the inserted nucleic acid will be of an antisense orientation to a target nucleic acid of interest, described further in the following subsection).

The antisense nucleic acid molecules of the invention are typically administered to a subject (e.g., by direct injection at a tissue site), or generated in situ such that they hybridize with or bind to cellular mRNA and/or genomic DNA encoding a MEKK1 protein to thereby inhibit expression of the protein, e.g., by inhibiting transcription and/or translation. Alternatively, antisense nucleic acid molecules can be modified to target selected cells and then administered systemically. For systemic administration, antisense molecules can be modified such that they specifically bind to receptors or antigens expressed on a selected cell surface, e.g., by linking the antisense nucleic acid molecules to peptides or antibodies which bind to cell surface receptors or antigens. The antisense nucleic acid molecules can also be delivered to cells using the vectors described herein. To achieve sufficient intracellular concentrations of the antisense molecules, vector constructs in which the antisense nucleic acid molecule is placed under the control of a strong pol II or pol III promoter are preferred.

In yet another embodiment, the antisense nucleic acid molecule of the invention is an α-anomeric nucleic acid molecule. An α-anomeric nucleic acid molecule forms specific double-stranded hybrids with complementary RNA in which, contrary to the usual β-units, the strands run parallel to each other (Gaultier et al., *Nucleic Acids. Res.* 15:6625–6641 (1987)). The antisense nucleic acid molecule can also comprise a 2'-o-methylribonucleotide (Inoue et al., *Nucleic Acids Res.* 15:6131–6148 (1987)) or a chimeric RNA-DNA analogue (Inoue et al., *FEBS Lett.* 215:327–330 (1987)).

In still another embodiment, an antisense nucleic acid of the invention is a ribozyme. A ribozyme having specificity for a MEKK1 encoding nucleic acid can include one or more sequences complementary to the nucleotide sequence of a MEKK1 cDNA disclosed herein (i.e., SEQ ID NO:1 or nucleotide 7 to nucleotide 4545 of SEQ ID NO:1), and a sequence having known catalytic sequence responsible for mRNA cleavage (see U.S. Pat. No. 5,093,246 or Haselhoff and Gerlach (1988) *Nature* 334:585–591). For example, a derivative of a Tetrahymena L-19 IVS RNA can be constructed in which the nucleotide sequence of the active site is complementary to the nucleotide sequence to be cleaved in a MEKK1-encoding mRNA. (See, e.g., Cech et al., U.S. Pat. No. 4,987,071; and Cech et al., U.S. Pat. No. 5,116, 742.) Alternatively, MEKK1 mRNA can be used to select a catalytic RNA having a specific ribonuclease activity from a pool of RNA molecules. (See, e.g., Bartel et al., *Science* 261:1411–1418, (1993))

MEKK1 gene expression can be inhibited by targeting nucleotide sequences complementary to the regulatory region of the MEKK1 (e.g., the MEKK1 promoter and/or enhancers) to form triple helical structures that prevent transcription of the MEKK1 gene in target cells. See, generally, Helene, *Anticancer Drug Des.* 6(6):569–84 (1991); Helene et al., *Ann. N.Y. Acad. Sci.* 660:27–36 (1992); and Maher, *Bioassays* 14(12):807–15 (1992). The potential sequences that can be targeted for triple helix formation can be increased by creating a so called "switchback" nucleic acid molecule. Switchback molecules are synthesized in an alternating 5'-3',3'-5' manner, such that they base pair with first one strand of a duplex and then the other, eliminating the necessity for a sizeable stretch of either purines or pyrimidines to be present on one strand of a duplex.

The invention also provides detectably labeled oligonucleotide primer and probe molecules. Typically, such labels are chemiluminescent, fluorescent, radioactive, or calorimetric.

A MEKK1 nucleic acid molecule can be modified at the base moiety, sugar moiety or phosphate backbone to improve, e.g., the stability, hybridization, or solubility of the molecule. For example, the deoxyribose phosphate backbone of the nucleic acid molecules can be modified to generate peptide nucleic acids (see Hyrup et al., *Bioorganic & Medicinal Chemistry* 4 (1): 5–23 (1996)). As used herein, the terms "peptide nucleic acid" or "PNA" refers to a nucleic acid mimic, e.g., a DNA mimic, in which the deoxyribose phosphate backbone is replaced by a pseudopeptide backbone and only the four natural nucleobases are retained. The neutral backbone of a PNA can allow for specific hybridization to DNA and RNA under conditions of low ionic strength. The synthesis of PNA oligomers can be performed using standard solid phase peptide synthesis protocols as described in Hyrup et al., (1996) supra; Perry-O'Keefe et al., *Proc. Natl. Acad. Sci.* 93: 14670–675 (1996).

PNAs of MEKK1 nucleic acid molecules can be used in therapeutic and diagnostic applications. For example, PNAs can be used as antisense or antigene agents for sequence-specific modulation of gene expression by, for example, inducing transcription or translation arrest or inhibiting replication. PNAs of MEKK1 nucleic acid molecules can also be used in the analysis of single base pair mutations in a gene (e.g., by PNA-directed PCR clamping); as 'artificial restriction enzymes' when used in combination with other enzymes, (e.g., S1 nucleases (Hyrup B. (1996) supra)); or as probes or primers for DNA sequencing or hybridization (Hyrup et al., (1996) supra; Perry-O'Keefe supra).

In other embodiments, the oligonucleotide may include other appended groups such as peptides (e.g., for targeting host cell receptors in vivo), or agents facilitating transport across the cell membrane (see, e.g., Letsinger et al., *Proc. Natl. Acad. Sci. USA* 86:6553–6556 (1989); Lemaitre et al., *Proc. Natl. Acad. Sci. USA* 84:648–652 (1987); PCT Publication No. WO88/09810) or the blood-brain barrier (see, e.g., PCT Publication No. WO89/10134). In addition, oligonucleotides can be modified with hybridization-triggered cleavage agents (See, e.g., Krol et al., *Bio-Techniques* 6:958–976 (1988)) or intercalating agents. (See, e.g., Zon *Pharm. Res.* 5:539–549 (1988)). To this end, the oligonucleotide may be conjugated to another molecule, (e.g., a peptide, hybridization triggered cross-linking agent, transport agent, or hybridization-triggered cleavage agent).

The invention also includes molecular beacon oligonucleotide primer and probe molecules having at least one region which is complementary to a MEKK1 nucleic acid of the invention, two complementary regions one having a fluorophore and one a quencher such that the molecular beacon is useful for quantitating the presence of the MEKK1 nucleic acid of the invention in a sample. Molecular beacon nucleic acids are described, for example, in Lizardi et al., U.S. Pat. No. 5,854,033; Nazarenko et al., U.S. Pat. No. 5,866,336, and Livak et al., U.S. Pat. No. 5,876,930.

Isolated MEKK1 Polypeptides

In another aspect, the invention features an isolated MEKK1 protein, or fragment, e.g., a biologically active portion, for use as immunogens or antigens to raise or test (or more generally, to bind) anti-MEKK1 antibodies. MEKK1 protein can be isolated from cells or tissue sources using standard protein purification techniques. MEKK1 protein or fragments thereof can be produced by recombinant DNA techniques or synthesized chemically.

Polypeptides of the invention include those which arise as a result of the existence of multiple genes, alternative transcription events, alternative RNA splicing events, and alternative translational and postranslational events. The polypeptide can be expressed in systems, e.g., cultured cells, which result in substantially the same postranslational modifications present when expressed the polypeptide is expressed in a native cell, or in systems which result in the alteration or omission of postranslational modifications, e.g., gycolsylation or cleavage, present when expressed in a native cell. As used herein, "MEKK1 protein" and "MEKK1 polypeptide" comprises the amino acid sequences of SEQ ID NO:2.

In a preferred embodiment, a MEKK1 polypeptide has one or more of the following characteristics:

(i) it has the ability to modulate a signal transduction pathway;

(ii) it modulates a protein binding interaction;

(iii) it has a molecular weight, e.g., a deduced molecular weight, of SEQ ID NO:2;

(iv) it has an amino acid composition or other physical characteristics of SEQ ID NO:2;

(v) it has an overall sequence similarity of at least 60%, preferably at least 70%, more preferably at least 80, 90, 95%, 96%, 97%, 98%, or 99% with a polypeptide of SEQ ID NO:2;

(vi) it has a kinase domain which is preferably about 70%, 80%, 90% or 95% homologous with amino acid residues 1191 to 1512 of SEQ ID NO:2; or (vii) it has a processed/cleaved domain which is preferably about 70%, 80%, 90% or 95% homologous with amino acid residues 876 to 1512 of SEQ ID NO:2.

In other embodiments, a MEKK1 polypeptide is a polypeptide with one or more of the following characteristics:

a polypeptide comprising from about 5 to about 19 contiguous amino acids from the amino acid sequence (SEQ ID NO:18) MAAAAGNRASSSGFPGARAT and having at least 80% homology to the amino acid sequence shown in SEQ ID NO:2;

a polypeptide comprising from about 5 to about 19 contiguous amino acids from the amino acid sequence (SEQ ID NO:19) EKMAAAAGNRASSSGFPGARAT and having at least 80% homology to the amino acid sequence shown in SEQ ID NO:2;

a polypeptide comprising the amino acid sequence (SEQ ID NO:20) SAPAA and having at least 80% homology to the amino acid sequence shown in SEQ ID NO:2;

a polypeptide comprising the amino acid sequence (SEQ ID NO:21) ASRGG and having at least 80% homology to the amino acid sequence shown in SEQ ID NO:2;

a polypeptide comprising the amino acid sequence (SEQ ID NO:22) CARGT and having at least 80% homology to the amino acid sequence shown in SEQ ID NO:2;

a polypeptide comprising the amino acid sequence (SEQ ID NO:23) VSSSTH and having at least 80% homology to the amino acid sequence shown in SEQ ID NO:2;

a polypeptide comprising the amino acid sequence (SEQ ID NO:24) LMAIADE and having at least 80% homology to the amino acid sequence shown in SEQ ID NO:2;

a polypeptide comprising the amino acid sequence (SEQ ID NO:25) TLDGQQDSFLQASVPNNYLETTENS-SPECT and having at least 80% homology to the amino acid sequence shown in SEQ ID NO:2;

a polypeptide comprising the amino acid sequence (SEQ ID NO:26) LASISV and having at least 80% homology to the amino acid sequence shown in SEQ ID NO:2;

a polypeptide comprising the amino acid sequence (SEQ ID NO:27) SFGCSSNSSNAVIPSDE and having at least 80% homology to the amino acid sequence shown in SEQ ID NO:2; or a polypeptide comprising the amino acid sequence (SEQ ID NO:28) SQDALPIVPQLQVENGEDIIIQQDTPE-TLPGHTKAKQPYREDT and having at least 80% homology to the amino acid sequence shown in SEQ ID NO:2.

Some embodiments of the MEKK1 protein, or fragment thereof, differ from the corresponding sequence in SEQ ID NO:2. In one embodiment it differs by at least one but by less than 15, 10 or 5 amino acid residues. In another it differs from the corresponding sequence in SEQ ID NO:2 by at least one residue but less than 20%, 15%, 10% or 5% of the residues in it differ from the corresponding sequence in SEQ ID NO:2. (If this comparison requires alignment the sequences should be aligned for maximum homology. "Looped" out sequences from deletions or insertions, or mismatches, are considered differences.) The differences are, preferably, differences or changes at a non-essential residue or a conservative substitution. In a preferred embodiment the differences are not in a protein kinase domain.

Other embodiments include a protein that contain one or more changes in amino acid sequence, e.g., a change in an amino acid residue which is not essential for activity. Such MEKK1 proteins differ in amino acid sequence from SEQ ID NO:2, yet retain biological activity.

In one embodiment, a biologically active portion of a MEKK1 protein includes a protein kinase domain. Moreover, other biologically active portions, in which other regions of the protein are deleted, can be prepared by recombinant techniques and evaluated for one or more of the functional activities of a native MEKK1 protein.

In a preferred embodiment, the MEKK1 protein has the amino acid sequence shown in SEQ ID NO:2. In other embodiments, the MEKK1 protein is substantially identical to SEQ ID NO:2. In yet another embodiment, the MEKK1 protein is substantially identical to SEQ ID NO:2 and retains the functional activity of the protein of SEQ ID NO:2, as described in detail in subsection I above. Thus, the following nucleic acid molecules are provided;

MEKK1 Chimeric or Fusion Proteins

In another aspect, the invention provides MEKK1 chimeric or fusion proteins. As used herein, a MEKK1 "chimeric protein" or "fusion protein" includes a MEKK1 polypeptide linked to a non-MEKK1 polypeptide. A "non-MEKK1 polypeptide" refers to a polypeptide having an amino acid sequence corresponding to a protein which is not substantially homologous to the MEKK1 protein, e.g., a protein which is different from the MEKK1 protein and which is derived from the same or a different organism. The MEKK1 polypeptide of the fusion protein can correspond to all or a portion e.g., a fragment described herein of a MEKK1 amino acid sequence. In a preferred embodiment, a MEKK1 fusion protein includes at least one (or two) biologically active portion of a MEKK1 protein. The non-MEKK1 polypeptide can be fused to the N-terminus or C-terminus of the MEKK1 polypeptide.

The fusion protein can include a moiety which has a high affinity for a ligand. For example, the fusion protein can be a GST-MEKK1 fusion protein in which the MEKK1 sequences are fused to the C-terminus of the GST sequences. Such fusion proteins can facilitate the purification of recombinant MEKK1. Alternatively, the fusion protein can be a MEKK1 protein containing a heterologous signal sequence at its N-terminus. In certain host cells (e.g., mammalian host cells), expression and/or secretion of MEKK1 can be increased through use of a heterologous signal sequence.

Fusion proteins can include all or a part of a serum protein, e.g., an IgG constant region, or human serum albumin.

The MEKK1 fusion proteins of the invention can be incorporated into pharmaceutical compositions and administered to a subject in vivo. The MEKK1 fusion proteins can be used to affect the bioavailability of a MEKK1 substrate. MEKK1 fusion proteins may be useful therapeutically for the treatment of disorders caused by, for example, (i) aberrant modification or mutation of a gene encoding a MEKK1 protein; (ii) mis-regulation of the MEKK1 gene; and (iii) aberrant post-translational modification of a MEKK1 protein.

Moreover, the MEKK1-fusion proteins of the invention can be used as immunogens to produce anti-MEKK1 antibodies in a subject, to purify MEKK1 ligands and in screening assays to identify molecules which inhibit the interaction of MEKK1 with a MEKK1 substrate.

Expression vectors are commercially available that already encode a fusion moiety (e.g., a GST polypeptide). A MEKK1-encoding nucleic acid can be cloned into such an expression vector such that the fusion moiety is linked in-frame to the MEKK1 protein.

Variants of MEKK1 Proteins

In another aspect, the invention also features a variant of a MEKK1 polypeptide, e.g., which functions as an agonist (mimetics) or as an antagonist. Variants of the MEKK1 proteins can be generated by mutagenesis, e.g., discrete point mutation, the insertion or deletion of sequences or the truncation of a MEKK1 protein. An agonist of the MEKK1 proteins can retain substantially the same, or a subset, of the biological activities of the naturally occurring form of a MEKK1 protein. An antagonist of a MEKK1 protein can inhibit one or more of the activities of the naturally occurring form of the MEKK1 protein by, for example, competitively modulating a MEKK1-mediated activity of a MEKK1 protein. Thus, specific biological effects can be elicited by treatment with a variant of limited function. Preferably, treatment of a subject with a variant having a subset of the biological activities of the naturally occurring form of the protein has fewer side effects in a subject relative to treatment with the naturally occurring form of the MEKK1 protein.

Variants of a MEKK1 protein can be identified by screening combinatorial libraries of mutants, e.g., truncation mutants, of a MEKK1 protein for agonist or antagonist activity.

Libraries of fragments e.g., N-terminal, C-terminal, or internal fragments, of a MEKK1 protein coding sequence can be used to generate a variegated population of fragments for screening and subsequent selection of variants of a MEKK1 protein.

Variants in which a cysteine residues is added or deleted or in which a residue which is glycosylated is added or deleted are particularly preferred.

Methods for screening gene products of combinatorial libraries made by point mutations or truncation, and for screening cDNA libraries for gene products having a selected property. Recursive ensemble mutagenesis (REM), a new technique which enhances the frequency of functional mutants in the libraries, can be used in combination with the screening assays to identify MEKK1 variants (Arkin and Yourvan (1992) *Proc. Natl. Acad. Sci. USA* 89:7811–7815; Delgrave et al., *Protein Engineering* 6(3):327–331 (1993)).

Cell based assays can be exploited to analyze a variegated MEKK1 library. For example, a library of expression vectors can be transfected into a cell line, e.g., a cell line which ordinarily responds to MEKK1 in a substrate-dependent manner. The transfected cells are then contacted with MEKK1 and the effect of the expression of the mutant on signaling by the MEKK1 substrate can be detected, e.g., by measuring binding to a growth factor or cell surface receptor. Plasmid DNA can then be recovered from the cells which score for inhibition, or alternatively, potentiation of signaling by the MEKK1 substrate, and the individual clones further characterized.

In another aspect, the invention features a method of making a MEKK1 polypeptide, e.g., a peptide having a non-wild type activity, e.g., an antagonist, agonist, or super agonist of a naturally occurring MEKK1 polypeptide, e.g., a naturally occurring MEKK1 polypeptide. The method includes: altering the sequence of a MEKK1 polypeptide, e.g., altering the sequence, e.g., by substitution or deletion of one or more residues of a non-conserved region, a domain or residue disclosed herein, and testing the altered polypeptide for the desired activity.

In another aspect, the invention features a method of making a fragment or analog of a MEKK1 polypeptide a biological activity of a naturally occurring MEKK1 polypeptide. The method includes: altering the sequence, e.g., by substitution or deletion of one or more residues, of a MEKK1 polypeptide, e.g., altering the sequence of a non-conserved region, or a domain or residue described herein, and testing the altered polypeptide for the desired activity.

Anti-MEKK1 Antibodies

In another aspect, the invention provides an anti-MEKK1 antibody. The term "antibody" as used herein refers to an immunoglobulin molecule or immunologically active portion thereof, i.e., an antigen-binding portion. Examples of immunologically active portions of immunoglobulin molecules include F(ab) and F(ab')$_2$ fragments which can be generated by treating the antibody with an enzyme such as pepsin.

The antibody can be a polyclonal, monoclonal, recombinant, e.g., a chimeric or humanized, fully human, non-human, e.g., murine, or single chain antibody. In a preferred embodiment it has effector function and can fix complement. The antibody can be coupled to a toxin or imaging agent.

A full-length MEKK1 protein or, antigenic peptide fragment of MEKK1 can be used as an immunogen or can be used to identify anti-MEKK1 antibodies made with other immunogens, e.g., cells, membrane preparations, and the like. The antigenic peptide of MEKK1 should include at least 8 amino acid residues of the amino acid sequence shown in SEQ ID NO:2 and encompasses an epitope of MEKK1. Preferably, the antigenic peptide includes, at least 10 amino acid residues, more preferably at least 15 amino acid residues, even more preferably at least 20 amino acid residues, and most preferably at least 30 amino acid residues.

Antibodies reactive with, or specific for, any of the regions or domains described herein are provided.

Preferred epitopes encompassed by the antigenic peptide are regions of MEKK1 are located on the surface of the protein, e.g., hydrophilic regions, as well as regions with high antigenicity. For example, an Emini surface probability analysis of the human MEKK1 protein sequence can be used to indicate the regions that have a particularly high probability of being localized to the surface of the MEKK1 protein and are thus likely to constitute surface residues useful for targeting antibody production.

In a preferred embodiment the antibody binds an epitope on any domain or region on MEKK1 proteins described herein.

Chimeric, humanized, but most preferably, completely human antibodies are desirable for applications which include repeated administration, e.g., therapeutic treatment (and some diagnostic applications) of human patients.

The anti-MEKK1 antibody can be a single chain antibody. A single-chain antibody (scFV) may be engineered (see, for example, Colcher et al., *Ann N Y Acad Sci* June 30; 880:263–80 (1999); and Reiter, *Clin Cancer Res* February; 2(2):245–52 (1996)). The single chain antibody can be dimerized or multimerized to generate multivalent antibodies having specificities for different epitopes of the same target MEKK1 protein.

In a preferred embodiment, the antibody has reduced ability or no ability to bind an Fc receptor, for example, where it is an isotype or subtype, fragment or other mutant, which does not support binding to an Fc receptor, or where it has a mutagenized or deleted Fc receptor binding region.

An anti-MEKK1 antibody (e.g., monoclonal antibody) can be used to isolate MEKK1 by standard techniques, such as affinity chromatography or immunoprecipitation. Moreover, an anti-MEKK1 antibody can be used to detect MEKK1 protein (e.g., in a cellular lysate or cell supernatant) in order to evaluate the abundance and pattern of expression of the protein. Anti-MEKK1 antibodies can be used diagnostically to monitor protein levels in tissue as part of a clinical testing procedure, e.g., to, for example, determine the efficacy of a given treatment regimen. Detection can be facilitated by coupling (i.e., physically linking) the antibody to a detectable substance (i.e., antibody labeling). Examples of detectable substances include various enzymes, prosthetic groups, fluorescent materials, luminescent materials, bioluminescent materials, and radioactive materials. Examples of suitable enzymes include horseradish peroxidase, alkaline phosphatase, galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{125}$I, $^{131}$I, $^{35}$S or $^{3}$H.

Recombinant Expression Vectors, Host Cells and Genetically Engineered Cells

In another aspect, the invention includes, vectors, preferably expression vectors, containing a nucleic acid encoding a polypeptide described herein. As used herein, the term "vector" refers to a nucleic acid molecule capable of transporting another nucleic acid to which it has been linked and can include a plasmid, cosmid or viral vector. The vector can be capable of autonomous replication or it can integrate into a host DNA. Viral vectors include, e.g., replication defective retroviruses, adenoviruses and adeno-associated viruses.

A vector can include a MEKK1 nucleic acid in a form suitable for expression of the nucleic acid in a host cell. Preferably the recombinant expression vector includes one or more regulatory sequences operatively linked to the nucleic acid sequence to be expressed. The term "regulatory sequence" includes promoters, enhancers and other expression control elements (e.g., polyadenylation signals). Regulatory sequences include those which direct constitutive expression of a nucleotide sequence, as well as tissue-specific regulatory and/or inducible sequences. The design of the expression vector can depend on such factors as the choice of the host cell to be transformed, the level of expression of protein desired, and the like. The expression vectors of the invention can be introduced into host cells to thereby produce proteins or polypeptides, including fusion proteins or polypeptides, encoded by nucleic acids as described herein (e.g., MEKK1 proteins, mutant forms of MEKK1 proteins, fusion proteins, and the like).

The recombinant expression vectors of the invention can be designed for expression of MEKK1 proteins in prokaryotic or eukaryotic cells. For example, polypeptides of the invention can be expressed in *E. coli*, insect cells (e.g., using baculovirus expression vectors), yeast cells or mammalian cells. Suitable host cells are discussed further in Goeddel, *Gene Expression Technology: Methods in Enzymology* 185, Academic Press, San Diego, Calif. (1990). Alternatively, the recombinant expression vector can be transcribed and translated in vitro, for example using T7 promoter regulatory sequences and T7 polymerase.

Expression of proteins in prokaryotes is most often carried out in *E. coli* with vectors containing constitutive or inducible promoters directing the expression of either fusion or non-fusion proteins. Fusion vectors add a number of amino acids to a protein encoded therein, usually to the amino terminus of the recombinant protein. Such fusion vectors typically serve three purposes: 1) to increase expression of recombinant protein; 2) to increase the solubility of the recombinant protein; and 3) to aid in the purification of the recombinant protein by acting as a ligand in affinity purification. Often, a proteolytic cleavage site is introduced at the junction of the fusion moiety and the recombinant protein to enable separation of the recombinant protein from the fusion moiety subsequent to purification of the fusion protein. Such enzymes, and their cognate recognition sequences, include Factor Xa, thrombin and enterokinase. Typical fusion expression vectors include pGEX (Pharmacia Biotech Inc; Smith et al., *Gene* 67:3140 (1988)), pMAL (New England Biolabs, Beverly, Mass.) and pRIT5 (Pharmacia, Piscataway, N.J.) which fuse glutathione S-transferase (GST), maltose E binding protein, or protein A, respectively, to the target recombinant protein.

Purified fusion proteins can be used in MEKK1 activity assays, (e.g., direct assays or competitive assays described in detail below), or to generate antibodies specific for MEKK1 proteins. In a preferred embodiment, a fusion protein expressed in a retroviral expression vector of the present invention can be used to infect bone marrow cells which are subsequently transplanted into irradiated recipients. The pathology of the subject recipient is then examined after sufficient time has passed (e.g., six (6) weeks).

To maximize recombinant protein expression in, e.g., *E. coli*, is to express the protein in a host bacteria with an impaired capacity to proteolytically cleave the recombinant protein (Gottesman, S., *Gene Expression Technology: Methods in Enzymology* 185, Academic Press, San Diego, Calif. (1990) 119–128). Another strategy is to alter the sequence of the nucleic acid to be inserted into an expression vector so that the individual codons for each amino acid are those preferentially utilized in the host bacteria, e.g., *E. coli* (Wada et al., *Nucleic Acids Res.* 20:2111–2118 (1992)). Such alteration of nucleic acid sequences of the invention can be carried out by standard DNA synthesis techniques.

The MEKK1 expression vector can be a yeast expression vector, a vector for expression in insect cells, e.g., a baculovirus expression vector or a vector suitable for expression in mammalian cells.

When used in mammalian cells, the expression vector's control functions are often provided by viral regulatory elements. For example, commonly used promoters are derived from polyoma, Adenovirus 2, cytomegalovirus and Simian Virus 40.

In another embodiment, the recombinant mammalian expression vector is capable of directing expression of the nucleic acid preferentially in a particular cell type (e.g., tissue-specific regulatory elements are used to express the nucleic acid). Non-limiting examples of suitable tissue-specific promoters include the albumin promoter (liver-specific; Pinkert et al., *Genes Dev.* 1:268–277 (1987)), lymphoid-specific promoters (Calame et al., *Adv. Immunol.* 43:235275 (1988)), in particular promoters of T cell receptors (Winoto et al., *EMBO J.* 8:729–733 (1989)) and immunoglobulins (Banerji et al., *Cell* 33:729–740 (1983)); (Queen et al., *Cell* 33:741–748 (1983)), neuron-specific promoters (e.g., the neurofilament promoter; Byrne et al., *Proc. Natl. Acad. Sci. USA* 86:5473–5477 (1989)), pancreas-specific promoters (Edlund et al., *Science.* 230:912–916 (1985)), and mammary gland-specific promoters (e.g., milk whey promoter; U.S. Pat. No. 4,873,316 and European Application Publication No. 264,166). Developmentally-regulated promoters are also encompassed, for example, the murine hox promoters (Kessel et al., *Science* 249:374–379 (1990)) and the fetoprotein promoter (Campes et al., *Genes Dev.* 3:537–546 (1989)).

The invention further provides a recombinant expression vector comprising a DNA molecule of the invention cloned into the expression vector in an antisense orientation. Regulatory sequences (e.g., viral promoters and/or enhancers) operatively linked to a nucleic acid cloned in the antisense orientation can be chosen which direct the constitutive, tissue specific or cell type specific expression of antisense RNA in a variety of cell types. The antisense expression vector can be in the form of a recombinant plasmid, phagemid or attenuated virus. For a discussion of the regulation of gene expression using antisense genes see Weintraub et al., Antisense RNA as a molecular tool for genetic analysis, *Reviews—Trends in Genetics*, Vol. 1(1) (1986).

Another aspect the invention provides a host cell which includes a nucleic acid molecule described herein, e.g., a MEKK1 nucleic acid molecule within a recombinant expression vector or a MEKK1 nucleic acid molecule containing sequences which allow it to homologously recombine into a specific site of the host cell's genome. The terms "host cell" and "recombinant host cell" are used interchangeably herein. Such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

A host cell can be any suitable prokaryotic or eukaryotic cell. For example, a MEKK1 protein can be expressed in bacterial cells such as E. coli, insect cells, yeast or mammalian cells, such as CHO or COS cells. Other suitable host cells are known to those skilled in the art.

Vector DNA can be introduced into host cells via conventional transformation or transfection techniques. As used herein, the terms "transformation" and "transfection" are intended to refer to a variety of art-recognized techniques for introducing foreign nucleic acid (e.g., DNA) into a host cell, including calcium phosphate or calcium chloride co-precipitation, DEAE-dextran-mediated transfection, lipofection, or electroporation.

A host cell of the invention can be used to produce (i.e., express) a MEKK1 protein. Accordingly, the invention further provides methods for producing a MEKK1 protein using the host cells of the invention. In one embodiment, the method includes culturing the host cell of the invention (into which a recombinant expression vector encoding a MEKK1 protein has been introduced) in a suitable medium such that a MEKK1 protein is produced. In another embodiment, the method further includes isolating a MEKK1 protein from the medium or the host cell.

In another aspect, the invention features, a cell or purified preparation of cells which include a MEKK1 transgene, or which otherwise misexpress MEKK1. The cell preparation can consist of human or non human cells, e.g., rodent cells, e.g., mouse or rat cells, rabbit cells, or pig cells. In preferred embodiments, the cell or cells include a MEKK1 transgene, e.g., a heterologous form of a MEKK1, e.g., a gene derived from humans (in the case of a non-human cell). The MEKK1 transgene can be misexpressed, e.g., overexpressed or underexpressed. In other preferred embodiments, the cell or cells include a gene which misexpress an endogenous MEKK1, e.g., a gene the expression of which is disrupted, e.g., a knockout. Such cells can serve as a model for studying disorders which are related to mutated or misexpressed MEKK1 alleles or for use in drug screening.

In another aspect, the invention features, a human cell, e.g., a hematopoietic stem cell, transformed with nucleic acid which encodes a subject MEKK1 polypeptide.

Also provided are cells, preferably human cells, e.g., human hematopoietic or fibroblast cells, in which an endogenous MEKK1 is under the control of a regulatory sequence that does not normally control the expression of the endogenous MEKK1 gene. The expression characteristics of an endogenous gene within a cell, e.g., a cell line or microorganism, can be modified by inserting a heterologous DNA regulatory element into the genome of the cell such that the inserted regulatory element is operably linked to the endogenous MEKK1 gene. For example, an endogenous MEKK1 gene which is "transcriptionally silent," e.g., not normally expressed, or expressed only at very low levels, may be activated by inserting a regulatory element which is capable of promoting the expression of a normally expressed gene product in that cell. Techniques such as targeted homologous recombination, can be used to insert the heterologous DNA as described in, e.g., Chappel, U.S. Pat. No. 5,272,071; WO91/06667, published in May 16, 1991.

Transgenic Animals

The invention provides non-human transgenic animals. Such animals are useful for studying the function and/or activity of a MEKK1 protein and for identifying and/or evaluating modulators of MEKK1 activity. As used herein, a "transgenic animal" is a non-human animal, preferably a mammal, more preferably a rodent such as a rat or mouse, in which one or more of the cells of the animal includes a transgene. Other examples of transgenic animals include non-human primates, sheep, dogs, cows, goats, chickens, amphibians, and the like. A transgene is exogenous DNA or a rearrangement, e.g., a deletion of endogenous chromosomal DNA, which preferably is integrated into or occurs in the genome of the cells of a transgenic animal. A transgene can direct the expression of an encoded gene product in one or more cell types or tissues of the transgenic animal, other transgenes, e.g., a knockout, reduce expression. Thus, a transgenic animal can be one in which an endogenous MEKK1 gene has been altered by, e.g., by homologous recombination between the endogenous gene and an exogenous DNA molecule introduced into a cell of the animal, e.g., an embryonic cell of the animal, prior to development of the animal.

Intronic sequences and polyadenylation signals can also be included in the transgene to increase the efficiency of expression of the transgene. A tissue-specific regulatory sequence(s) can be operably linked to a transgene of the invention to direct expression of a MEKK1 protein to particular cells. A transgenic founder animal can be identified based upon the presence of a MEKK1 transgene in its genome and/or expression of MEKK1 mRNA in tissues or cells of the animals. A transgenic founder animal can then be used to breed additional animals carrying the transgene. Moreover, transgenic animals carrying a transgene encoding a MEKK1 protein can further be bred to other transgenic animals carrying other transgenes.

MEKK1 proteins or polypeptides can be expressed in transgenic animals or plants, e.g., a nucleic acid encoding the protein or polypeptide can be introduced into the genome of an animal. In preferred embodiments the nucleic acid is placed under the control of a tissue specific promoter, e.g., a milk or egg specific promoter, and recovered from the milk or eggs produced by the animal. Suitable animals are mice, pigs, cows, goats, and sheep.

The invention also includes a population of cells from a transgenic animal, e.g., as discussed below.

Uses

The nucleic acid molecules, proteins, protein homologues, and antibodies described herein can be used in one or more of the following methods: a) screening assays; b) predictive medicine (e.g., diagnostic assays, prognostic assays, monitoring clinical trials, and pharmacogenetics); and c) methods of treatment (e.g., therapeutic and prophylactic); and d) methods of identifying other important small molecules and potential drug targets within MEKK1 signaling pathway. The isolated nucleic acid molecules of the invention can be used, for example, to express a MEKK1 protein (e.g., via a recombinant expression vector in a host cell in gene therapy applications), to detect a MEKK1 mRNA (e.g., in a biological sample) or a genetic alteration in a MEKK1 gene, and to modulate MEKK1 activity, as described further below. The MEKK1 proteins can be used to treat disorders characterized by insufficient or excessive production of a MEKK1 substrate or production of MEKK1 inhibitors. In addition, the MEKK1 proteins can be used to screen for naturally occurring MEKK1 substrates, to screen for small molecules, drugs or compounds which regulate or modulate MEKK1 activity, as well as to treat disorders characterized by insufficient or excessive production of MEKK1 protein or production of MEKK1 protein forms which have decreased, aberrant or unwanted activity compared to MEKK1 wild type protein (e.g., a proliferative disorder). Moreover, the anti-MEKK1 antibodies of the invention can be used to detect and isolate MEKK1 proteins, regulate the bioavailability of MEKK1 proteins, and modulate MEKK1 activity.

A method of evaluating a compound for the ability to interact with, e.g., bind, a subject MEKK1 polypeptide is provided. The method includes: contacting the compound with the subject MEKK1 polypeptide; and evaluating ability of the compound to interact with, e.g., to bind or form a complex with the subject MEKK1 polypeptide. This method can be performed in vitro, e.g., in a cell free system, or in vivo, e.g., in a two-hybrid interaction trap assay. This method can be used to identify naturally occurring molecules which interact with subject MEKK1 polypeptide. It can also be used to find natural or synthetic inhibitors of subject MEKK1 polypeptide. Screening methods are discussed in more detail below.

Screening Assays:

The invention provides methods (also referred to herein as "screening assays") for identifying modulators, i.e., candidate or test compounds or agents (e.g., proteins, peptides, peptidomimetics, peptoids, small molecules or other drugs) which bind to MEKK1 proteins, have a stimulatory or inhibitory effect on, for example, MEKK1 expression or MEKK1 activity, or have a stimulatory or inhibitory effect on, for example, the expression or activity of a MEKK1 substrate. Compounds thus identified can be used to modulate the activity of target gene products (e.g., MEKK1 genes) in a therapeutic protocol, to elaborate the biological function of the target gene product, or to identify compounds that disrupt normal target gene interactions.

In one embodiment, the invention provides assays for screening candidate or test compounds which are substrates of a MEKK1 protein or polypeptide or a biologically active portion thereof. In another embodiment, the invention provides assays for screening candidate or test compounds which bind to or modulate the activity of a MEKK1 protein or polypeptide or a biologically active portion thereof.

The test compounds of the present invention can be obtained using any of the numerous approaches in combinatorial library methods known in the art, including: biological libraries; peptoid libraries (libraries of molecules having the functionalities of peptides, but with a novel, non-peptide backbone which are resistant to enzymatic degradation but which nevertheless remain bioactive)(see, e.g., Zuckermann, *J. Med. Chem.* 1994, 37: 2678–85 (1994)); spatially addressable parallel solid phase or solution phase libraries; synthetic library methods requiring deconvolution; the 'one-bead one-compound' library method; and synthetic library methods using affinity chromatography selection. The biological library and peptoid library approaches are limited to peptide libraries, while the other four approaches are applicable to peptide, non-peptide oligomer or small molecule libraries of compounds (Lam, K. S. (1997) *Anticancer Drug Des.* 12:145).

Examples of methods for the synthesis of molecular libraries can be found in the art, for example in: DeWitt et al., *Proc. Natl. Acad. Sci. U.S.A.* 90:6909 (1993); Erb et al., *Proc. Natl. Acad. Sci. USA* 91:11422 (1994); Zuckermann et al., *J. Med. Chem.* 37:2678 (1994); Cho et al., *Science* 261:1303; Carrell et al., *Angew. Chem. Int. Ed. Engl.* 33:2059 (1994); Carell et al., *Angew. Chem. Int. Ed. Engl.* 33:2061 (1994); and in Gallop et al., *J. Med. Chem.* 37:1233 (1994).

Libraries of compounds may be presented in solution (e.g., Houghten (1992) *Biotechniques* 13:412–421), or on beads (Lam (1991) *Nature* 354:82–84), chips (Fodor (1993) *Nature* 364:555–556), bacteria (Ladner U.S. Pat. No. 5,223, 409), spores (Ladner U.S. patent '409), plasmids (Cull et al., *Proc Natl Acad Sci USA* 89:1865–1869 (1992)) or on phage (Scott et al., *Science* 249:386390 (1990)); (Devlin, *Science* 249:404–406 (1990)); (Cwirla et al., *Proc. Natl. Acad. Sci.* 87:6378–6382 (1990)); (Felici, *J. Mol. Biol.* 222:301–310 (1991)); (Ladner supra.).

In one embodiment, an assay is a cell-based assay in which a cell which expresses a MEKK1 protein or biologically active portion thereof is contacted with a test compound, and the ability of the test compound to modulate MEKK1 activity is determined. Determining the ability of the test compound to modulate MEKK1 activity can be accomplished by monitoring, for example, binding of MEKK1 to ATP, IKK, JNK-1, JNK-2, and JNK-3. The cell, for example, can be of mammalian origin, e.g., a human HELA and Jurkat cell. The ability of the test compound to modulate MEKK1 binding to a compound, e.g., a MEKK1 substrate, or to bind to MEKK1 can also be evaluated. This can be accomplished, for example, by coupling the compound, e.g., the substrate, with a radioisotope or enzymatic label such that binding of the compound, e.g., the substrate, to MEKK1 can be determined by detecting the labeled compound, e.g., substrate, in a complex. Alternatively, MEKK1 could be coupled with a radioisotope or enzymatic label to monitor the ability of a test compound to modulate MEKK1 binding to a MEKK1 substrate in a complex. For example, compounds (e.g., MEKK1 substrates) can be labeled with $^{125}I$, $^{35}S$, $^{14}C$, or $^{3}H$, either directly or indirectly, and the radioisotope detected by direct counting of radioemmission or by scintillation counting. Alternatively, compounds can be enzymatically labeled with, for example, horseradish peroxidase, alkaline phosphatase, or luciferase, and the enzymatic label detected by determination of conversion of an appropriate substrate to product.

The ability of a compound (e.g., a MEKK1 substrate) to interact with MEKK1 with or without the labeling of any of the interactants can be evaluated. For example, a microphysiometer can be used to detect the interaction of a compound with MEKK1 without the labeling of either the compound or the MEKK1. McConnell et al., *Science* 257:1906–1912 (1992). As used herein, a "microphysiometer" (e.g., Cytosensor) is an analytical instrument that measures the rate at which a cell acidifies its environment using a light-addressable potentiometric sensor (LAPS). Changes in this acidification rate can be used as an indicator of the interaction between a compound and MEKK1.

In yet another embodiment, a cell-free assay is provided in which a MEKK1 protein or biologically active portion thereof is contacted with a test compound and the ability of the test compound to bind to the MEKK1 protein or biologically active portion thereof is evaluated. Preferred biologically active portions of the MEKK1 proteins to be used in assays of the present invention include fragments which participate in interactions with non-MEKK1 molecules, e.g., fragments with high surface probability scores.

Soluble and/or membrane-bound forms of isolated proteins (e.g., MEKK1 proteins or biologically active portions thereof) can be used in the cell-free assays of the invention. When membrane-bound forms of the protein are used, it may be desirable to utilize a solubilizing agent. Examples of such solubilizing agents include non-ionic detergents such as n-octylglucoside, n-dodecylglucoside, n-dodecylmaltoside, octanoyl-N-methylglucamide, decanoyl-N-methylglucamide, Triton® X-100, Triton® X-114, Thesit®, Isotridecypoly(ethylene glycol ether)$_n$, 3[(3 cholamidopropyl)dimethylamminio]-1-propane sulfonate (CHAPS), 3[(3-cholamidopropyl)dimethylamminio]-2-hydroxy-1-propane sulfonate (CHAPSO), or N-dodecyl=N,N-dimethyl-3-ammonio-1-propane sulfonate.

Cell-free assays involve preparing a reaction mixture of the target gene protein and the test compound under conditions and for a time sufficient to allow the two components to interact and bind, thus forming a complex that can be removed and/or detected.

The biological interaction between two molecules can also be detected, e.g., using fluorescence energy transfer (FET) (see, for example, Lakowicz et al., U.S. Pat. No. 5,631,169; Stavrianopoulos et al., U.S. Pat. No. 4,868,103) scintillation proximity assay (SPA) and homogeneous time resolved fluorescence (HTRF). A fluorophore label on the first, 'donor' molecule is selected such that its emitted fluorescent energy will be absorbed by a fluorescent label on a second, 'acceptor' molecule, which in turn is able to fluoresce due to the absorbed energy. Alternately, the 'donor' protein molecule may simply utilize the natural fluorescent energy of tryptophan residues. Labels are chosen that emit different wavelengths of light, such that the 'acceptor' molecule label may be differentiated from that of the 'donor'. Since the efficiency of energy transfer between the labels is related to the distance separating the molecules, the spatial relationship between the molecules can be assessed. In a situation in which binding occurs between the molecules, the fluorescent emission of the 'acceptor' molecule label in the assay should be maximal. An FET binding event can be conveniently measured through standard fluorometric detection means well known in the art (e.g., using a fluorimeter).

In another embodiment, determining the ability of the MEKK1 protein to bind to a target molecule can be accomplished using real-time Biomolecular Interaction Analysis (BIA) (see, e.g., Sjolander, S. and Urbaniczky, C. (1991) Anal. Chem. 63:23382345 and Szabo et al., *Curr. Opin. Struct. Biol.* 5:699–705 (1995)). "Surface plasmon resonance" or "BIA" detects biospecific interactions in real time, without labeling any of the interactants (e.g., BIAcore). Changes in the mass at the binding surface (indicative of a binding event) result in alterations of the refractive index of light near the surface (the optical phenomenon of surface plasmon resonance (SPR)), resulting in a detectable signal which can be used as an indication of real-time reactions between biological molecules.

In one embodiment, the target gene product or the test substance is anchored onto a solid phase. The target gene product/test compound complexes anchored on the solid phase can be detected at the end of the reaction. Preferably, the target gene product can be anchored onto a solid surface, and the test compound, (which is not anchored), can be labeled, either directly or indirectly, with detectable labels discussed herein.

It may be desirable to immobilize either MEKK1 or an anti-MEKK1 antibody or its target molecule to facilitate separation of complexed from uncomplexed forms of one or both of the proteins, as well as to accommodate automation of the assay. Binding of a test compound to a MEKK1 protein, or interaction of a MEKK1 protein with a target molecule in the presence and absence of a candidate compound, can be accomplished in any vessel suitable for containing the reactants. Examples of such vessels include microtiter plates, test tubes, and micro-centrifuge tubes. In one embodiment, a fusion protein can be provided which adds a domain that allows one or both of the proteins to be bound to a matrix. For example, glutathione-S-transferase/MEKK1 fusion proteins or glutathione-S-transferase/target fusion proteins can be adsorbed onto glutathione sepharose beads (Sigma Chemical, St. Louis, Mo.) or glutathione derivatized microtiter plates, which are then combined with the test compound or the test compound and either the non-adsorbed target protein or MEKK1 protein, and the mixture incubated under conditions conducive to complex formation (e.g., at physiological conditions for salt and pH). Following incubation, the beads or microtiter plate wells are washed to remove any unbound components, the matrix immobilized in the case of beads, complex determined either directly or indirectly, for example, as described above. Alternatively, the complexes can be dissociated from the matrix, and the level of MEKK1 binding or activity determined using standard techniques.

Other techniques for immobilizing either a MEKK1 protein or a target molecule on matrices include using conjugation of biotin and streptavidin. On Biotinylated MEKK1 protein or target molecules can be prepared from biotin-NHS (N-hydroxy-succinimide) using techniques known in the art (e.g., biotinylation kit, Pierce Chemicals, Rockford, Ill.), and immobilized in the wells of streptavidin-coated 96 well plates (Pierce Chemical).

In order to conduct the assay, the non-immobilized component is added to the coated surface containing the anchored component. After the reaction is complete, unreacted components are removed (e.g., by washing) under conditions such that any complexes formed will remain immobilized on the solid surface. The detection of complexes anchored on the solid surface can be accomplished in a number of ways. Where the previously non-immobilized component is pre-labeled, the detection of label immobilized on the surface indicates that complexes were formed. Where the previously non-immobilized component is not pre-labeled, an indirect label can be used to detect complexes anchored on the surface; e.g., using a labeled antibody specific for the immobilized component (the antibody, in turn, can be directly labeled or indirectly labeled with, e.g., a labeled anti-Ig antibody).

In one embodiment, this assay is performed utilizing antibodies reactive with MEKK1 protein or target molecules but which do not interfere with binding of the MEKK1 protein to its target molecule. Such antibodies can be derivatized to the wells of the plate, and unbound target or MEKK1 protein trapped in the wells by antibody conjugation. Methods for detecting such complexes, in addition to those described above for the GST-immobilized complexes, include immunodetection of complexes using antibodies reactive with the MEKK1 protein or target molecule, as well as enzyme-linked assays which rely on detecting an enzymatic activity associated with the MEKK1 protein or target molecule.

Alternatively, cell free assays can be conducted in a liquid phase. In such an assay, the reaction products are separated from unreacted components, by any of a number of standard techniques, including but not limited to: differential centrifugation (see, for example, Rivas, G., and Minton, A. P., *Trends Biochem Sci* 1993 August; 18(8):284–7); chromatography (gel filtration chromatography, ion-exchange chromatography); electrophoresis (see, e.g., Ausubel et al., eds. *Current Protocols in Molecular Biology*, J. Wiley: New York (1999).); and immunoprecipitation (see, for example, Ausubel et al., eds. *Current Protocols in Molecular Biology*, J. Wiley: New York (1999)). Such resins and chromatographic techniques are known to one skilled in the art (see, e.g., Heegaard, N. H., *J Mol Recognit* 1998 Winter; 11(1–6): 141–8; Hage, D. S., and Tweed, S. A. *J Chromatogr B Biomed Sci Appl* 1997 Oct. 10; 699(1–2):499–525). Further, fluorescence energy transfer may also be conveniently utilized, as described herein, to detect binding without further purification of the complex from solution.

In a preferred embodiment, the assay includes contacting the MEKK1 protein or biologically active portion thereof with a known compound which binds MEKK1 to form an assay mixture, contacting the assay mixture with a test compound, and determining the ability of the test compound to interact with a MEKK1 protein, wherein determining the ability of the test compound to interact with a MEKK1 protein includes determining the ability of the test compound to preferentially bind to MEKK1 or biologically active portion thereof, or to modulate the activity of a target molecule, as compared to the known compound.

The target gene products of the invention can interact in vivo with one or more cellular or extracellular macromolecules, such as proteins. For the purposes of this discussion, such cellular and extracellular macromolecules are referred to herein as "binding partners." Compounds that disrupt such interactions can be useful in regulating the activity of the target gene product. Such compounds can include, but are not limited to, molecules such as antibodies, peptides, and small molecules. The preferred target genes/products for use in this embodiment are the MEKK1 genes herein identified. In an alternative embodiment, the invention provides methods for determining the ability of the test compound to modulate the activity of a MEKK1 protein through modulation of the activity of a downstream effector of a MEKK1 target molecule. For example, the activity of the effector molecule on an appropriate target can be determined, or the binding of the effector to an appropriate target can be determined, as previously described.

To identify compounds that interfere with the interaction between the target gene product and its cellular or extracellular binding partner(s), a reaction mixture containing the target gene product and the binding partner is prepared, under conditions and for a time sufficient, to allow the two products to form complex. In order to test an inhibitory agent, the reaction mixture is provided in the presence and absence of the test compound. The test compound can be initially included in the reaction mixture, or can be added at a time subsequent to the addition of the target gene and its cellular or extracellular binding partner. Control reaction mixtures are incubated without the test compound or with a placebo. The formation of any complexes between the target gene product and the cellular or extracellular binding partner is then detected. The formation of a complex in the control reaction, but not in the reaction mixture containing the test compound, indicates that the compound interferes with the interaction of the target gene product and the interactive binding partner. Additionally, complex formation within reaction mixtures containing the test compound and normal target gene product can also be compared to complex formation within reaction mixtures containing the test compound and mutant target gene product. This comparison can be important in those cases wherein it is desirable to identify compounds that disrupt interactions of mutant but not normal target gene products.

These assays can be conducted in a heterogeneous or homogeneous format. Heterogeneous assays involve anchoring either the target gene product or the binding partner onto a solid phase, and detecting complexes anchored on the solid phase at the end of the reaction. In homogeneous assays, the entire reaction is carried out in a liquid phase. In either approach, the order of addition of reactants can be varied to obtain different information about the compounds being tested. For example, test compounds that interfere with the interaction between the target gene products and the binding partners, e.g., by competition, can be identified by conducting the reaction in the presence of the test substance. Alternatively, test compounds that disrupt preformed complexes, e.g., compounds with higher binding constants that displace one of the components from the complex, can be tested by adding the test compound to the reaction mixture after complexes have been formed. The various formats are briefly described below.

In a heterogeneous assay system, either the target gene product or the interactive cellular or extracellular binding partner, is anchored onto a solid surface (e.g., a microtiter plate), while the non-anchored species is labeled, either directly or indirectly. The anchored species can be immobilized by non-covalent or covalent attachments. Alternatively, an immobilized antibody specific for the species to be anchored can be used to anchor the species to the solid surface.

In order to conduct the assay, the partner of the immobilized species is exposed to the coated surface with or without the test compound. After the reaction is complete, unreacted components are removed (e.g., by washing) and any complexes formed will remain immobilized on the solid surface. Where the non-immobilized species is pre-labeled, the detection of label immobilized on the surface indicates that complexes were formed. Where the non-immobilized species is not pre-labeled, an indirect label can be used to detect complexes anchored on the surface; e.g., using a labeled antibody specific for the initially non-immobilized species (the antibody, in turn, can be directly labeled or indirectly labeled with, e.g., a labeled anti-Ig antibody). Depending upon the order of addition of reaction components, test compounds that inhibit complex formation or that disrupt preformed complexes can be detected.

Alternatively, the reaction can be conducted in a liquid phase in the presence or absence of the test compound, the reaction products separated from unreacted components, and complexes detected; e.g., using an immobilized antibody specific for one of the binding components to anchor any complexes formed in solution, and a labeled antibody specific for the other partner to detect anchored complexes. Again, depending upon the order of addition of reactants to the liquid phase, test compounds that inhibit complex or that disrupt preformed complexes can be identified.

In an alternate embodiment of the invention, a homogeneous assay can be used. For example, a preformed complex of the target gene product and the interactive cellular or extracellular binding partner product is prepared in that either the target gene products or their binding partners are labeled, but the signal generated by the label is quenched due to complex formation (see, e.g., U.S. Pat. No. 4,109,496 that utilizes this approach for immunoassays). The addition of a test substance that competes with and displaces one of the species from the preformed complex will result in the generation of a signal above background. In this way, test substances that disrupt target gene product-binding partner interaction can be identified.

In yet another aspect, the MEKK1 proteins can be used as "bait proteins" in a two-hybrid assay or three-hybrid assay (see, e.g., U.S. Pat. No. 5,283,317; Zervos et al., *Cell* 72:223–232 (1993); Madura et al., *J. Biol. Chem.* 268:1204612054 (1993); Bartel et al., *Biotechniques* 14:920–924 (1993); Iwabuchi et al., *Oncogene* 8:1693–1696 (1993); and Brent WO94/10300), to identify other proteins, which bind to or interact with MEKK1 ("MEKK1-binding proteins" or "MEKK1-bp") and are involved in MEKK1 activity. Such MEKK1-bps can be activators or inhibitors of signals by the MEKK1 proteins or MEKK1 targets as, for example, downstream elements of a MEKK1-mediated signaling pathway.

The two-hybrid system is based on the modular nature of most transcription factors, which consist of separable DNA-binding and activation domains. Briefly, the assay utilizes two different DNA constructs. In one construct, the gene that codes for a MEKK1 protein is fused to a gene encoding the DNA binding domain of a known transcription factor (e.g., GAL-4). In the other construct, a DNA sequence, from a library of DNA sequences, that encodes an unidentified protein ("prey" or "sample") is fused to a gene that codes for the activation domain of the known transcription factor. (Alternatively, the MEKK1 protein can be the fused to the activator domain.) If the "bait" and the "prey" proteins are able to interact, in vivo, forming a MEKK1-dependent complex, the DNA-binding and activation domains of the transcription factor are brought into close proximity. This proximity allows transcription of a reporter gene (e.g., LacZ) which is operably linked to a transcriptional regulatory site responsive to the transcription factor. Expression of the reporter gene can be detected and cell colonies containing the functional transcription factor can be isolated and used to obtain the cloned gene which encodes the protein which interacts with the MEKK1 protein.

In another embodiment, modulators of MEKK1 expression are identified. For example, a cell or cell free mixture is contacted with a candidate compound and the expression of MEKK1 mRNA or protein evaluated relative to the level of expression of MEKK1 mRNA or protein in the absence of the candidate compound. When expression of MEKK1 mRNA or protein is greater in the presence of the candidate compound than in its absence, the candidate compound is identified as a stimulator of MEKK1 mRNA or protein expression. Alternatively, when expression of MEKK1 mRNA or protein is less (statistically significantly less) in the presence of the candidate compound than in its absence, the candidate compound is identified as an inhibitor of MEKK1 mRNA or protein expression. The level of MEKK1 mRNA or protein expression can be determined by methods described herein for detecting MEKK1 mRNA or protein.

In another aspect, the invention pertains to a combination of two or more of the assays described herein. For example, a modulating agent can be identified using a cell-based or a cell free assay, and the ability of the agent to modulate the activity of a MEKK1 protein can be confirmed in vivo.

This invention further pertains to novel agents identified by the above-described screening assays. Accordingly, it is within the scope of this invention to further use an agent identified as described herein (e.g., a 9 MEKK1 modulating agent, an antisense MEKK1 nucleic acid molecule, a MEKK1-specific antibody, or a MEKK1-binding partner) in an appropriate animal model to determine the efficacy, toxicity, side effects, or mechanism of action, of treatment with such an agent. Furthermore, novel agents identified by the above-described screening assays can be used for treatments as described herein.

Detection Assays

Portions or fragments of the nucleic acid sequences identified herein can be used as polynucleotide reagents. For example, these sequences can be used to: (i) map their respective genes on a chromosome e.g., to locate gene regions associated with genetic disease or to associate MEKK1 with a disease; (ii) identify an individual from a minute biological sample (tissue typing); and (iii) aid in forensic identification of a biological sample. These applications are described in the subsections below.

Chromosome Mapping

The MEKK1 nucleotide sequences or portions thereof can be used to map the location of the MEKK1 genes on a chromosome. This process is called chromosome mapping. Chromosome mapping is useful in correlating the MEKK1 sequences with genes associated with disease.

Briefly, MEKK1 genes can be mapped to chromosomes by preparing PCR primers (preferably 15–25 bp in length) from the MEKK1 nucleotide sequences. These primers can then be used for PCR screening of somatic cell hybrids containing individual human chromosomes. Only those hybrids containing the human gene corresponding to the MEKK1 sequences will yield an amplified fragment.

A panel of somatic cell hybrids in which each cell line contains either a single human chromosome or a small number of human chromosomes, and a full set of mouse chromosomes, can allow easy mapping of individual genes to specific human chromosomes. (D'Eustachio et al., *Science* 220:919–924 (1983)).

Other mapping strategies e.g., in situ hybridization (described in Fan, *Proc. Natl. Acad. Sci. USA*, 87:6223–27 (1990)), pre-screening with labeled flow-sorted chromosomes, and pre-selection by hybridization to chromosome specific cDNA libraries can be used to map MEKK1 to a chromosomal location.

Fluorescence in situ hybridization (FISH) of a DNA sequence to a metaphase chromosomal spread can further be used to provide a precise chromosomal location in one step. The FISH technique can be used with a DNA sequence as short as 500 or 600 bases. However, clones larger than 1,000 bases have a higher likelihood of binding to a unique chromosomal location with sufficient signal intensity for simple detection. Preferably 1,000 bases, and more preferably 2,000 bases will suffice to get good results at a reasonable amount of time. For a review of this technique, see Verma et al., *Human Chromosomes: A Manual of Basic Techniques* (Pergamon Press, New York (1988)).

Reagents for chromosome mapping can be used individually to mark a single chromosome or a single site on that chromosome, or panels of reagents can be used for marking multiple sites and/or multiple chromosomes. Reagents corresponding to noncoding regions of the genes actually are preferred for mapping purposes. Coding sequences are more likely to be conserved within gene families, thus increasing the chance of cross hybridizations during chromosomal mapping.

Once a sequence has been mapped to a precise chromosomal location, the physical position of the sequence on the chromosome can be correlated with genetic map data. (Such data are found, for example, in V. McKusick, Mendelian Inheritance in Man, available on-line through Johns Hopkins University Welch Medical Library). The relationship between a gene and a disease, mapped to the same chromosomal region, can then be identified through linkage analysis (co-inheritance of physically adjacent genes), described in, for example, Egeland et al., *Nature*, 325:783–787 (1987).

Moreover, differences in the DNA sequences between individuals affected and unaffected with a disease associated with the MEKK1 gene, can be determined. If a mutation is observed in some or all of the affected individuals but not in any unaffected individuals, then the mutation is likely to be the causative agent of the particular disease. Comparison of affected and unaffected individuals generally involves first looking for structural alterations in the chromosomes, such as deletions or translocations that are visible from chromosome spreads or detectable using PCR based on that DNA sequence. Ultimately, complete sequencing of genes from several individuals can be performed to confirm the presence of a mutation and to distinguish mutations from polymorphisms.

Tissue Typing

MEKK1 sequences can be used to identify individuals from biological samples using, e.g., restriction fragment length polymorphism (RFLP). In this technique, an individual's genomic DNA is digested with one or more restriction enzymes, the fragments separated, e.g., in a Southern blot, and probed to yield bands for identification. The sequences of the present invention are useful as additional DNA markers for RFLP (described in U.S. Pat. No. 5,272,057).

Furthermore, the sequences of the present invention can also be used to determine the actual base-by-base DNA sequence of selected portions of an individual's genome. Thus, the MEKK1 nucleotide sequences described herein can be used to prepare two PCR primers from the 5' and 3' ends of the sequences. These primers can then be used to amplify an individual's DNA and subsequently sequence it. Panels of corresponding DNA sequences from individuals, prepared in this manner, can provide unique individual identifications, as each individual will have a unique set of such DNA sequences due to allelic differences.

Allelic variation occurs to some degree in the coding regions of these sequences, and to a greater degree in the noncoding regions. Each of the sequences described herein can, to some degree, be used as a standard against which DNA from an individual can be compared for identification purposes. Because greater numbers of polymorphisms occur in the noncoding regions, fewer sequences are necessary to differentiate individuals. The noncoding sequences of SEQ ID NO:1 can provide positive individual identification with a panel of perhaps 10 to 1,000 primers which each yield a noncoding amplified sequence of 100 bases. If predicted coding sequences, such as those in nucleotide 7 to nucleotide 4545 of SEQ ID NO:1 are used, a more appropriate number of primers for positive individual identification would be 500–2,000.

If a panel of reagents from MEKK1 nucleotide sequences described herein is used to generate a unique identification database for an individual, those same reagents can later be used to identify tissue from that individual. Using the unique identification database, positive identification of the individual, living or dead, can be made from extremely small tissue samples.

Use of Partial MEKK1 Sequences in Forensic Biology

DNA-based identification techniques can also be used in forensic biology. To make such an identification, PCR technology can be used to amplify DNA sequences taken from very small biological samples such as tissues, e.g., hair or skin, or body fluids, e.g., blood, saliva, or semen found at a crime scene. The amplified sequence can then be compared to a standard, thereby allowing identification of the origin of the biological sample.

The sequences of the present invention can be used to provide polynucleotide reagents, e.g., PCR primers, targeted to specific loci in the −4 human genome, which can enhance the reliability of DNA-based forensic identifications by, for example, providing another "identification marker" (i.e., another DNA sequence that is unique to a particular individual). As mentioned above, actual base sequence information can be used for identification as an accurate alternative to patterns formed by restriction enzyme generated fragments. Sequences targeted to noncoding regions of SEQ ID NO:1 (e.g., fragments derived from the noncoding regions of SEQ ID NO:1 having a length of at least 20 bases, preferably at least 30 bases) are particularly appropriate for this use.

The MEKK1 nucleotide sequences described herein can further be used to provide polynucleotide reagents, e.g., labeled or labelable probes which can be used in, for example, an in situ hybridization technique, to identify a specific tissue. This can be very useful in cases where a forensic pathologist is presented with a tissue of unknown origin. Panels of such MEKK1 probes can be used to identify tissue by species and/or by organ type.

In a similar fashion, these reagents, e.g., MEKK1 primers or probes can be used to screen tissue culture for contamination (i.e., screen for the presence of a mixture of different types of cells in a culture).

Predictive Medicine

The present invention also pertains to the field of predictive medicine in which diagnostic assays, prognostic assays, and monitoring clinical trials are used for prognostic (predictive) purposes to thereby treat an individual.

Generally, the invention provides, a method of determining if a subject is at risk for a disorder related to a lesion in or the misexpression of a gene which encodes MEKK1 or a signal transduction protein or a cell adhesion protein.

The method includes one or more of the following:

detecting, in a tissue of the subject, the presence or absence of a mutation which affects the expression of the MEKK1 gene, or detecting the presence or absence of a mutation in a region which controls the expression of the gene, e.g., a mutation in the 5' control region;

detecting, in a tissue of the subject, the presence or absence of a mutation which alters the structure of the MEKK1 gene;

detecting, in a tissue of the subject, the misexpression of the MEKK1 gene, at the mRNA level, e.g., detecting a non-wild type level of a mRNA;

detecting, in a tissue of the subject, the misexpression of the gene, at the protein level, e.g., detecting a non-wild type level of a MEKK1 polypeptide.

In preferred embodiments the method includes: ascertaining the existence of at least one of: a deletion of one or more nucleotides from the MEKK1 gene; an insertion of one or more nucleotides into the gene, a point mutation, e.g., a substitution of one or more nucleotides of the gene, a gross chromosomal rearrangement of the gene, e.g., a translocation, inversion, or deletion.

For example, detecting the genetic lesion can include: (i) providing a probe/primer including an oligonucleotide containing a region of nucleotide sequence which hybridizes to a sense or antisense sequence from SEQ ID NO:1 or nucleotide 7 to nucleotide 4545 of SEQ ID NO:1, or naturally occurring mutants thereof, or 5' or 3' flanking sequences naturally associated with the MEKK1 gene; (ii) exposing the probe/primer to nucleic acid of the tissue; and detecting, by hybridization, e.g., in situ hybridization, of the probe/primer to the nucleic acid, the presence or absence of the genetic lesion.

In preferred embodiments detecting the misexpression includes ascertaining the existence of at least one of: an alteration in the level of a messenger RNA transcript of the MEKK1 gene; the presence of a non-wild type splicing pattern of a messenger RNA transcript of the gene; or a non-wild type level of MEKK1.

Methods of the invention can be used prenatally or to determine if a subject's offspring will be at risk for a disorder.

In preferred embodiments the method includes determining the structure of a MEKK1 gene, an abnormal structure being indicative of risk for the disorder.

In preferred embodiments the method includes contacting a sample form the subject with an antibody to the MEKK1 protein or a nucleic acid, which hybridizes specifically with the gene. There and other embodiments are discussed below.

Diagnostic and Prognostic Assays

The presence, level, or absence of MEKK1 protein or nucleic acid in a biological sample can be evaluated by obtaining a biological sample from a test subject and contacting the biological sample with a compound or an agent capable of detecting MEKK1 protein or nucleic acid (e.g., mRNA or genomic DNA) that encodes MEKK1 protein such that the presence of MEKK1 protein or nucleic acid is detected in the biological sample. The term "biological sample" includes tissues, cells and biological fluids isolated from a subject, as well as tissues, cells and fluids present within a subject. A preferred biological sample is serum. The level of expression of the MEKK1 gene can be measured in a number of ways, including, but not limited to: measuring the mRNA encoded by the MEKK1 genes; measuring the amount of protein encoded by the MEKK1 genes; or measuring the activity of the protein encoded by the MEKK1 genes.

The level of mRNA corresponding to the MEKK1 gene in a cell can be determined both by in situ and by in vitro formats.

The isolated mRNA can be used in hybridization or amplification assays that include, but are not limited to, Southern or Northern analyses, polymerase chain reaction analyses and probe arrays. One preferred diagnostic method for the detection of mRNA levels involves contacting the isolated mRNA with a nucleic acid molecule (probe) that can hybridize to the mRNA encoded by the gene being detected. The nucleic acid probe can be, for example, a full-length MEKK1 nucleic acid, such as the nucleic acid of SEQ ID NO:1, or the DNA insert of the plasmid deposited with ATCC as Accession Number PTA-1836, or a portion thereof, such as an oligonucleotide of at least 7, 15, 30, 50, 100, 250 or 500 nucleotides in length and sufficient to specifically hybridize under stringent conditions to MEKK1 mRNA or genomic DNA. Other suitable probes for use in the diagnostic assays are described herein.

In one format, mRNA (or cDNA) is immobilized on a surface and contacted with the probes, for example by running the isolated mRNA on an agarose gel and transferring the mRNA from the gel to a membrane, such as nitrocellulose. In an alternative format, the probes are immobilized on a surface and the mRNA (or cDNA) is contacted with the probes, for example, in a two-dimensional gene chip array. A skilled artisan can adapt known mRNA detection methods for use in detecting the level of mRNA encoded by the MEKK1 genes.

The level of mRNA in a sample that is encoded by one of MEKK1 can be evaluated with nucleic acid amplification, e.g., by rtPCR (Mullis, 1987, U.S. Pat. No. 4,683,202), ligase chain reaction (Barany, 1991, *Proc. Natl. Acad. Sci. USA* 88:189–193), self sustained sequence replication (Guatelli et al., *Proc. Natl. Acad. Sci. USA* 87:1874–1878 (1990)), transcriptional amplification system (Kwoh et al., *Proc. Natl. Acad. Sci. USA* 86:1173–1177 (1989)), Q-Beta Replicase (Lizardi et al., *Bio/Technology* 6:1197 (1988)), rolling circle replication (Lizardi et al., U.S. Pat. No. 5,854,033) or any other nucleic acid amplification method, followed by the detection of the amplified molecules using techniques known in the art. As used herein, amplification primers are defined as being a pair of nucleic acid molecules that can anneal to 5' or 3' regions of a gene (plus and minus strands, respectively, or vice-versa) and contain a short region in between. In general, amplification primers are from about 10 to 30 nucleotides in length and flank a region from about 50 to 200 nucleotides in length. Under appropriate conditions and with appropriate reagents, such primers permit the amplification of a nucleic acid molecule comprising the nucleotide sequence flanked by the primers.

For in situ methods, a cell or tissue sample can be prepared/processed and immobilized on a support, typically a glass slide, and then contacted with a probe that can hybridize to mRNA that encodes the MEKK1 gene being analyzed.

In another embodiment, the methods further contacting a control sample with a compound or agent capable of detecting MEKK1 mRNA, or genomic DNA, and comparing the presence of MEKK1 mRNA or genomic DNA in the control sample with the presence of MEKK1 mRNA or genomic DNA in the test sample.

A variety of methods can be used to determine the level of protein encoded by MEKK1. In general, these methods include contacting an agent that selectively binds to the protein, such as an antibody with a sample, to evaluate the level of protein in the sample. In a preferred embodiment, the antibody bears a detectable label. Antibodies can be polyclonal, or more preferably, monoclonal. An intact antibody, or a fragment thereof (e.g., Fab or F(ab')$_2$) can be used. The term "labeled", with regard to the probe or antibody, is intended to encompass direct labeling of the probe or antibody by coupling (i.e., physically linking) a detectable substance to the probe or antibody, as well as indirect labeling of the probe or antibody by reactivity with a detectable substance. Examples of detectable substances are provided herein.

The detection methods can be used to detect MEKK1 protein in a biological sample in vitro as well as in vivo. In vitro techniques for detection of MEKK1 protein include enzyme linked immunosorbent assays (ELISAs), immunoprecipitations, immunofluorescence, enzyme immunoassay (EIA), radioimmunoassay (RIA), and Western blot analysis. In vivo techniques for detection of MEKK1 protein include introducing into a subject a labeled anti-MEKK1 antibody. For example, the antibody can be labeled with a radioactive marker whose presence and location in a subject can be detected by standard imaging techniques.

In another embodiment, the methods further include contacting the control sample with a compound or agent capable of detecting MEKK1 protein, and comparing the presence of MEKK1 protein in the control sample with the presence of MEKK1 protein in the test sample.

The invention also includes kits for detecting the presence of MEKK1 in a biological sample. For example, the kit can include a compound or agent capable of detecting MEKK1 protein or mRNA in a biological sample; and a standard. The compound or agent can be packaged in a suitable container. The kit can further comprise instructions for using the kit to detect MEKK1 protein or nucleic acid.

For antibody-based kits, the kit can include: (1) a first antibody (e.g., attached to a solid support) which binds to a polypeptide corresponding to a marker of the invention; and, optionally, (2) a second, different antibody which binds to either the polypeptide or the first antibody and is conjugated to a detectable agent.

For oligonucleotide-based kits, the kit can include: (1) an oligonucleotide, e.g., a detectably labeled oligonucleotide, which hybridizes to a nucleic acid sequence encoding a polypeptide corresponding to a marker of the invention or (2) a pair of primers useful for amplifying a nucleic acid molecule corresponding to a marker of the invention. The kit can also includes a buffering agent, a preservative, or a protein stabilizing agent. The kit can also includes components necessary for detecting the detectable agent (e.g., an enzyme or a substrate). The kit can also contain a control sample or a series of control samples which can be assayed and compared to the test sample contained. Each component of the kit can be enclosed within an individual container and all of the various containers can be within a single package, along with instructions for interpreting the results of the assays performed using the kit.

The diagnostic methods described herein can identify subjects having, or at risk of developing, a disease or disorder associated with misexpressed or aberrant or unwanted MEKK1 expression or activity. As used herein, the term "unwanted" includes an unwanted phenomenon involved in a biological response such as pain or deregulated cell proliferation.

In one embodiment, a disease or disorder associated with aberrant or unwanted MEKK1 expression or activity is identified. A test sample is obtained from a subject and MEKK1 protein or nucleic acid (e.g., mRNA or genomic DNA) is evaluated, wherein the level, e.g., the presence or absence, of MEKK1 protein or nucleic acid is diagnostic for a subject having or at risk of developing a disease or disorder associated with aberrant or unwanted MEKK1 expression or activity. As used herein, a "test sample" refers to a biological sample obtained from a subject of interest, including a biological fluid (e.g., serum), cell sample, or tissue.

The prognostic assays described herein can be used to determine whether a subject can be administered an agent (e.g., an agonist, antagonist, peptidomimetic, protein, peptide, nucleic acid, small molecule, or other drug candidate) to treat a disease or disorder associated with aberrant or unwanted MEKK1 expression or activity. For example, such methods can be used to determine whether a subject can be effectively treated with an agent for a cell signaling or cell adhesion disorder.

The methods of the invention can also be used to detect genetic alterations in a MEKK1 gene, thereby determining if a subject with the altered gene is at risk for a disorder characterized by misregulation in MEKK1 protein activity or nucleic acid expression, such as a cell signaling or cell adhesion disorder. In preferred embodiments, the methods include detecting, in a sample from the subject, the presence or absence of a genetic alteration characterized by at least one of an alteration affecting the integrity of a gene encoding a MEKK1-protein, or the misexpression of the MEKK1 gene. For example, such genetic alterations can be detected by ascertaining the existence C) of at least one of (1) a deletion of one or more nucleotides from a MEKK1 gene; (2) an addition of one or more nucleotides to a MEKK1 gene; (3) a substitution of one or more nucleotides of a MEKK1 gene; (4) a chromosomal rearrangement of a MEKK1 gene; (5) an alteration in the level of a messenger RNA transcript of a MEKK1 gene; (6) aberrant modification of a MEKK1 gene, such as of the methylation pattern of the genomic DNA; (7) the presence of a non-wild type splicing pattern of a messenger RNA transcript of a MEKK1 gene; (8) a non-wild type level of a MEKK1-protein; (9) allelic loss of a MEKK1 gene; and (10) inappropriate post-translational modification of a MEKK1-protein.

An alteration can be detected without a probe/primer in a polymerase chain reaction, such as anchor PCR or RACE PCR, or, alternatively, in a ligation chain reaction (LCR), the latter of which can be particularly useful for detecting point mutations in the MEKK1 gene. This method can include the steps of collecting a sample of cells from a subject, isolating nucleic acid (e.g., genomic DNA, mRNA, or both) from the sample, contacting the nucleic acid sample with one or more primers which specifically hybridize to a MEKK1 gene under conditions such that hybridization and amplification of the MEKK1 gene (if present) occurs, and detecting the presence or absence of an amplification product, or detecting the size of the amplification product and comparing the length to a control sample. It is anticipated that PCR and/or LCR may be desirable to use as a preliminary amplification step in conjunction with any of the techniques used for detecting mutations described herein.

Alternative amplification methods include: self sustained sequence replication (Guatelli et al., *Proc. Natl. Acad. Sci. USA* 87:1874–1878 (1990)), transcriptional amplification system (Kwoh et al., *Proc. Natl. Acad. Sci. USA* 86:1173–1177 (1989)), Q-Beta Replicase (Lizardi et al., *Bio-Technology* 6:1197 (1988)), or other nucleic acid amplification methods, followed by the detection of the amplified molecules using techniques known to those of skill in the art.

In another embodiment, mutations in a MEKK1 gene from a sample cell can be identified by detecting alterations in restriction enzyme cleavage patterns. For example, sample and control DNA are isolated, optionally amplified, digested with one or more restriction endonucleases, and fragment length sizes are determined, e.g., by gel electrophoresis and compared. Differences in fragment length sizes between sample and control DNA indicates mutations in the sample DNA. Moreover, the use of sequence specific ribozymes (see, for example, U.S. Pat. No. 5,498,531) can be used to score for the presence of specific mutations by development or loss of a ribozyme cleavage site.

In other embodiments, genetic mutations in MEKK1 can be identified by hybridizing a sample and control nucleic acids, e.g., DNA or RNA, two dimensional arrays, e.g., chip based arrays. Such arrays include a plurality of addresses, each of which is positionally distinguishable from the other. A different probe is located at each address of the plurality. The arrays can have a high density of addresses, e.g., can contain hundreds or thousands of oligonucleotides probes (Cronin et al. *Human Mutation* 7: 244–255 (1996); Kozal et al. *Nature Medicine* 2: 753–759 (1996)). For example, genetic mutations in MEKK1 can be identified in two dimensional arrays containing light-generated DNA probes as described in Cronin, M. T. et al. supra. Briefly, a first hybridization array of probes can be used to scan through long stretches of DNA in a sample and control to identify base changes between the sequences by making linear arrays of sequential overlapping probes. This step allows the identification of point mutations. This step is followed by a second hybridization array that allows the characterization of specific mutations by using smaller, specialized probe arrays complementary to all variants or mutations detected. Each mutation array is composed of parallel probe sets, one complementary to the wild-type gene and the other complementary to the mutant gene.

In yet another embodiment, any of a variety of sequencing reactions known in the art can be used to directly sequence the MEKK1 gene and detect mutations by comparing the sequence of the sample MEKK1 with the corresponding wild-type (control) sequence. Automated sequencing procedures can be utilized when performing the diagnostic assays (*Biotechniques* 19:448 (1995)), including sequencing by mass spectrometry.

Other methods for detecting mutations in the MEKK1 gene include methods in which protection from cleavage agents is used to detect mismatched bases in RNA/RNA or RNA/DNA heteroduplexes (Myers et al., *Science* 230:1242 (1985); Cotton et al., *Proc. Natl Acad Sci USA* 85:4397 (1988); Saleeba et al., *Methods Enzymol.* 217:286–295 (1992)).

In still another embodiment, the mismatch cleavage reaction employs one or more proteins that recognize mismatched base pairs in double-stranded DNA (so called "DNA mismatch repair" enzymes) in defined systems for detecting and mapping point mutations in MEKK1 cDNAs obtained from samples of cells. For example, the mutY enzyme of *E. coli* cleaves A at G/A mismatches and the thymidine DNA glycosylase from HeLa cells cleaves T at G/T mismatches (Hsu et al., *Carcinogenesis* 15:1657–1662 (1994); U.S. Pat. No. 5,459,039).

In other embodiments, alterations in electrophoretic mobility will be used to identify mutations in MEKK1 genes. For example, single strand conformation polymorphism (SSCP) may be used to detect differences in electrophoretic mobility between mutant and wild type nucleic acids (Orita et al., *Proc Natl. Acad. Sci USA:* 86:2766 (1989), see also Cotton, *Mutat. Res.* 285:125–144 (1993); and Hayashi, *Genet. Anal. Tech. Appl.* 9:73–79 (1992)). Single-stranded DNA fragments of sample and control MEKK1 nucleic acids will be denatured and allowed to renature. The secondary structure of single-stranded nucleic acids varies according to sequence, the resulting alteration in electrophoretic mobility enables the detection of even a single base change. The DNA fragments may be labeled or detected with labeled probes. The sensitivity of the assay may be enhanced by using RNA (rather than DNA), in which the secondary structure is more sensitive to a change in sequence. In a preferred embodiment, the subject method utilizes heteroduplex analysis to separate double stranded heteroduplex molecules on the basis of changes in electrophoretic mobility (Keen et al., *Trends Genet* 7:5 (1991)).

In yet another embodiment, the movement of mutant or wild-type fragments in polyacrylamide gels containing a gradient of denaturant is assayed using denaturing gradient gel electrophoresis (DGGE) (Myers et al., *Nature* 313:495 (1985)). When DGGE is used as the method of analysis, DNA will be modified to insure that it does not completely denature, for example by adding a GC clamp of approximately 40 bp of high-melting GC-rich DNA by PCR. In a further embodiment, a temperature gradient is used in place of a denaturing gradient to identify differences in the mobility of control and sample DNA (Rosenbaum and Reissner, *Biophys Chem* 265:12753 (1987)).

Examples of other techniques for detecting point mutations include, but are not limited to, selective oligonucleotide hybridization, selective amplification, or selective primer extension (Saiki et al., *Nature* 324:163 (1986)); Saiki et al., *Proc. Natl. Acad. Sci* USA 86:6230 (1989)).

Alternatively, allele specific amplification technology which depends on selective PCR amplification may be used in conjunction with the instant invention. Oligonucleotides used as primers for specific amplification may carry the mutation of interest in the center of the molecule (so that amplification depends on differential hybridization) (Gibbs et al., *Nucleic Acids Res.* 17:2437–2448 (1989)) or at the extreme 3' end of one primer where, under appropriate conditions, mismatch can prevent, or reduce polymerase extension (Prossner, *Tibtech* 11:238 (1993)). In addition it may be desirable to introduce a novel restriction site in the region of the mutation to create cleavage-based detection (Gasparini et al., *Mol. Cell Probes* 6:1 (1992)). It is anticipated that in certain embodiments amplification may also be performed using Taq ligase for amplification (Barany, *Proc. Natl. Acad. Sci USA* 88:189 (1991)). In such cases, ligation will occur only if there is a perfect match at the 3' end of the 5' sequence making it possible to detect the presence of a known mutation at a specific site by looking for the presence or absence of amplification.

The methods described herein may be performed, for example, by utilizing pre-packaged diagnostic kits comprising at least one probe nucleic acid or antibody reagent described herein, which may be conveniently used, e.g., in clinical settings to diagnose patients exhibiting symptoms or family history of a disease or illness involving a MEKK1 gene.

Pharmaceutical Compositions

The nucleic acid and polypeptides, as well as anti-MEKK1 antibodies (also referred to herein as "active compounds") of the invention can be incorporated into pharmaceutical compositions. Such compositions typically include the nucleic acid molecule, protein, or antibody and a pharmaceutically acceptable carrier. As used herein the language "pharmaceutically acceptable carrier" includes solvents, dispersion media, coatings, antibacterial and antifungal agents, isotonic and absorption delaying agents, and the like, compatible with pharmaceutical administration. Supplementary active compounds can also be incorporated into the compositions.

A pharmaceutical composition is formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringability exists. It should be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. For the purpose of oral therapeutic administration, the active compound can be incorporated with excipients and used in the form of tablets, troches, or capsules, e.g., gelatin capsules. Oral compositions can also be prepared using a fluid carrier for use as a mouthwash. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier.

Toxicity and therapeutic efficacy of such compounds can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds which exhibit high therapeutic indeces are preferred. While compounds that exhibit toxic side effects may be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the ED50 with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the IC50 (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

As defined herein, a therapeutically effective amount of protein or polypeptide (i.e., an effective dosage) ranges from about 0.001 to 30 mg/kg body weight, preferably about 0.01 to 25 mg/kg body weight, more preferably about 0.1 to 20 mg/kg body weight, and even more preferably about 1 to 10 mg/kg, 2 to 9 mg/kg, 3 to 8 mg/kg, 4 to 7 mg/kg, or 5 to 6 mg/kg body weight. The protein or polypeptide can be administered one time per week for between about 1 to 10 weeks, preferably between 2 to 8 weeks, more preferably between about 3 to 7 weeks, and even more preferably for about 4, 5, or 6 weeks. The skilled artisan will appreciate that certain factors may influence the dosage and timing required to effectively treat a subject, including but not limited to the severity of the disease or disorder, previous treatments, the general health and/or age of the subject, and other diseases present. Moreover, treatment of a subject with a therapeutically effective amount of a protein, polypeptide, or antibody can include a single treatment or, preferably, can include a series of treatments.

For antibodies, the preferred dosage is 0.1 mg/kg of body weight (generally 10 mg/kg to 20 mg/kg). If the antibody is to act in the brain, a dosage of 50 mg/kg to 100 mg/kg is usually appropriate. Generally, partially human antibodies and fully human antibodies have a longer half-life within the human body than other antibodies. Accordingly, lower dosages and less frequent administration is often possible. Modifications such as lipidation can be used to stabilize antibodies and to enhance uptake and tissue penetration (e.g., into the brain). A method for lipidation of antibodies is described by Cruikshank et al., (J. Acquired Immune Deficiency Syndromes and Human Retrovirology 14:193 (1997)).

The present invention encompasses agents which modulate expression or activity. An agent may, for example, be a small molecule. For example, such small molecules include, but are not limited to, peptides, peptidomimetics (e.g., peptoids), amino acids, amino acid analogs, polynucleotides, polynucleotide analogs, nucleotides, nucleotide analogs, organic or inorganic compounds (i.e., including heteroorganic and organometallic compounds) having a molecular weight less than about 10,000 grams per mole, organic or inorganic compounds having a molecular weight less than about 5,000 grams per mole, organic or inorganic compounds having a molecular weight less than about 1,000 grams per mole, organic or inorganic compounds having a molecular weight less than about 500 grams per mole, and salts, esters, and other pharmaceutically acceptable forms of such compounds.

Exemplary doses include milligram or microgram amounts of the small molecule per kilogram of subject or sample weight (e.g., about 1 microgram per kilogram to about 500 milligrams per kilogram, about 100 micrograms per kilogram to about 5 milligrams per kilogram, or about 1 microgram per kilogram to about 50 micrograms per kilogram. It is furthermore understood that appropriate doses of a small molecule depend upon the potency of the small molecule with respect to the expression or activity to be modulated. When one or more of these small molecules is to be administered to an animal (e.g., a human) in order to modulate expression or activity of a polypeptide or nucleic acid of the invention, a physician, veterinarian, or researcher may, for example, prescribe a relatively low dose at first, subsequently increasing the dose until an appropriate response is obtained. In addition, it is understood that the specific dose level for any particular animal subject will depend upon a variety of factors including the activity of the specific compound employed, the age, body weight, general health, gender, and diet of the subject, the time of administration, the route of administration, the rate of excretion, any drug combination, and the degree of expression or activity to be modulated.

An antibody (or fragment thereof) may be conjugated to a therapeutic moiety such as a cytotoxin, a therapeutic agent or a radioactive metal ion. A cytotoxin or cytotoxic agent includes any agent that is detrimental to cells. Examples include taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. Therapeutic agents include, but are not limited to, antimetabolites (e.g., methotrexate, 6-mercaptopurine, 6-thioguanine, cytarabine, 5-fluorouracil decarbazine), alkylating agents (e.g., mechlorethamine, thioepa chlorambucil, melphalan, carmustine (BSNU) and lomustine (CCNU), cyclothosphamide, busulfan, dibromomannitol, streptozotocin, mitomycin C, and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine and vinblastine).

The conjugates of the invention can be used for modifying a given biological response, the drug moiety is not to be construed as limited to classical chemical therapeutic agents. For example, the drug moiety may be a protein or polypeptide possessing a desired biological activity. Such proteins may include, for example, a toxin such as abrin, ricin A, pseudomonas exotoxin, or diphtheria toxin; a protein such as tumor necrosis factor, alpha.-interferon, .beta.-interferon, nerve growth factor, platelet derived growth factor, tissue plasminogen activator; or, biological response modifiers such as, for example, lymphokines, interleukin-1 ("IL-1"), interleukin-2 ("IL-2"), interleukin-6 ("IL6"), granulocyte macrophase colony stimulating factor ("GM-CSF"), granulocyte colony stimulating factor ("G-CSF"), or other growth factors.

Alternatively, an antibody can be conjugated to a second antibody to form an antibody heteroconjugate as described by Segal in U.S. Pat. No. 4,676,980.

The nucleic acid molecules of the invention can be inserted into vectors and used as gene therapy vectors. Gene therapy vectors can be delivered to a subject by, for example, intravenous injection, local administration (see U.S. Pat. No. 5,328,470) or by stereotactic injection (see e.g., Chen et al., Proc. Natl. Acad. Sci. USA 91:3054–3057 (1994)). The pharmaceutical preparation of the gene therapy vector can include the gene therapy vector in an acceptable diluent, or can comprise a slow release matrix in which the gene delivery vehicle is imbedded. Alternatively, where the complete gene delivery vector can be produced intact from recombinant cells, e.g., retroviral vectors, the pharmaceutical preparation can include one or more cells which produce the gene delivery system.

The pharmaceutical compositions can be included in a container, pack, or dispenser together with instructions for administration.

Methods of Treatment

The present invention provides for both prophylactic and therapeutic methods of treating a subject at risk of (or susceptible to) a disorder or having a disorder associated with aberrant or unwanted MEKK1 expression or activity. With regards to both prophylactic and therapeutic methods of treatment, such treatments may be specifically tailored or modified, based on knowledge obtained from the field of pharmacogenomics. "Pharmacogenomics", as used herein, refers to the application of genomics technologies such as gene sequencing, statistical genetics, and gene expression analysis to drugs in clinical development and on the market. More specifically, the term refers the study of how a patient's genes determine his or her response to a drug (e.g., a patient's "drug response phenotype", or "drug response genotype".) Thus, another aspect of the invention provides methods for tailoring an individual's prophylactic or therapeutic treatment with either the MEKK1 molecules of the present invention or MEKK1 modulators according to that individual's drug response genotype. Pharmacogenomics allows a clinician or physician to target prophylactic or therapeutic treatments to patients who will most benefit from the treatment and to avoid treatment of patients who will experience toxic drug-related side effects.

In one aspect, the invention provides a method for preventing in a subject, a disease or condition associated with an aberrant or unwanted MEKK1 expression or activity, by administering to the subject a MEKK1 or an agent which modulates MEKK1 expression or at least one MEKK1 activity. Subjects at risk for a disease which is caused or contributed to by aberrant or unwanted MEKK1 expression or activity can be identified by, for example, any or a combination of diagnostic or prognostic assays as described herein. Administration of a prophylactic agent can occur prior to the manifestation of symptoms characteristic of the MEKK1 aberrance, such that a disease or disorder is prevented or, alternatively, delayed in its progression. Depending on the type of MEKK1 aberrance, for example, a MEKK1, agonist or MEKK1 antagonist agent can be used for treating the subject. The appropriate agent can be determined based on screening assays described herein.

It is possible that some MEKK1 disorders can be caused, at least in part, by an abnormal level of gene product, or by the presence of a gene product exhibiting abnormal activity. As such, the reduction in the level and/or activity of such gene products would bring about the amelioration of disorder symptoms.

The MEKK1 molecules can act as novel diagnostic targets and therapeutic agents for controlling one or more of cellular proliferative and/or differentiative disorders as described above, disorders associated with bone metabolism, immune disorders, hematopoietic disorders, cardiovascular disorders, liver disorders, viral diseases, pain or metabolic disorders.

The MEKK1 nucleic acid and protein of the invention can be used to treat and/or diagnose a variety of medical disorders that is subject to regulation or cure by manipulating a signal transduction pathway in a cell involved in the disorder. Examples of disorders or diseases include, but are not limited to, disorders that result from aberrant cell growth or aberrant production of secreted cellular products. As used herein, "aberrant cell growth" means any disease or disorder in which an abnormal amount of cell growth is observed. "Aberrant production of secreted cellular products" means any disease or disorder in which an abnormal amount of secreted cellular products is observed. Therefore, diseases involving aberrant cell growth and aberrant production of secreted cellular products are selected from the group consisting of hyperplasia, neoplasia, and cancer, as well as degenerative diseases, such a neurodegenerative diseases, autoimmune diseases, inflammatory responses, and allergic responses. By "inhibits aberrant cell growth" means any decrease in cell number or size, including, without limitation, the decrease in cell number, a decrease on the rate of cell division, an increase in the rate of cell death, and a decrease in cell size. Standard methods for measuring cell growth include standard apoptosis assays (e.g., TUNEL assays, DNA fragmentation, trypan blue exclusion) and cell proliferation assays (e.g., $^3$H-thymidine incorporation).

Preferred cancers subject to treatment using a method of the present invention include, but are not limited to, small cell carcinomas, non-small cell lung carcinomas with overexpressed EGF receptors, breast cancers with overexpressed EGF or Neu receptors, tumors having overexpressed growth factor receptors of established autocrine loops and tumors having overexpressed growth factor receptors of established paracrine loops. According to the present invention, the term "treatment" means the regulation of the progression of a medical disorder or the complete removal of a medical disorder (e.g., a cure). Treatment of a medical disorder can comprise regulating the signal transduction activity of a cell in such a manner that a cell involved in the medical disorder no longer responds to extracellular stimuli (e.g., growth factors or cytokines), or the killing of a cell involved in the medical disorder through cellular apoptosis., The present invention relates to a method of inducing and/or maintaining a differentiated state, enhancing survival, and/or promoting (or alternatively inhibiting) proliferation of a cell responsive to a growth factor, morphogen or other environmental cue which affects the cell through at least one signal transduction pathway which includes a MEKK1 protein. In general, the method comprises contacting cells with an amount of an agent which significantly (statistically) modulates MEKK-dependent signaling by the factor. For instance, it is contemplated by the invention that, in light of the present finding of an apparently broad involvement of members of the MEKK protein family in signal pathways implicated in the formation of ordered spatial arrangements of differentiated tissues in vertebrates, the subject method could be used to generate and/or maintain an array of different vertebrate tissue both in vitro and in vivo. A "MEKK1 therapeutic" whether inductive or anti-inductive with respect to signaling by a MEKK1-dependent pathway, can be, as appropriate, any of the preparations described above, including isolated polypeptides, gene therapy constructs, antisense molecules, peptidomimetics or agents identified in the drug assays provided herein.

There are a wide variety of pathological cell proliferative conditions for which MEKK1 therapeutics of the present invention are useful. For instance, such agents provide therapeutic benefits where the general strategy being the inhibition of an anomalous cell proliferation. Diseases that might benefit from this methodology include, but are not limited to, various cancers and leukemias, psoriasis, bone diseases, fibroproliferative disorders such as involving connective tissues, atherosclerosis and other smooth muscle proliferative disorders, autoimmune disease, inflammatory conditions such as rheumatoid arthritis, multiple sclerosis and complications arising from organ transplantation, allergic responses, as well as respiratory inflammation (e.g., asthma and chronic obstructive pulmonary disease), and inflammatory bowel disease (e.g., Crohn's disease and ulcerative colitis).

In addition to proliferative disorders, the present invention contemplates the use of MEKK1 therapeutics for the treatment of differentiative disorders which result from, for example, dedifferentiation of tissue which may optionally be accompanied by apoptosis.

Additionally, MEKK1 molecules may play an important role in the _etiology of certain viral diseases, including, but not limited to, Hepatitis B, Hepatitis C, and Herpes Simplex Virus (HSV). Modulators of MEKK1 activity could be used to control viral diseases. The modulators can be used in the treatment and/or diagnosis of viral infected tissue or virus-associated tissue fibrosis, especially liver and liver fibrosis. Also, MEKK1 modulators can be used in the treatment and/or diagnosis of virus-associated carcinoma, especially hepatocellular cancer.

As discussed, successful treatment of MEKK1 disorders can be brought about by techniques that serve to inhibit the expression or activity of target gene products. For example, compounds, e.g., an agent identified using an assays described above, that proves to exhibit negative modulatory activity, can be used in accordance with the invention to prevent and/or ameliorate symptoms of MEKK1 disorders. Such molecules can include, but are not limited to, peptides, phosphopeptides, small organic or inorganic molecules, or antibodies (including, for example, polyclonal, monoclonal, humanized, anti-idiotypic, chimeric or single chain antibodies, and Fab, F(ab), and Fab expression library fragments, scFV molecules, and epitope-binding fragments thereof).

Further, antisense and ribozyme molecules that inhibit expression of the target gene can also be used in accordance with the invention to reduce the level of target gene expression, thus effectively reducing the level of target gene activity. Still further, triple helix molecules can be utilized in reducing the level of target gene activity. Antisense, ribozyme and triple helix molecules are discussed above.

It is possible that the use of antisense, ribozyme, and/or triple helix molecules to reduce or inhibit mutant gene expression can also reduce or inhibit the transcription (triple helix) and/or translation (antisense, ribozyme) of mRNA produced by normal target gene alleles, such that the concentration of normal target gene product present can be lower than is necessary for a normal phenotype. In such cases, nucleic acid molecules that encode and express target gene polypeptides exhibiting normal target gene activity can be introduced into cells via gene therapy method. Alternatively, in instances in that the target gene encodes an extracellular protein, it can be preferable to co-administer normal target gene protein into the cell or tissue in order to maintain the requisite level of cellular or tissue target gene activity.

Another method by which nucleic acid molecules may be utilized in treating or preventing a disease characterized by MEKK1 expression is through the use of aptamer molecules specific for MEKK1 protein. Aptamers are nucleic acid molecules having a tertiary structure which permits them to specifically bind to protein ligands (see, e.g., Osborne et al., *Curr. Opin. Chem Biol.*, 1: 5–9 (1997); and Patel, *Curr. Opin. Chem. Biol.* 1:32–46 (1997)). Since nucleic acid molecules may in many cases be more conveniently introduced into target cells than therapeutic protein molecules may be, aptamers offer a method by which MEKK1 protein activity may be specifically decreased without the introduction of drugs or other molecules which may have pluripotent effects.

Antibodies can be generated that are both specific for target gene product and that reduce target gene product activity. Such antibodies may, therefore, by administered in instances whereby negative modulatory techniques are appropriate for the treatment of MEKK1 disorders. For a description of antibodies, see the Antibody section above.

In circumstances wherein injection of an animal or a human subject with a MEKK1 protein or epitope for stimulating antibody production is harmful to the subject, it is possible to generate an immune response against MEKK1 through the use of anti-idiotypic antibodies (see, for example, Herlyn, *D. Ann Med* 1999; 31(1):6678; and Bhattacharya-Chatterjee, M., and Foon, K. A. *Cancer Treat Res* 1998; 94:51–68). If an anti-idiotypic antibody is introduced into a mammal or human subject, it should stimulate the production of anti-anti-idiotypic antibodies, which should be specific to the MEKK1 protein. Vaccines directed to a disease characterized by MEKK1 expression may also be generated in this fashion.

Instances where the target antigen is intracellular and whole antibodies are used, internalizing antibodies may be preferred. Lipofectin or liposomes can be used to deliver the antibody or a fragment of the Fab region that binds to the target antigen into cells. Where fragments of the antibody are used, the smallest inhibitory fragment that binds to the target antigen is preferred. For example, peptides having an amino acid sequence corresponding to the Fv region of the antibody can be used. Alternatively, single chain neutralizing antibodies that bind to intracellular target antigens can also be administered. Such single chain antibodies can be administered, for example, by expressing nucleotide sequences encoding single-chain antibodies within the target cell population (see e.g., Marasco et al., *Proc. Natl. Acad. Sci. USA* 90:7889–7893 (1993)).

The identified compounds that inhibit target gene expression, synthesis and/or activity can be administered to a patient at therapeutically effective doses to prevent, treat or ameliorate MEKK1 disorders. A therapeutically effective dose refers to that amount of the compound sufficient to result in amelioration of symptoms of the disorders.

Toxicity and therapeutic efficacy of such compounds can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compounds that exhibit large therapeutic indices are preferred. While compounds that exhibit toxic side effects can be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the $ED_{50}$, with little or no toxicity. The dosage can vary within this range depending upon the dosage form employed and the route of administration utilized. For any compound used in the method of the invention, the therapeutically effective dose can be estimated initially from cell culture assays. A dose can be formulated in animal models to achieve a circulating plasma concentration range that includes the $IC_{50}$ (i.e., the concentration of the test compound that achieves a half-maximal inhibition of symptoms) as determined in cell culture. Such information can be used to more accurately determine useful doses in humans. Levels in plasma can be measured, for example, by high performance liquid chromatography.

Another example of determination of effective dose for an individual is the ability to directly assay levels of "free" and "bound" compound in the serum of the test subject. Such assays may utilize antibody mimics and/or "biosensors" that have been created through molecular imprinting techniques. The compound which is able to modulate MEKK1 activity is used as a template, or "imprinting molecule", to spatially organize polymerizable monomers prior to their polymerization with catalytic reagents. The subsequent removal of the imprinted molecule leaves a polymer matrix which contains a repeated "negative image" of the compound and is able to selectively rebind the molecule under biological assay conditions. A detailed review of this technique can be seen in Ansell, R. J. et al (1996) *Current Opinion in Biotechnology* 7:89–94 and in Shea, K. J. (1994) *Trends in Polymer Science* 2:166–173. Such "imprinted" affinity matrixes are amenable to ligand-binding assays, whereby the immobilized monoclonal antibody component is replaced by an appropriately imprinted matrix. An example of the use of such matrixes in this way can be seen in Vlatakis, G. et al (1993) *Nature* 361:645–647. Through the use of isotope-labeling, the "free" concentration of compound which modulates the expression or activity of MEKK1 can be readily monitored and used in calculations of $IC_{50}$.

Such "imprinted" affinity matrixes can also be designed to include fluorescent groups whose photon-emitting properties measurably change upon local and selective binding of target compound. These changes can be readily assayed in real time using appropriate fiberoptic devices, in turn allowing the dose in a test subject to be quickly optimized based on its individual $IC_{50}$. A rudimentary example of such a "biosensor" is discussed in Kriz, D. et al (1995) *Analytical Chemistry* 67:2142–2144.

Another aspect of the invention pertains to methods of modulating MEKK1 expression or activity for therapeutic purposes. Accordingly, in an exemplary embodiment, the modulatory method of the invention involves contacting a cell with a MEKK1 or agent that modulates one or more of the activities of MEKK1 protein activity associated with the cell. An agent that modulates MEKK1 protein activity can be an agent as described herein, such as a nucleic acid or a protein, a naturally-occurring target molecule of a MEKK1 protein (e.g., a MEKK1 substrate or receptor), a MEKK1 antibody, a MEKK1 agonist or antagonist, a peptidomimetic of a MEKK1 agonist or antagonist, or other small molecule.

In one embodiment, the agent stimulates one or MEKK1 activities. Examples of such stimulatory agents include active MEKK1 protein and a nucleic acid molecule encoding MEKK1. In another embodiment, the agent inhibits one or more MEKK1 activities. Examples of such inhibitory agents include antisense MEKK1 nucleic acid molecules, anti-MEKK1 antibodies, and MEKK1 inhibitors. These modulatory methods can be performed in vitro (e.g., by culturing the cell with the agent) or, alternatively, in vivo (e.g., by administering the agent to a subject). As such, the present invention provides methods of treating an individual afflicted with a disease or disorder characterized by aberrant or unwanted expression or activity of a MEKK1 protein or nucleic acid molecule. In one embodiment, the method involves administering an agent (e.g., an agent identified by a screening assay described herein), or combination of agents that modulates (e.g., upregulates or downregulates) MEKK1 expression or activity. In another embodiment, the method involves administering a MEKK1 protein or nucleic acid molecule as therapy to compensate for reduced, aberrant, or unwanted MEKK1 expression or activity.

Stimulation of MEKK1 activity is desirable in situations in which MEKK1 is abnormally downregulated and/or in which increased MEKK1 activity is likely to have a beneficial effect. For example, stimulation of MEKK1 activity is desirable in situations in which a MEKK1 is downregulated and/or in which increased MEKK1 activity is likely to have a beneficial effect. Likewise, inhibition of MEKK1 activity is desirable in situations in which MEKK1 is abnormally upregulated and/or in which decreased MEKK1 activity is likely to have a beneficial effect.

Pharmacogenomics

The MEKK1 molecules of the present invention, as well as agents, or modulators which have a stimulatory or inhibitory effect on MEKK1 activity (e.g., MEKK1 gene expression) as identified by a screening assay described herein can be administered to individuals to treat (prophylactically or therapeutically) MEKK1 associated disorders (e.g., cell signaling or cell adhesion) associated with aberrant or unwanted MEKK1 activity. In conjunction with such treatment, pharmacogenomics (i.e., the study of the relationship between an individual's genotype and that individual's response to a foreign compound or drug) may be considered. Differences in metabolism of therapeutics can lead to severe toxicity or therapeutic failure by altering the relation between dose and blood concentration of the pharmacologically active drug. Thus, a physician or clinician may consider applying knowledge obtained in relevant pharmacogenomics studies in determining whether to administer a MEKK1 molecule or MEKK1 modulator as well as tailoring the dosage and/or therapeutic regimen of treatment with a MEKK1 molecule or MEKK1 modulator.

Pharmacogenomics deals with clinically significant hereditary variations in the response to drugs due to altered drug disposition and abnormal action in affected persons. See, for example, Eichelbaum et al., *Clin. Exp. Pharmacol. Physiol.* 23(10–11):983–985 (1996) and Linder et al., *Clin. Chem.* 43(2):254–266 (1997). In general, two types of pharmacogenetic conditions can be differentiated. Genetic conditions transmitted as a single factor altering the way drugs act on the body (altered drug action) or genetic conditions transmitted as single factors altering the way the body acts on drugs (altered drug metabolism). These pharmacogenetic conditions can occur either as rare genetic defects or as naturally-occurring polymorphisms.

One pharmacogenomics approach to identifying genes that predict drug response, known as "a genome-wide association", relies primarily on a high-resolution map of the human genome consisting of already known gene-related markers (e.g., a "bi-allelic" gene marker map which consists of 60,000–100,000 polymorphic or variable sites on the human genome, each of which has two variants.) Such a high-resolution genetic map can be compared to a map of the genome of each of a statistically significant number of patients taking part in a Phase II/III drug trial to identify markers associated with a particular observed drug response or side effect. Alternatively, such a high resolution map can be generated from a combination of some ten-million known single nucleotide polymorphisms (SNPs) in the human genome. As used herein, a "SNP" is a common alteration that occurs in a single nucleotide base in a stretch of DNA. For example, a SNP may occur once per every 1000 bases of DNA. A SNP may be involved in a disease process, however, the vast majority may not be disease-associated. Given a genetic map based on the occurrence of such SNPs, individuals can be grouped into genetic categories depending on a particular pattern of SNPs in their individual genome. In such a manner, treatment regimens can be tailored to groups of genetically similar individuals, taking into account traits that may be common among such genetically similar individuals.

Alternatively, a method termed the "candidate gene approach", can be utilized to identify genes that predict drug response. According to this method, if a gene that encodes a drug's target is known (eg., a MEKK1 protein of the present invention), all common variants of that gene can be fairly easily identified in the population and it can be determined if having one version of the gene versus another is associated with a particular drug response.

Alternatively, a method termed the "gene expression profiling", can be utilized to identify genes that predict drug response. For example, the gene expression of an animal dosed with a drug (e.g., a MEKK1 molecule or MEKK1 modulator of the present invention) can give an indication whether gene pathways related to toxicity have been turned on.

Information generated from more than one of the above pharmacogenomics approaches can be used to determine appropriate dosage and treatment regimens for prophylactic or therapeutic treatment of an individual. This knowledge, when applied to dosing or drug selection, can avoid adverse reactions or therapeutic failure and thus enhance therapeutic or prophylactic efficiency when treating a subject with a MEKK1 molecule or MEKK1 modulator, such as a modulator identified by one of the exemplary screening assays described herein.

The present invention further provides methods for identifying new agents, or combinations, that are based on identifying agents that modulate the activity of one or more of the gene products encoded by one or more of the MEKK1 genes of the present invention, wherein these products may be associated with resistance of the cells to a therapeutic agent. Specifically, the activity of the proteins encoded by the MEKK1 genes of the present invention can be used as a basis for identifying agents for overcoming agent resistance. By blocking the activity of one or more of the resistance proteins, target cells, e.g., epithelial cells, will become sensitive to treatment with an agent to which the unmodified target cells were resistant.

Monitoring the influence of agents (e.g., drugs) on the expression or activity of a MEKK1 protein can be applied in clinical trials. For example, the effectiveness of an agent determined by a screening assay as described herein to increase MEKK1 gene expression, protein levels, or upregulate MEKK1 activity, can be monitored in clinical trials of subjects exhibiting decreased MEKK1 gene expression, protein levels, or downregulated MEKK1 activity. Alternatively, the effectiveness of an agent determined by a screening assay to decrease MEKK1 gene expression, protein levels, or downregulate MEKK1 activity, can be monitored in clinical trials of subjects exhibiting increased MEKK1 gene expression, protein levels, or upregulated MEKK1 activity. In such clinical trials, the expression or activity of a MEKK1 gene, and preferably, other genes that have been implicated in, for example, a MEKK1-associated disorder can be used as a "read out" or markers of the phenotype of a particular cell.

Other Embodiments

In another aspect, the invention features, a method of analyzing a plurality of capture probes. The method can be used, e.g., to analyze gene expression. The method includes: providing a two dimensional array having a plurality of addresses, each address of the plurality being positionally distinguishable from each other address of the plurality, and each address of the plurality having a unique capture probe, e.g., a nucleic acid or peptide sequence; contacting the array with a MEKK1, preferably purified, nucleic acid, preferably purified, polypeptide, preferably purified, or antibody, and thereby evaluating the plurality of capture probes. Binding, e.g., in the case of a nucleic acid, hybridization with a capture probe at an address of the plurality, is detected, e.g., by signal generated from a label attached to the MEKK1 nucleic acid, polypeptide, or antibody.

The capture probes can be a set of nucleic acids from a selected sample, e.g., a sample of nucleic acids derived from a control or non-stimulated tissue or cell.

The method can include contacting the MEKK1 nucleic acid, polypeptide, or antibody with a first array having a plurality of capture probes and a second array having a different plurality of capture probes. The results of each hybridization can be compared, e.g., to analyze differences in expression between a first and second sample. The first plurality of capture probes can be from a control sample, e.g., a wild type, normal, or non-diseased, non-stimulated, sample, e.g., a biological fluid, tissue, or cell sample. The second plurality of capture probes can be from an experimental sample, e.g., a mutant type, at risk, disease-state or disorder-state, or stimulated, sample, e.g., a biological fluid, tissue, or cell sample.

The plurality of capture probes can be a plurality of nucleic acid probes each of which specifically hybridizes, with an allele of MEKK1. Such methods can be used to diagnose a subject, e.g., to evaluate risk for a disease or disorder, to evaluate suitability of a selected treatment for a subject, or to evaluate whether a subject has a disease or disorder.

The method can be used to detect SNPs, as described above.

In another aspect, the invention features, a method of analyzing a plurality of probes. The method is useful, e.g., for analyzing gene expression. The method includes: providing a two dimensional array having a plurality of addresses, each address of the plurality being positionally distinguishable from each other address of the plurality having a unique capture probe, e.g., wherein the capture probes are from a cell or subject which express MEKK1 or from a cell or subject in which a MEKK1 mediated response has been elicited, e.g., by contact of the cell with MEKK1 nucleic acid or protein, or administration to the cell or subject MEKK1 nucleic acid or protein; contacting the array with one or more inquiry probe, wherein an inquiry probe can be a nucleic acid, polypeptide, or antibody (which is preferably other than MEKK1 nucleic acid, polypeptide, or antibody); providing a two dimensional array having a plurality of addresses, each address of the plurality being positionally distinguishable from each other address of the plurality, and each address of the plurality having a unique capture probe, e.g., wherein the capture probes are from a cell or subject which does not express MEKK1 (or does not express as highly as in the case of the MEKK1 positive plurality of capture probes) or from a cell or subject which in which a MEKK1 mediated response has not been elicited (or has been elicited to a lesser extent than in the first sample); contacting the array with one or more inquiry probes (which is preferably other than a MEKK1 nucleic acid, polypeptide, or antibody), and thereby evaluating the plurality of capture probes. Binding, e.g., in the case of a nucleic acid, hybridization with a capture probe at an address of the plurality, is detected, e.g., by signal generated from a label attached to the nucleic acid, polypeptide, or antibody.

In another aspect, the invention features, a method of analyzing MEKK1, e.g., analyzing structure, function, or relatedness to other nucleic acid or amino acid sequences. The method includes: providing a MEKK1 nucleic acid or amino acid; comparing the MEKK1 sequence with one or more preferably a plurality of sequences from a collection of sequences, e.g., a nucleic acid or protein sequence database; to thereby analyze MEKK1.

The method can include evaluating the sequence identity between a MEKK1 sequence and a database sequence. The method can be performed by accessing the database at a second site, e.g., over the internet.

In another aspect, the invention features, a set of oligonucleotides, useful, e.g., for identifying SNP's, or identifying specific alleles of MEKK1. The set includes a plurality of oligonucleotides, each of which has a different nucleotide at an interrogation position, e.g., an SNP or the site of a mutation. In a preferred embodiment, the oligonucleotides of the plurality identical in sequence with one another (except for differences in length). The oligonucleotides can be provided with differential labels, such that an oligonucleotides which hybridizes to one allele provides a signal that is distinguishable from an oligonucleotides which hybridizes to a second allele.

The sequence of a MEKK1 molecules is provided in a variety of mediums to facilitate use thereof. A sequence can be provided as a manufacture, other than an isolated nucleic acid or amino acid molecule, which contains a MEKK1. Such a manufacture can provide a nucleotide or amino acid sequence, eg., an open reading frame, in a form which allows examination of the manufacture using means not directly applicable to examining the nucleotide or amino acid sequences, or a subset thereof, as they exists in nature or in purified form.

A MEKK1 nucleotide or amino acid sequence can be recorded on computer readable media. As used herein, "computer readable media" refers to any medium that can be read and accessed directly by a computer. Such media include, but are not limited to: magnetic storage media, such as floppy discs, hard disc storage medium, and magnetic tape; optical storage media such as CD-ROM; electrical storage media such as RAM and ROM; and hybrids of these categories such as magnetic/optical storage media.

A variety of data storage structures are available to a skilled artisan for creating a computer readable medium having recorded thereon a nucleotide or amino acid sequence of the present invention. The choice of the data storage structure will generally be based on the means chosen to access the stored information. In addition, a variety of data processor programs and formats can be used to store the nucleotide sequence information of the present invention on computer readable medium. The sequence information can be represented in a word processing text file, formatted in commercially-available software such as WordPerfect and Microsoft Word, or represented in the form of an ASCII file, stored in a database application, such as DB2, Sybase, Oracle, or the like. The skilled artisan can readily adapt any number of data processor structuring formats (e.g., text file or database) in order to obtain computer readable medium having recorded thereon the nucleotide sequence information of the present invention.

By providing the nucleotide or amino acid sequences of the invention in computer readable form, the skilled artisan can routinely access the sequence information for a variety of purposes. For example, one skilled in the art can use the nucleotide or amino acid sequences of the invention in computer readable form to compare a target sequence or target structural motif with the sequence information stored within the data storage means. A search is used to identify fragments or regions of the sequences of the invention which match a particular target sequence or target motif.

As used herein, a "target sequence" can be any DNA or amino acid sequence of six or more nucleotides or two or more amino acids. A skilled artisan can readily recognize that the longer a target sequence is, the less likely a target sequence will be present as a random occurrence in the database. Typical sequence lengths of a target sequence are from about 10 to 100 amino acids or from about 30 to 300 nucleotide residues. However, it is well recognized that commercially important fragments, such as sequence fragments involved in gene expression and protein processing, may be of shorter length.

Computer software is publicly available which allows a skilled artisan to access sequence information provided in a computer readable medium for analysis and comparison to other sequences. A variety of known algorithms are disclosed publicly and a variety of commercially available software for conducting search means are and can be used in the computer-based systems of the present invention. Examples of such software include, but are not limited to, MacPattern (EMBL), BLASTN and BLASTX (NCBIA).

Thus, the invention features a method of making a computer readable record of a sequence of a MEKK1 sequence that includes recording the sequence on a computer readable matrix. In a preferred embodiment the record includes one or more of the following: identification of an ORF; identification of a domain, region, or site; identification of the start of transcription; identification of the transcription terminator; the full length amino acid sequence of the protein, or a mature form thereof; the 5' end of the translated region; or 3' regulatory elements.

In another aspect, the invention features, a method of analyzing a sequence. The method includes: providing a MEKK1 sequence, or record, in computer readable form; comparing a second sequence to the gene name sequence; thereby analyzing a sequence. Comparison can include comparing to sequences for sequence identity or determining if one sequence is included within the other, e.g., determining if the MEKK1 sequence includes a sequence being compared. In a preferred embodiment the MEKK1 or second sequence is stored on a first computer, e.g., at a first site and the comparison is performed, read, or recorded on a second computer, e.g., at a second site. For example, the MEKK1 or second sequence can be stored in a public or proprietary database in one computer, and the results of the comparison performed, read, or recorded on a second computer. In a preferred embodiment the record includes one or more of the following: identification of an ORF; identification of a domain, region, or site; identification of the start of transcription; identification of the transcription terminator; the full length amino acid sequence of the protein, or a mature form thereof; the 5' end of the translated region; or 3' regulatory elements.

This invention is further illustrated by the following examples that should not be construed as limiting. The contents of all references, patents and published patent applications cited throughout this application are incorporated herein by reference.

EXAMPLES

Example 1

Cloning the Full-Length Human MEKK1 Gene

The full-length human MEKK1 cDNA was isolated by screening a human placenta cDNA library. This cDNA encodes a 4.5 kb open reading frame which predicts a 164.5 kDa protein.

The human Placenta 5'-STRETCHPLUS cDNA library was purchased from Clontech Laboratories, Inc. (Palo Alto, Calif.). The library vector was phage lambda gt11. Approximately 500,000 plaques were screened for human MEKK1 clones according to the Clontech lambda library protocol. Phage were plated on 15–150 mm LB plates supplemented with 10 mM $Mg_2SO_4$ and incubated at 42° C. Duplicates of 80-S BA nitrocellulose filters (Schleicher & Schuell, Keene, N. H.) were lifted from the 15 plates, then treated to denature and renature the DNA on the filters, and then oven-baked at 80° C. for 2 hours. The filters were then incubated in a prehybridization solution of 50% formamide, 5×SSPE, 5× Denhardt's solution, 0.1% SDS, and 0.1 mg/ml denatured herring sperm DNA for 4 hours, then labeled DNA probe was added. The DNA probe was about a 500 bps DNA fragment of SacII and XmmI digested EST clone (W96411) (Research Genetics, Huntsville, Ala.) of partial human MEKK1 DNA. The DNA probe was labeled with $^{32}$P-dCTP using the Prime-It® II kit from Stratagene (La Jolla, Calif.). Ten positive plaques were picked for secondary screening. Six positives were confirmed. Lambda phage DNA was prepared using a Lambda phage DNA Wizard Prep kit (Promega, Madison, Wis.). Restriction digestion with EcoRI revealed that the longest insert was about a 5.5 kb sequence contained in one of the six positive phage DNAs. The insert was cloned into bacterial plasmid pbluescript SK+ at the EcoRI site and named pM6. The entire cDNA insert was sequenced. The resulting nucleotide sequence (SEQ ID NO:1) was aligned to the known full-length rat MEKK1 sequence and determined to be the full-length human MEKK1 by homology.

The human MEKK1 sequence, (FIG. 1; SEQ ID NO:1), which is approximately 5245 nucleotides long, including untranslated regions, contains a predicted methionine-initiated coding sequence of about 4539 nucleotides (nucleotides 7–4542 of SEQ ID NO:1. The coding sequence encodes a 1512 amino acid protein (SEQ ID NO:2).

Figure 2:
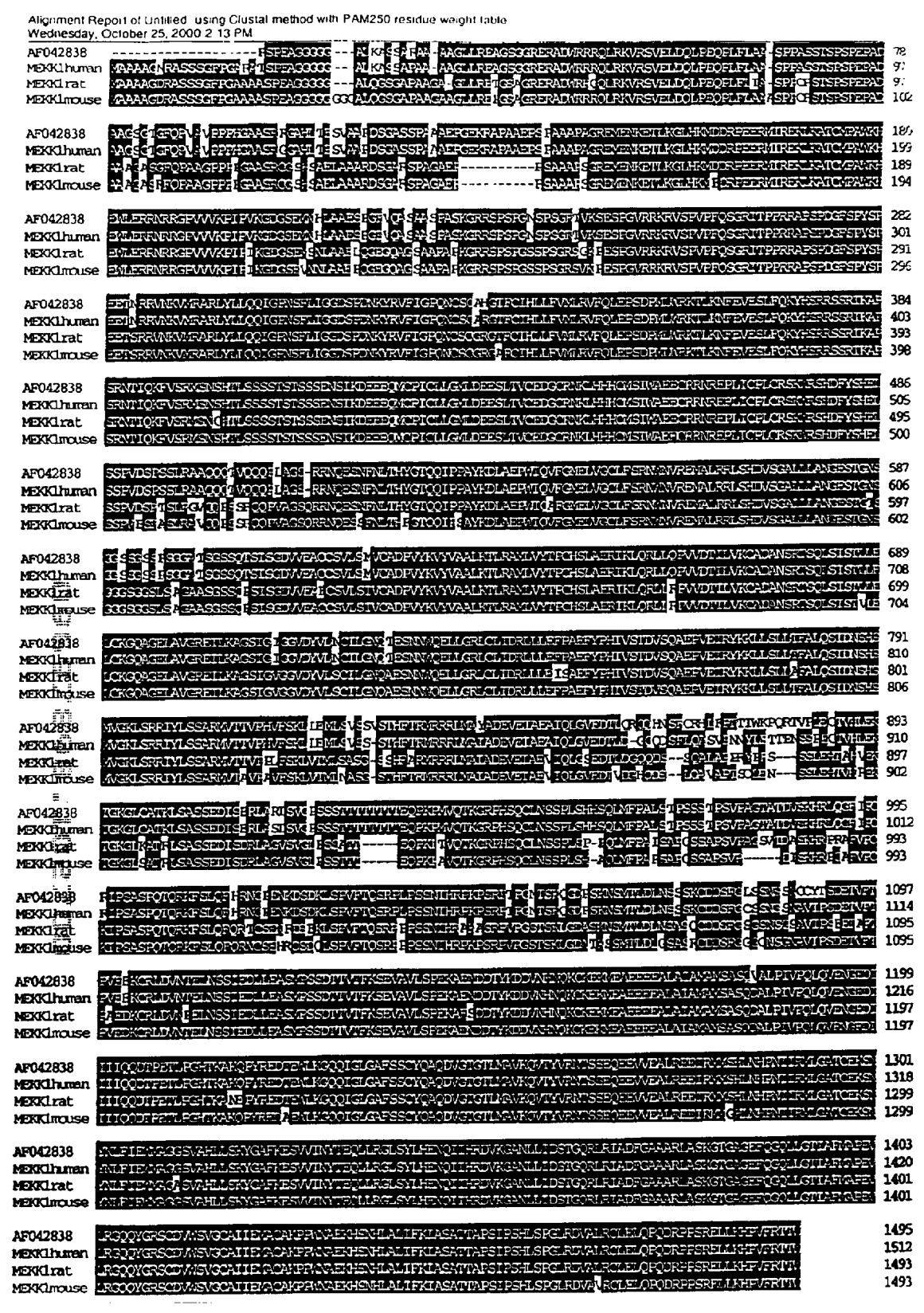

FIG. 2 shows the amino acid sequence alignment of the full length human MEKK1 protein against other known MEKK1 proteins of other species. This 1512 amino acid of human MEKK1 is 89% identical to the rat MEKK1 amino acid sequence.

Example 2

The Full-Length MEKK1 is an Activator of NFκB

The importance of MEKK1 function in the AP-1 pathway is well established. (Gottschalf et al., *J. Exp. Med.* 178:1681 (1993); Want et al., *J. Mol. Cell. Biol.* 14:11153 (1994); Rao, *Immunol. Today* 15:274 (1994); Angel et al., *Biochem. Biophys. Acta.* 1072:129 (1991).) However, the involvement of MEKK1 in NFκ•B has been unclear. As described herein, a NFκB reporter assay was performed to examine the effect of MEKK1 in this pathway. The full-length human MEKK1 cDNA was subcloned into the mammalian cell expression vector pcDNA3 (Invitrogen, Carlsbad, Calif.). This pcDNA3 vector was also constructed using oligo directed-mutagenesis to have a 9-amino acid FLAG epitope fused at the carboxy-terminus of the MEKK1 protein. By using an antibody specific for the FLAG epitope, expression of the human MEKK1 full-length protein can be determined.

HeLa cells were split at $1.5 \times 10^5$ per 35 mm plates 24 hours before MEKK1 transfection using the $CaPO_4$ method (Invitrogen, Carlsbad, Calif.). HeLa cells were transfected with increasing amounts of pcDAN3 expressing the C-terminal FLAG-tagged human MEKK1 and co-transfected with 1 ug of an NFκB reporter p(PRDII)$_4$ DNA containing the chloramphenicol acetyltransferase gene under the control of a promoter containing four NFκ.B binding sites. Total DNA concentrations were kept constant at 4 μg by adding empty pcDNA3. As a positive control, a pcDNA3 vector expressing a N-terminal FLAG-tagged NIK protein was used. NIK, a NFκB inducing kinase, is known to be a very potent activator of NFκB. After 24 hours, the cells were washed three time with PBS and lysed in reporter lysis buffer (Promega, Madison, Wis.). Lysates were harvested by scraping and were transferred to Eppendorf tubes. The protein concentration of each cell extract was determined by Coomassie Plus Protein Assay Reagent (Pierce, Rockford, Ill.). The expression levels of transfected MEKK1 and NIK proteins were examined by Western blot analysis (FIG. 3). Ten micrograms of each sample was applied onto a 4–12% SDS-PAGE gradient gel, then transferred to a nitrocellulose membrane. Anti-FLAG antibody was used as the primary antibody; the secondary antibody was HRP-conjugated anti-mouse antibody (Amersham Pharmacia Biotech, England). The Western blot was developed with ECL reagents (Amersham Pharmacia Biotech, England).

The protein expression levels are shown in the Western blot of FIG. 3. Increasing amounts of MEKK1 were synthesized in HeLa cells which correlated with the amount of cDNA3-MEKK1flag DNA used in the transfection. Expressed full-length MEKK1 protein migrated on the SDS gel with an apparent molecular weight of 196 kDa.

Figure 4:
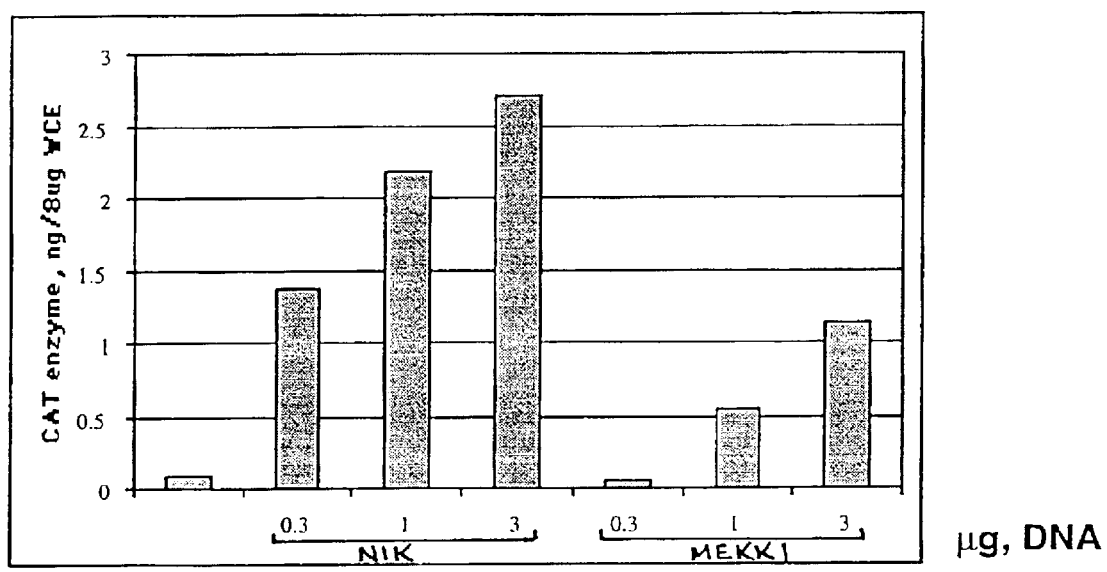
FIG. 4 shows a graph of the results of a CAT ELISA to measure NFκ•B activation by MEKK1.

To assay NFκB activity, the levels of chloramphenicol acetyltransferase protein was measured by CAT ELISA (Roche Molecular Biochemicals, Indianapolis, Ind.) (FIG. 4). CAT ELISA was performed using 8•μg of each extract. The amount of CAT protein in the 8 μg extract was calculated relative to the CAT standard and was graphed along the Y axis as the amount of CAT protein per 8•μg extract. The X axis indicates increasing microgram amounts of trans-fected pcDNA3-flagMEKK1 or pcDNA3-flagNIK DNAs.

The results show that transient expression of the full-length human MEKK1 protein increased the NF.κB activity in cells. The level of NFκ.B activation changes in a dose-dependent manner with the level of MEKK1 protein expression, although the extent of NF.κB activation is apparently weaker compare than that of expressed NIK protein. This example demonstrates that full-length human MEKK1 protein functions as an activator of NFκB in cells.

Example 3

The Full-Length MEKK1 Interacts with IKK1 in Cells

One crucial step in NFκB activation pathway is the signal-induced phosphorylation of IκB proteins by the IκB kinase complex. To further characterize MEKK1 function in NFκ.Bactivation, MEKK1 was assayed for direct activation of the IκB kinase by measuring MEKK1 interaction with components of the IκB kinase complex.

Transfections were performed exactly according to the manufacturer's protocol using LipofectAMINE PLUS Regent (Life Technologies, Rockville, Md.). Human 293 cells were split at $2 \times 10^6$ per 100 mm plate 24 hours before transfection. The expression vectors were 4 ug each of the following DNAs: pcDNA3MEKK1flag, pcDNA3flagHANIK in the presence or absence of pcDNA-mycIKK1 or pcDNA3mycIKK2. After 28 hours, cells were washed with PBS and resuspended in a lysis buffer (50 mM HEPES pH 7.9, 100 mM NaCl, 10% glycerol, 1 mM EDTA, 20 μMα glycerolphosphate, 1 mM NaPO$_4$, 1 mM sodium metabisulphite, 20 mM PNPP, 0.1% NP-40, and protease inhibitor cocktail). Cell lysates were incubated with 15•l of anti-flag antibody M2 resin (Sigma, St. Louis, Mo.) for 4 hours at 4° C. The M2 resin was then washed three times with the lysis buffer. Proteins that contained the flag epitope remained bound to the anti-flag M2 beads along with other proteins that specifically associated with the flag-tagged protein. Immunoprecipitates were resolved on a 4–12% SDS-PAGE gel and transferred to nitrocellulose membranes. Western blot analysis was performed first with anti-myc antibody (Santa Cruz Biotech, Santa Cruz, Calif.) for the presence of mycIKK1 and mycIKK2 proteins in the immune complex. Then, anti-flag antibody was used to detect flag-tagged MEKK1 and flag-tagged NIK proteins (Sigma, St. Louis, Mo.).

Figure 5:
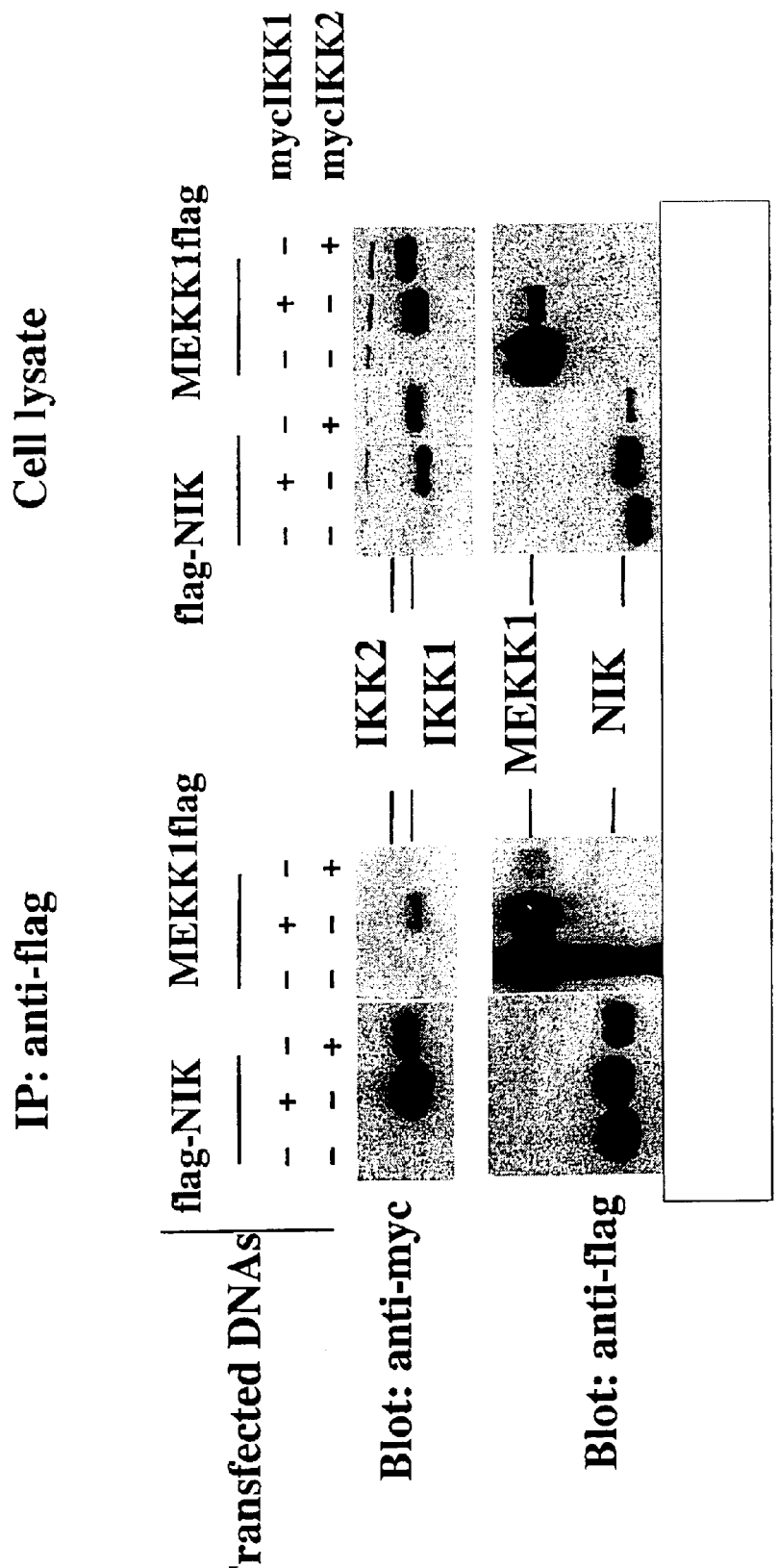
FIG. 5 shows the results of a Western blot of immunoprecipitates of cell lysates of transfected cells expressing different tags using either anti-myc or anti-flag antibodies.

The results are shown in FIG. 5. NIK protein was used as a positive control because it is known to activate the IκB kinase by interacting with IKK1 and IKK2. As in the flag-NIK immunoprecipitates, the myc-tagged IKK1 protein was detected specifically in the flag-tagged full-length MEKK1 immune complex. Therefore, the full-length MEKK1 is capable of interacting with IKK1. In contrast, the expression level of MEKK1 was extremely low when co-expressed with IKK2 protein, therefore the association between IKK2 and MEKK1 could not be observed. This example shows that at least one component of the IκB kinase interacts with MEKK1 protein.

Equivalents

Those skilled in the art will recognize, or be able to ascertain using no more than routine experimentation, many equivalents to the specific embodiments of the invention described herein. Such equivalents are intended to be encompassed by the following claims.

What is claimed is:

1. An isolated nucleic acid selected from the group consisting of:
   a. a nucleic acid comprising the nucleotide sequence of SEQ ID NO: 1 or nucleotides 7–4545 of SEQ ID NO: 1;
   b. a nucleic acid comprising the nucleotide sequence of the cDNA insert of the plasmid deposited with the ATCC as Accession Number PTA-1836 or a potion thereof, comprising the coding region;
   c. a nucleic acid which encodes a fragment of a polypeptide comprising the amino acid sequence of SEQ ID NO:2, wherein said fragment comprises at least 500 contiguous amino acids of SEQ ID NO:2 and has MEKK1 activity;
   d. a nucleic acid which has at least 90% nucleotide sequence identity with the entire length of the nucleotide sequence of SEQ ID NO: 1, wherein said nucleic acid comprises nucleotide residues 1 to 64 of SEQ ID NO: 1 and wherein said nucleic acid encodes for a protein having MEKK1 activity;

e. a nucleic acid which has at least 90% nucleotide sequence identity with the entire length of the nucleotide sequence of the insert of the plasmid deposited with the ATCC as Accession Number PTA-1836, wherein said nucleic acid comprises nucleotide residues 1 to 64 of SEQ ID NO:1 and wherein said nucleic acid encodes for a protein having MEKK1 activity;

f. a nucleic acid comprising the nucleotide sequence which encodes a polypeptide comprising the amino acid sequence of SEQ ID NO:2 or the amino acid sequence encoded by the cDNA insert of the plasmid deposited with ATCC as Accession Number PTA-1836;

g. a nucleic acid encoding a MEKK1 variant, wherein said MEKK1 variant comprises an amino acid sequence, having at least 90% amino acid sequence identity with the entire length of SEQ ID NO:2 wherein said nucleic acid encodes for amino acid residues 1 to 20 of SEQ ID NO:2, and wherein said variant has MEKK1 activity; and h. a nucleic acid encoding a MEKK1 variant, wherein said MEKK1 variant comprises an amino acid sequence having at least 98% amino acid sequence identity with the entire length of SEQ ID NO:2 and wherein said variant has MEKK1 activity.

2. The isolated nucleic acid of claim 1, wherein said nucleic acid further comprises a detectable label.

3. The isolated nucleic acid of claim 2, wherein said detectable label is selected from the group consisting of a chemiluminescent, fluorescent, radioactive, and colorimetric label.

4. An isolated vector selected from the group consisting of:

a. a vector comprising a recombinant nucleic acid comprising the nucleotide sequence of SEQ ID NO: 1 or nucleotides 7–4545 of SEQ ID NO:1;

h. a vector comprising a recombinant nucleic acid comprising the nucleotide sequence of the cDNA insert of the plasmid deposited with the ATCC as Accession Number PTA-1836 or a portion thereof comprising the coding region;

c. a vector comprising a recombinant nucleic acid which encodes a fragment of a polypeptide comprising the amino acid sequence of SEQ ID NO:2, wherein said fragment comprises at least 500 contiguous amino acids of SEQ ID NO:2 and has MEKK1 activity;

d. a vector comprising a recombinant nucleic acid which has at least 90% nucleotide sequence identity with the entire length of the nucleotide sequence of SEQ ID NO:1, wherein said nucleic acid comprises nucleotide residues 1 to 64 of SEQ ID NO:1 and wherein said nucleic acid encodes for a protein having MEKK1 activity;

e. a vector comprising a recombinant nucleic acid which has at least 90% nucleotide sequence identity with the entire length of the nucleotide sequence of the insert of the plasmid deposited with the ATCC as Accession Number PTA-1836, wherein said nucleic acid comprises nucleotide residues 1 to 64 of SEQ ID NO:1 and wherein said nucleic acid encodes for a protein having MEKK1 activity;

f. a vector comprising a recombinant nucleotide acid comprising the nucleotide sequence which encodes a polypeptide comprising the amino acid sequence of SEQ ID NO:2 or the amino acid sequence encoded by the cDNA insert of the plasmid deposited with ATCC as Accession Number PTA-1836;

g. a vector comprising a recombinant nucleic acid encoding a MEKK1 variant, wherein said MEKK1 variant comprises an amino acid sequence, having at least 90% amino acid sequence identity with the entire length of SEQ ID NO:2, wherein said nucleic acid encodes for amino acid residues 1 to 20 of SEQ ID NO:2, and wherein said variant has MEKK1 activity; and h. a vector comprising a recombinant nucleic acid encoding a MEKK1 variant, wherein said MEKK1 variant comprises an amino acid sequence having at least 98% amino acid sequence identity with entire length of SEQ ID NO:2 and wherein said variant has MEKK1 activity.

5. A host cell selected from the group consisting of:

a. a host cell comprising a recombinant nucleic acid comprising the nucleotide sequence of SEQ ID NO:1, or nucleotides 7–4545 of SEQ ID NO:1;

b. a host cell comprising a recombinant nucleic acid comprising the nucleotide sequence of the cDNA insert of the plasmid deposited with the ATCC as Accession Number PTA-1836 or a portion thereof comprising the coding region;

c. a host cell comprising a recombinant nucleic acid which encodes a fragment of a polypeptide comprising the amino acid sequence of SEQ ID NO:2, wherein said fragment comprises at least 500 contiguous amino acids of SEQ ID NO:2 and has MEKK1 activity;

d. a host cell comprising a recombinant nucleic acid which has at least 90% nucleotide sequence identity with the entire length of the nucleotide sequence of SEQ ID NO:1, wherein said nucleic acid comprises nucleotide residues 1 to 64 of SEQ ID NO:1 and wherein said nucleic acid encodes for a protein having MEKK1 activity, e. a host cell comprising a recombinant nucleic acid which has at least 90% nucleotide sequence identity with the entire length of the nucleotide sequence of the insert of the plasmid deposited with the ATCC as Accession Number PTA-1836, wherein said nucleic acid comprises nucleotide residues 1 to 64 of SEQ ID NO:1 and wherein said nucleic acid encodes for a protein having MEKK1 activity;

f. a host cell comprising a recombinant nucleic acid comprising the nucleotide sequence which encodes a polypeptide comprising the amino acid sequence of SEQ ID NO:2 or the amino acid sequence encoded by the cDNA insert of the plasmid deposited with ATCC as Accession Number PTA-1836;

g. a host cell comprising a recombinant nucleic acid encoding a MEKK1 variant, wherein said MEKK1 variant comprises an amino acid sequence, having at least 90% amino acid sequence identity with entire length of SEQ ID NO:2, wherein said nucleic acid encodes amino acid residues 1 to 20 of SEQ ID NO:2, and wherein said variant has MEKK1 activity; and h. a host cell comprising a recombinant nucleic acid encoding a MEKK1 variant, wherein said MEKK1 variant comprises an amino acid sequence, having at least 98% amino acid sequence identity with entire length of SEQ ID NO:2 and wherein said variant has MEKK1 activity;

wherein said recombinant nucleic acid is operatively linked to an expression control element.

6. The host cell of claim 5, wherein said host cell is a prokaryotic cell or a eukaryotic cell.

7. The host cell of claim 6, wherein said eukaryotic cell is a mammalian cell.

8. A method for producing a MEKK1 polypeptide comprising maintaining a host cell under conditions suitable for expression to produce the polypeptide, wherein said host cell comprises a recombinant nucleic acid selected from the group consisting of:
   a. a nucleic acid comprising the nucleotide sequence of SEQ ID NO:1 or nucleotides 7–4545 of SEQ ID NO:1; and
   b. a nucleic acid comprising a fragment of SEQ ID NO:1, wherein said fragment encodes a polypeptide comprising at least 500 contiguous amino acids of SEQ ID NO:2 and has MEKK1 activity.

9. The isolated nucleic acid molecule of claim 1, which is selected from the group consisting of:
   a. A nucleic acid molecule which encodes a polypeptide comprising the amino acid sequence of SEQ ID NO:2, or the amino acid sequence encoded by the cDNA insert of the plasmid deposited with the ATCC as Accession Number PTA-1835; and
   b. A nucleic acid comprising the nucleotide sequence of SEQ ID NO:1 or the cDNA insert of the plasmid deposited with the ATCC as Accession Number PTA-1836.

10. A vector comprising the nucleic acid molecule of claim 9.

11. A host cell that contains the vector of claim 10.

12. The host cell of claim 11, wherein the host cell is a mammalian host cell.

13. The nucleic acid molecule of claim 1 further comprising a nucleic acid sequence encoding a heterologous polypeptide.

14. A vector comprising the nucleic acid molecule of claim 13.

15. A host cell that contains the vector of claim 14.

16. The host cell of claim 15, wherein the host cell is a mammalian host cell.

17. The nucleic acid molecule of claim 9 further comprising a nucleic acid sequence encoding a heterologous polypeptide.

18. A vector comprising the nucleic acid molecule of claim 17.

19. A host cell that contains the vector of claim 18.

20. The host cell of claim 19, wherein the host cell is a mammalian host cell.

* * * * *

SEQUENCE LISTING

<160> NUMBER OF SEQ ID NOS: 28

<210> SEQ ID NO 1
<211> LENGTH: 5245
<212> TYPE: DNA
<213> ORGANISM: Human
<220> FEATURE:
<221> NAME/KEY: CDS
<222> LOCATION: (7)..(4545)

<400> SEQUENCE: 1

```
gagaaa atg gcg gcg gcg gcg ggg aat cgc gcc tcg tcg tcg gga ttc         48
       Met Ala Ala Ala Ala Gly Asn Arg Ala Ser Ser Ser Gly Phe
       1               5                   10 ccg ggc gcc agg gct acg agc cct gag gca ggc ggc ggc gga gga gcc         96
Pro Gly Ala Arg Ala Thr Ser Pro Glu Ala Gly Gly Gly Gly Gly Ala
15                  20                  25                  30 ctc aag gcg agc agc gcg ccc gcg gct gcc gcg gga ctg ctg cgg gag        144
Leu Lys Ala Ser Ser Ala Pro Ala Ala Ala Gly Leu Leu Arg Glu
                35                  40                  45 gcg ggc agc ggg ggc cgc gag cgg gcg gac tgg cgg cgg cgg cag ctg        192
Ala Gly Ser Gly Gly Arg Glu Arg Ala Asp Trp Arg Arg Arg Gln Leu
            50                  55                  60 cgc aaa gtg cgg agt gtg gag ctg gac cag ctg cct gag cag ccg ctc        240
Arg Lys Val Arg Ser Val Glu Leu Asp Gln Leu Pro Glu Gln Pro Leu
65                  70                  75 ttc ctt gcc gcc tca ccg ccg gcc tcc tcg act tcc ccg tcg ccg gag        288
Phe Leu Ala Ala Ser Pro Pro Ala Ser Ser Thr Ser Pro Ser Pro Glu
        80                  85                  90 ccc gcg gac gca gcg ggg agt ggg acc ggc ttc cag cct gtg gcg gtg        336
Pro Ala Asp Ala Ala Gly Ser Gly Thr Gly Phe Gln Pro Val Ala Val
95                  100                 105                 110 ccg ccg ccc cac gga gcc gcg agc cgc ggc ggc gcc cac ctt acc gag        384
Pro Pro Pro His Gly Ala Ala Ser Arg Gly Gly Ala His Leu Thr Glu
                115                 120                 125 tcg gtg gcg gcg ccg gac agc ggc gcc tcg agt ccc gca gcg gcc gag        432
Ser Val Ala Ala Pro Asp Ser Gly Ala Ser Ser Pro Ala Ala Ala Glu
            130                 135                 140 ccc ggg gag aag cgg gcg ccc gcc gcc gag ccg tct cct gca gcg gcc        480
Pro Gly Glu Lys Arg Ala Pro Ala Ala Glu Pro Ser Pro Ala Ala Ala
        145                 150                 155 ccc gcc ggt cgt gag atg gag aat aaa gaa act ctc aaa ggg ttg cac        528
Pro Ala Gly Arg Glu Met Glu Asn Lys Glu Thr Leu Lys Gly Leu His
160                 165                 170 aag atg gat gat cgt cca gag gaa cga atg atc agg gag aaa ctg aag        576
Lys Met Asp Asp Arg Pro Glu Glu Arg Met Ile Arg Glu Lys Leu Lys
175                 180                 185                 190 gca acc tgt atg cca gcc tgg aag cac gaa tgg ttg gaa agg aga aat        624
Ala Thr Cys Met Pro Ala Trp Lys His Glu Trp Leu Glu Arg Arg Asn
                195                 200                 205 agg cga ggg cct gtg gtg gta aaa cca atc cca gtt aaa gga gat gga        672
Arg Arg Gly Pro Val Val Val Lys Pro Ile Pro Val Lys Gly Asp Gly
            210                 215                 220
```

-continued

| | | |
|---|---|---|
| tct gaa atg aat cac tta gca gct gag tct cca gga gag gtc cag gca<br>Ser Glu Met Asn His Leu Ala Ala Glu Ser Pro Gly Glu Val Gln Ala<br>225 230 235 | 720 |
| agt gcg gct tca cca gct tcc aaa ggc cga cgc agt cct tct cct ggc<br>Ser Ala Ala Ser Pro Ala Ser Lys Gly Arg Arg Ser Pro Ser Pro Gly<br>240 245 250 | 768 |
| aac tcc cca tca ggt cgc aca gtg aaa tca gaa tct cca gga gta agg<br>Asn Ser Pro Ser Gly Arg Thr Val Lys Ser Glu Ser Pro Gly Val Arg<br>255 260 265 270 | 816 |
| aga aaa aga gtt tcc cca gtg cct ttt cag agt ggc aga atc aca cca<br>Arg Lys Arg Val Ser Pro Val Pro Phe Gln Ser Gly Arg Ile Thr Pro<br>275 280 285 | 864 |
| ccc cga aga gcc cct tca cca gat ggc ttc tca cca tat agc cct gag<br>Pro Arg Arg Ala Pro Ser Pro Asp Gly Phe Ser Pro Tyr Ser Pro Glu<br>290 295 300 | 912 |
| gaa aca aac cgc gtt aac aaa gtg atg cgg gcc aga ctg tac tta<br>Glu Thr Asn Arg Arg Val Asn Lys Val Met Arg Ala Arg Leu Tyr Leu<br>305 310 315 | 960 |
| ctg cag cag ata ggg cct aac tct ttc ctg att gga gga gac agc cca<br>Leu Gln Gln Ile Gly Pro Asn Ser Phe Leu Ile Gly Gly Asp Ser Pro<br>320 325 330 | 1008 |
| gac aat aaa tac cgg gtg ttt att ggg cct cag aac tgc agc tgt gca<br>Asp Asn Lys Tyr Arg Val Phe Ile Gly Pro Gln Asn Cys Ser Cys Ala<br>335 340 345 350 | 1056 |
| cgt gga aca ttc tgt att cat ctg cta ttt gtg atg ctc cgg gtg ttt<br>Arg Gly Thr Phe Cys Ile His Leu Leu Phe Val Met Leu Arg Val Phe<br>355 360 365 | 1104 |
| caa cta gaa cct tca gac cca atg tta tgg aga aaa act tta aag aat<br>Gln Leu Glu Pro Ser Asp Pro Met Leu Trp Arg Lys Thr Leu Lys Asn<br>370 375 380 | 1152 |
| ttt gag gtt gag agt ttg ttc cag aaa tat cac agt agg cgt agc tca<br>Phe Glu Val Glu Ser Leu Phe Gln Lys Tyr His Ser Arg Arg Ser Ser<br>385 390 395 | 1200 |
| agg atc aaa gct cca tct cgt aac acc atc cag aag ttt gtt tca cgc<br>Arg Ile Lys Ala Pro Ser Arg Asn Thr Ile Gln Lys Phe Val Ser Arg<br>400 405 410 | 1248 |
| atg tca aat tct cat aca ttg tca tca tct agt act tct acg tct agt<br>Met Ser Asn Ser His Thr Leu Ser Ser Ser Ser Thr Ser Thr Ser Ser<br>415 420 425 430 | 1296 |
| tca gaa aac agc ata aag gat gaa gag gaa cag atg tgt cct att tgc<br>Ser Glu Asn Ser Ile Lys Asp Glu Glu Glu Gln Met Cys Pro Ile Cys<br>435 440 445 | 1344 |
| ttg ttg ggc atg ctt gat gaa gaa agt ctt aca gtg tgt gaa gac ggc<br>Leu Leu Gly Met Leu Asp Glu Glu Ser Leu Thr Val Cys Glu Asp Gly<br>450 455 460 | 1392 |
| tgc agg aac aag ctg cac cac cac tgc atg tca att tgg gca gaa gag<br>Cys Arg Asn Lys Leu His His His Cys Met Ser Ile Trp Ala Glu Glu<br>465 470 475 | 1440 |
| tgt aga aga aat aga gaa cct tta ata tgt ccc ctt tgt aga tct aag<br>Cys Arg Arg Asn Arg Glu Pro Leu Ile Cys Pro Leu Cys Arg Ser Lys<br>480 485 490 | 1488 |
| tgg aga tct cat gat ttc tac agc cac gag ttg tca agt cct gtg gat<br>Trp Arg Ser His Asp Phe Tyr Ser His Glu Leu Ser Ser Pro Val Asp<br>495 500 505 510 | 1536 |
| tcc cct tct tcc ctc aga gct gca cag cag caa acc gta cag cag cag<br>Ser Pro Ser Ser Leu Arg Ala Ala Gln Gln Gln Thr Val Gln Gln Gln<br>515 520 525 | 1584 |
| cct ttg gct gga tca cga agg aat caa gag agc aat ttt aac ctt act<br>Pro Leu Ala Gly Ser Arg Arg Asn Gln Glu Ser Asn Phe Asn Leu Thr | 1632 |

-continued

```
                530                 535                 540
cat tat gga act cag caa atc cct cct gct tac aaa gat tta gct gag      1680
His Tyr Gly Thr Gln Gln Ile Pro Pro Ala Tyr Lys Asp Leu Ala Glu
            545                 550                 555 cca tgg att cag gtg ttt gga atg gaa ctc gtt ggc tgc tta ttt tct      1728
Pro Trp Ile Gln Val Phe Gly Met Glu Leu Val Gly Cys Leu Phe Ser
560                 565                 570 aga aac tgg aat gtg aga gag atg gcc ctc agg cgt ctt tcc cat gat      1776
Arg Asn Trp Asn Val Arg Glu Met Ala Leu Arg Arg Leu Ser His Asp
575                 580                 585                 590 gtc agt ggg gcc ctg ctg ttg gca aat ggg gag agc act gga aat tct      1824
Val Ser Gly Ala Leu Leu Leu Ala Asn Gly Glu Ser Thr Gly Asn Ser
                595                 600                 605 ggg ggc agc agt gga agc agc ccg agt ggg gga gcc acc agt ggg tct      1872
Gly Gly Ser Ser Gly Ser Ser Pro Ser Gly Gly Ala Thr Ser Gly Ser
            610                 615                 620 tcc cag acc agt atc tca gga gat gtg gtg gag gca tgc tgc agc gtt      1920
Ser Gln Thr Ser Ile Ser Gly Asp Val Val Glu Ala Cys Cys Ser Val
        625                 630                 635 ctg tca atg gtc tgt gct gac cct gtc tac aaa gtg tac gtt gct gct      1968
Leu Ser Met Val Cys Ala Asp Pro Val Tyr Lys Val Tyr Val Ala Ala
    640                 645                 650 tta aaa aca ttg aga gcc atg ctg gta tat act cct tgc cac agt tta      2016
Leu Lys Thr Leu Arg Ala Met Leu Val Tyr Thr Pro Cys His Ser Leu
655                 660                 665                 670 gcg gaa aga atc aaa ctt cag aga ctt ctc cag cca gtt gta gac acc      2064
Ala Glu Arg Ile Lys Leu Gln Arg Leu Leu Gln Pro Val Val Asp Thr
                675                 680                 685 atc cta gtc aaa tgt gca gat gcc aat agc cgc aca agt cag ctg tcc      2112
Ile Leu Val Lys Cys Ala Asp Ala Asn Ser Arg Thr Ser Gln Leu Ser
            690                 695                 700 ata tca aca ctg ttg gaa ctg tgc aaa ggc caa gca gga gag ttg gca      2160
Ile Ser Thr Leu Leu Glu Leu Cys Lys Gly Gln Ala Gly Glu Leu Ala
        705                 710                 715 gtt ggc aga gaa ata cta aaa gct gga tcc att ggt att ggt ggt gtt      2208
Val Gly Arg Glu Ile Leu Lys Ala Gly Ser Ile Gly Ile Gly Gly Val
    720                 725                 730 gat tat gtc tta aat tgt att ctt gga aac caa act gaa tca aac aat      2256
Asp Tyr Val Leu Asn Cys Ile Leu Gly Asn Gln Thr Glu Ser Asn Asn
735                 740                 745                 750 tgg caa gaa ctt ctt ggc cgc ctt tgt ctt ata gat aga ctg ttg ttg      2304
Trp Gln Glu Leu Leu Gly Arg Leu Cys Leu Ile Asp Arg Leu Leu Leu
                755                 760                 765 gaa ttt cct gct gaa ttt tat cct cat att gtc agt act gat gtt tca      2352
Glu Phe Pro Ala Glu Phe Tyr Pro His Ile Val Ser Thr Asp Val Ser
            770                 775                 780 caa gct gag cct gtt gaa atc agg tat aag aag ctg ctg tcc ctc tta      2400
Gln Ala Glu Pro Val Glu Ile Arg Tyr Lys Lys Leu Leu Ser Leu Leu
        785                 790                 795 acc ttt gct ttg cag tcc att gat aat tcc cac tca atg gtt ggc aaa      2448
Thr Phe Ala Leu Gln Ser Ile Asp Asn Ser His Ser Met Val Gly Lys
    800                 805                 810 ctt tcc aga agg atc tac ttg agt tct gca aga atg gtt act aca gta      2496
Leu Ser Arg Arg Ile Tyr Leu Ser Ser Ala Arg Met Val Thr Thr Val
815                 820                 825                 830 ccc cat gtg ttt tca aaa ctg tta gaa atg ctg agt gtt tcc agt tcc      2544
Pro His Val Phe Ser Lys Leu Leu Glu Met Leu Ser Val Ser Ser Ser
                835                 840                 845 act cac ttc acc agg atg cgt cgc cgt ttg atg gct att gca gat gag      2592
```

```
                Thr His Phe Thr Arg Met Arg Arg Arg Leu Met Ala Ile Ala Asp Glu
                                850             855                 860 gtg gaa att gcc gaa gcc atc cag ttg ggc gta gaa gac act ttg gat                 2640
Val Glu Ile Ala Glu Ala Ile Gln Leu Gly Val Glu Asp Thr Leu Asp
        865                 870                 875 ggt caa cag gac agc ttc ttg cag gca tct gtt ccc aac aac tat ctg                 2688
Gly Gln Gln Asp Ser Phe Leu Gln Ala Ser Val Pro Asn Asn Tyr Leu
    880                 885                 890 gaa acc aca gag aac agt tcc cct gag tgc aca gtc cat tta gag aaa                 2736
Glu Thr Thr Glu Asn Ser Ser Pro Glu Cys Thr Val His Leu Glu Lys
895                 900                 905                 910 act gga aaa gga tta tgt gct aca aaa ttg agt gcc agt tca gag gac                 2784
Thr Gly Lys Gly Leu Cys Ala Thr Lys Leu Ser Ala Ser Ser Glu Asp
                915                 920                 925 att tct gag aga ctg gcc agc att tca gta gga cct tct agt tca aca                 2832
Ile Ser Glu Arg Leu Ala Ser Ile Ser Val Gly Pro Ser Ser Ser Thr
            930                 935                 940 aca aca aca aca aca aca gag caa cca aag cca atg gtt caa aca                     2880
Thr Thr Thr Thr Thr Thr Glu Gln Pro Lys Pro Met Val Gln Thr
        945                 950                 955 aaa ggc aga ccc cac agt cag tgt ttg aac tcc tct cct tta tct cat                 2928
Lys Gly Arg Pro His Ser Gln Cys Leu Asn Ser Ser Pro Leu Ser His
    960                 965                 970 cat tcc caa tta atg ttt cca gcc ttg tca acc cct tct tct tct acc                 2976
His Ser Gln Leu Met Phe Pro Ala Leu Ser Thr Pro Ser Ser Ser Thr
975                 980                 985                 990 cca tct gta cca gct ggc act gca aca gat gtc tct aag cat aga  ctt                3024
Pro Ser Val Pro Ala Gly Thr Ala Thr Asp Val Ser Lys His Arg  Leu
                995                 1000                1005 cag gga ttc att  ccc tgc aga ata cct  tct gca tct cct caa  aca                  3069
Gln Gly Phe Ile Pro Cys Arg Ile Pro  Ser Ala Ser Pro Gln  Thr
            1010                1015                1020 cag cgc aag ttt  tct cta caa ttc cac  aga aac tgt cct gaa  aac                  3114
Gln Arg Lys Phe Ser Leu Gln Phe His  Arg Asn Cys Pro Glu  Asn
        1025                1030                1035 aaa gac tca gat  aaa ctt tcc cca gtc  ttt act cag tca aga  ccc                  3159
Lys Asp Ser Asp Lys Leu Ser Pro Val  Phe Thr Gln Ser Arg  Pro
    1040                1045                1050 ttg ccc tcc agt  aac ata cac agg cca  aag cca tct aga cct  acc                  3204
Leu Pro Ser Ser Asn Ile His Arg Pro  Lys Pro Ser Arg Pro  Thr
    1055                1060                1065 cca gtt aat aca  agt aaa cag gga gat  ccc tca aaa aat agc  atg                  3249
Pro Gly Asn Thr Ser Lys Gln Gly Asp  Pro Ser Lys Asn Ser  Met
    1070                1075                1080 aca ctt gat ctg  aac agt agt tcc aaa  tgt gat gac agc ttt  ggc                  3294
Thr Leu Asp Leu Asn Ser Ser Ser Lys  Cys Asp Asp Ser Phe  Gly
    1085                1090                1095 tgt agc agc aat  agt agt aat gct gtt  ata ccc agt gac gag  aca                  3339
Cys Ser Ser Asn Ser Ser Asn Ala Val  Ile Pro Ser Asp Glu  Thr
    1100                1105                1110 gtg ttc acc cca  gta gag gag aaa tgc  aga tta gat gtc aat  aca                  3384
Val Phe Thr Pro Val Glu Glu Lys Cys  Arg Leu Asp Val Asn  Thr
    1115                1120                1125 gag ctc aac tcc  agt att gag gac ctt  ctt gaa gca tct atg  cct                  3429
Glu Leu Asn Ser Ser Ile Glu Asp Leu  Leu Glu Ala Ser Met  Pro
    1130                1135                1140 tca agt gat aca  aca gta act ttt aag  tca gaa gtt gct gtc  ctg                  3474
Ser Ser Asp Thr Thr Val Thr Phe Lys  Ser Glu Val Ala Val  Leu
    1145                1150                1155
```

```
tct cct gaa aag gct gaa aat gat gat acc tac aaa gat gat gtg    3519
Ser Pro Glu Lys Ala Glu Asn Asp Asp Thr Tyr Lys Asp Asp Val
         1160                1165                1170 aat cat aat caa aag tgc aaa gag aag atg gaa gct gaa gaa gaa    3564
Asn His Asn Gln Lys Cys Lys Glu Lys Met Glu Ala Glu Glu Glu
         1175                1180                1185 gaa gct tta gca att gcc atg gca atg tca gcg tct cag gat gcc    3609
Glu Ala Leu Ala Ile Ala Met Ala Met Ser Ala Ser Gln Asp Ala
         1190                1195                1200 ctc ccc ata gtt cct cag ctg cag gtt gaa aat gga gaa gat atc    3654
Leu Pro Ile Val Pro Gln Leu Gln Val Glu Asn Gly Glu Asp Ile
         1205                1210                1215 atc att att caa cag gat aca cca gag act cta cca gga cat acc    3699
Ile Ile Ile Gln Gln Asp Thr Pro Glu Thr Leu Pro Gly His Thr
         1220                1225                1230 aaa gca aaa caa ccg tat aga gaa gac act gaa tgg ctg aaa ggt    3744
Lys Ala Lys Gln Pro Tyr Arg Glu Asp Thr Glu Trp Leu Lys Gly
         1235                1240                1245 caa cag ata ggc ctt gga gca ttt tct tct tgt tat cag gct caa    3789
Gln Gln Ile Gly Leu Gly Ala Phe Ser Ser Cys Tyr Gln Ala Gln
         1250                1255                1260 gat gtg gga act gga act tta atg gct gtt aaa cag gtg act tat    3834
Asp Val Gly Thr Gly Thr Leu Met Ala Val Lys Gln Val Thr Tyr
         1265                1270                1275 gtc aga aac aca tct tct gag caa gaa gaa gta gta gaa gca cta    3879
Val Arg Asn Thr Ser Ser Glu Gln Glu Glu Val Val Glu Ala Leu
         1280                1285                1290 aga gaa gag ata aga atg atg agc cat ctg aat cat cca aac atc    3924
Arg Glu Glu Ile Arg Met Met Ser His Leu Asn His Pro Asn Ile
         1295                1300                1305 att agg atg ttg gga gcc acg tgt gag aag agc aat tac aat ctc    3969
Ile Arg Met Leu Gly Ala Thr Cys Glu Lys Ser Asn Tyr Asn Leu
         1310                1315                1320 ttc att gaa tgg atg gca ggg gga tcg gtg gct cat ttg ctg agt    4014
Phe Ile Glu Trp Met Ala Gly Gly Ser Val Ala His Leu Leu Ser
         1325                1330                1335 aaa tat gga gcc ttc aaa gaa tca gta gtt att aac tac act gaa    4059
Lys Tyr Gly Ala Phe Lys Glu Ser Val Val Ile Asn Tyr Thr Glu
         1340                1345                1350 cag tta ctc cgt ggc ctt tcg tat ctc cat gaa aac caa atc att    4104
Gln Leu Leu Arg Gly Leu Ser Tyr Leu His Glu Asn Gln Ile Ile
         1355                1360                1365 cac aga gat gtc aaa ggt gcc aat ttg cta att gac agc act ggt    4149
His Arg Asp Val Lys Gly Ala Asn Leu Leu Ile Asp Ser Thr Gly
         1370                1375                1380 cag aga cta aga att gca gat ttt gga gct gca gcc agg ttg gca    4194
Gln Arg Leu Arg Ile Ala Asp Phe Gly Ala Ala Ala Arg Leu Ala
         1385                1390                1395 tca aaa gga act ggt gca gga gag ttt cag gga caa tta ctg ggg    4239
Ser Lys Gly Thr Gly Ala Gly Glu Phe Gln Gly Gln Leu Leu Gly
         1400                1405                1410 aca att gca ttt atg gca cct gag gta cta aga ggt caa cag tat    4284
Thr Ile Ala Phe Met Ala Pro Glu Val Leu Arg Gly Gln Gln Tyr
         1415                1420                1425 gga agg agc tgt gat gta tgg agt gtt ggc tgt gct att ata gaa    4329
Gly Arg Ser Cys Asp Val Trp Ser Val Gly Cys Ala Ile Ile Glu
         1430                1435                1440 atg gct tgt gca aaa cca cca tgg aat gca gaa aaa cac tcc aat    4374
Met Ala Cys Ala Lys Pro Pro Trp Asn Ala Glu Lys His Ser Asn
         1445                1450                1455
```

-continued

```
cat ctt gct ttg  ata ttt aag att gct  agt gca act act gct  cca              4419
His Leu Ala Leu  Ile Phe Lys Ile Ala  Ser Ala Thr Thr Ala  Pro
             1460             1465                 1470 tcg atc cct tca  cat ttg tct cct ggt  tta cga gat gtg gct  ctt              4464
Ser Ile Pro Ser  His Leu Ser Pro Gly  Leu Arg Asp Val Ala  Leu
     1475                 1480                 1485 cgt tgt tta gaa  ctt caa cct cag gac  aga cct cca tca aga  gag              4509
Arg Cys Leu Glu  Leu Gln Pro Gln Asp  Arg Pro Pro Ser Arg  Glu
         1490                 1495                 1500 cta ctg aag cat  cca gtc ttt cgt act  aca tgg tag ccaattatgc                4555
Leu Leu Lys His  Pro Val Phe Arg Thr  Thr Trp
             1505             1510 agatcaacta cagtagaaac aggatgctca acaagagaaa aaaaacttgt ggggaaccac           4615
attgatattc tactggccat gatgccactg aacagctatg aacgaggcca gtggggaacc           4675
cttacctaag tatgtgattg acaaatcatg atctgtacct aagctcagta tgcaaaagcc           4735
caaactagtg cagaaactgt aaactgtgcc tttcaaagaa ctggccctag gtgaacagga           4795
aaacaatgaa gtttgcatga ctaaattgca gaagcataat tttattttt tggagcactt            4855 tttcagcaat attagcggct gagggctca ggatctattt taatatttca attattcttc            4915
catttcatat agtgatcaca agcagggggt tctgcaattc cgttcaaatt ttttgtcact           4975
ggctataaaa tcagtatctg cctcttttag gtcagagtat gctatgagta gcaatacata           5035
catatatttt taaaagttga tacttcttta tgacccacag ttgaccttta ttttcttaaa           5095
taccagggca gttgtggctc attgtgcatt ttactgttgg cccattcatt tcgtttttgg           5155
aaattatggt tttgtatttt catgtttatt tacattcatt tttgtttatt cagggaaagc           5215
tgatcttttt tttcaaacca aaaaaaaaa                                             5245
```

<210> SEQ ID NO 2
<211> LENGTH: 1512
<212> TYPE: PRT
<213> ORGANISM: Human

<400> SEQUENCE: 2

```
Met Ala Ala Ala Gly Asn Arg Ala Ser Ser Ser Gly Phe Pro Gly
1               5                  10                  15

Ala Arg Ala Thr Ser Pro Glu Ala Gly Gly Gly Gly Ala Leu Lys
                20                  25                  30

Ala Ser Ser Ala Pro Ala Ala Ala Gly Leu Leu Arg Glu Ala Gly
            35                  40                  45

Ser Gly Gly Arg Glu Arg Ala Asp Trp Arg Arg Gln Leu Arg Lys
        50                  55                  60

Val Arg Ser Val Glu Leu Asp Gln Leu Pro Glu Gln Pro Leu Phe Leu
65                  70                  75                  80

Ala Ala Ser Pro Pro Ala Ser Ser Thr Ser Pro Ser Pro Glu Pro Ala
                85                  90                  95

Asp Ala Ala Gly Ser Gly Thr Gly Phe Gln Pro Val Ala Val Pro Pro
                100                 105                 110

Pro His Gly Ala Ala Ser Arg Gly Gly Ala His Leu Thr Glu Ser Val
            115                 120                 125

Ala Ala Pro Asp Ser Gly Ala Ser Ser Pro Ala Ala Glu Pro Gly
        130                 135                 140

Glu Lys Arg Ala Pro Ala Ala Glu Pro Ser Pro Ala Ala Ala Pro Ala
145                 150                 155                 160
```

-continued

```
Gly Arg Glu Met Glu Asn Lys Glu Thr Leu Lys Gly Leu His Lys Met
                165                 170                 175
Asp Asp Arg Pro Glu Arg Met Ile Arg Glu Lys Leu Lys Ala Thr
            180                 185                 190
Cys Met Pro Ala Trp Lys His Glu Trp Leu Glu Arg Arg Asn Arg Arg
            195                 200                 205
Gly Pro Val Val Val Lys Pro Ile Pro Val Lys Gly Asp Gly Ser Glu
            210                 215                 220
Met Asn His Leu Ala Ala Glu Ser Pro Gly Glu Val Gln Ala Ser Ala
225                 230                 235                 240
Ala Ser Pro Ala Ser Lys Gly Arg Arg Ser Pro Ser Pro Gly Asn Ser
                245                 250                 255
Pro Ser Gly Arg Thr Val Lys Ser Glu Ser Pro Gly Val Arg Arg Lys
                260                 265                 270
Arg Val Ser Pro Val Pro Phe Gln Ser Gly Arg Ile Thr Pro Pro Arg
            275                 280                 285
Arg Ala Pro Ser Pro Asp Gly Phe Ser Pro Tyr Ser Pro Glu Glu Thr
            290                 295                 300
Asn Arg Arg Val Asn Lys Val Met Arg Ala Arg Leu Tyr Leu Leu Gln
305                 310                 315                 320
Gln Ile Gly Pro Asn Ser Phe Leu Ile Gly Gly Asp Ser Pro Asp Asn
                325                 330                 335
Lys Tyr Arg Val Phe Ile Gly Pro Gln Asn Cys Ser Cys Ala Arg Gly
                340                 345                 350
Thr Phe Cys Ile His Leu Leu Phe Val Met Leu Arg Val Phe Gln Leu
            355                 360                 365
Glu Pro Ser Asp Pro Met Leu Trp Arg Lys Thr Leu Lys Asn Phe Glu
            370                 375                 380
Val Glu Ser Leu Phe Gln Lys Tyr His Ser Arg Arg Ser Ser Arg Ile
385                 390                 395                 400
Lys Ala Pro Ser Arg Asn Thr Ile Gln Lys Phe Val Ser Arg Met Ser
                405                 410                 415
Asn Ser His Thr Leu Ser Ser Ser Ser Thr Ser Thr Ser Ser Ser Glu
            420                 425                 430
Asn Ser Ile Lys Asp Glu Glu Gln Met Cys Pro Ile Cys Leu Leu
            435                 440                 445
Gly Met Leu Asp Glu Glu Ser Leu Thr Val Cys Glu Asp Gly Cys Arg
450                 455                 460
Asn Lys Leu His His His Cys Met Ser Ile Trp Ala Glu Glu Cys Arg
465                 470                 475                 480
Arg Asn Arg Glu Pro Leu Ile Cys Pro Leu Cys Arg Ser Lys Trp Arg
                485                 490                 495
Ser His Asp Phe Tyr Ser His Glu Leu Ser Ser Pro Val Asp Ser Pro
            500                 505                 510
Ser Ser Leu Arg Ala Ala Gln Gln Thr Val Gln Gln Pro Leu
            515                 520                 525
Ala Gly Ser Arg Arg Asn Gln Glu Ser Asn Phe Asn Leu Thr His Tyr
            530                 535                 540
Gly Thr Gln Gln Ile Pro Pro Ala Tyr Lys Asp Leu Ala Glu Pro Trp
545                 550                 555                 560
Ile Gln Val Phe Gly Met Glu Leu Val Gly Cys Leu Phe Ser Arg Asn
                565                 570                 575
Trp Asn Val Arg Glu Met Ala Leu Arg Arg Leu Ser His Asp Val Ser
```

-continued

```
              580                 585                 590
Gly Ala Leu Leu Ala Asn Gly Glu Ser Thr Gly Asn Ser Gly Gly
            595                 600                 605

Ser Ser Gly Ser Ser Pro Ser Gly Gly Ala Thr Ser Gly Ser Ser Gln
        610                 615                 620

Thr Ser Ile Ser Gly Asp Val Val Glu Ala Cys Cys Ser Val Leu Ser
625                 630                 635                 640

Met Val Cys Ala Asp Pro Val Tyr Lys Val Tyr Val Ala Ala Leu Lys
                    645                 650                 655

Thr Leu Arg Ala Met Leu Val Tyr Thr Pro Cys His Ser Leu Ala Glu
            660                 665                 670

Arg Ile Lys Leu Gln Arg Leu Leu Gln Pro Val Val Asp Thr Ile Leu
        675                 680                 685

Val Lys Cys Ala Asp Ala Asn Ser Arg Thr Ser Gln Leu Ser Ile Ser
    690                 695                 700

Thr Leu Leu Glu Leu Cys Lys Gly Gln Ala Gly Glu Leu Ala Val Gly
705                 710                 715                 720

Arg Glu Ile Leu Lys Ala Gly Ser Ile Gly Ile Gly Gly Val Asp Tyr
                    725                 730                 735

Val Leu Asn Cys Ile Leu Gly Asn Gln Thr Glu Ser Asn Asn Trp Gln
            740                 745                 750

Glu Leu Leu Gly Arg Leu Cys Leu Ile Asp Arg Leu Leu Leu Glu Phe
        755                 760                 765

Pro Ala Glu Phe Tyr Pro His Ile Val Ser Thr Asp Val Ser Gln Ala
770                 775                 780

Glu Pro Val Glu Ile Arg Tyr Lys Lys Leu Leu Ser Leu Leu Thr Phe
785                 790                 795                 800

Ala Leu Gln Ser Ile Asp Asn Ser His Ser Met Val Gly Lys Leu Ser
                    805                 810                 815

Arg Arg Ile Tyr Leu Ser Ser Ala Arg Met Val Thr Val Pro His
            820                 825                 830

Val Phe Ser Lys Leu Leu Glu Met Leu Ser Val Ser Ser Ser Thr His
        835                 840                 845

Phe Thr Arg Met Arg Arg Arg Leu Met Ala Ile Ala Asp Glu Val Glu
850                 855                 860

Ile Ala Glu Ala Ile Gln Leu Gly Val Glu Asp Thr Leu Asp Gly Gln
865                 870                 875                 880

Gln Asp Ser Phe Leu Gln Ala Ser Val Pro Asn Asn Tyr Leu Glu Thr
                    885                 890                 895

Thr Glu Asn Ser Ser Pro Glu Cys Thr Val His Leu Glu Lys Thr Gly
            900                 905                 910

Lys Gly Leu Cys Ala Thr Lys Leu Ser Ala Ser Ser Glu Asp Ile Ser
        915                 920                 925

Glu Arg Leu Ala Ser Ile Ser Val Gly Pro Ser Ser Ser Thr Thr Thr
    930                 935                 940

Thr Thr Thr Thr Thr Glu Gln Pro Lys Pro Met Val Gln Thr Lys Gly
945                 950                 955                 960

Arg Pro His Ser Gln Cys Leu Asn Ser Pro Leu Ser His Ser
                965                 970                 975

Gln Leu Met Phe Pro Ala Leu Ser Thr Pro Ser Ser Thr Pro Ser
            980                 985                 990

Val Pro Ala Gly Thr Ala Thr Asp  Val Ser Lys His Arg  Leu Gln Gly
        995                 1000                 1005
```

-continued

```
Phe Ile Pro Cys Arg Ile Pro Ser Ala Ser Pro Gln Thr Gln Arg
    1010                1015                1020
Lys Phe Ser Leu Gln Phe His Arg Asn Cys Pro Glu Asn Lys Asp
    1025                1030                1035
Ser Asp Lys Leu Ser Pro Val Phe Thr Gln Ser Arg Pro Leu Pro
    1040                1045                1050
Ser Ser Asn Ile His Arg Pro Lys Pro Ser Arg Pro Thr Pro Gly
    1055                1060                1065
Asn Thr Ser Lys Gln Gly Asp Pro Ser Lys Asn Ser Met Thr Leu
    1070                1075                1080
Asp Leu Asn Ser Ser Lys Cys Asp Ser Phe Gly Cys Ser
    1085                1090                1095
Ser Asn Ser Ser Asn Ala Val Ile Pro Ser Asp Glu Thr Val Phe
    1100                1105                1110
Thr Pro Val Glu Glu Lys Cys Arg Leu Asp Val Asn Thr Glu Leu
    1115                1120                1125
Asn Ser Ser Ile Glu Asp Leu Leu Glu Ala Ser Met Pro Ser Ser
    1130                1135                1140
Asp Thr Thr Val Thr Phe Lys Ser Glu Val Ala Val Leu Ser Pro
    1145                1150                1155
Glu Lys Ala Glu Asn Asp Asp Thr Tyr Lys Asp Asp Val Asn His
    1160                1165                1170
Asn Gln Lys Cys Lys Glu Lys Met Glu Ala Glu Glu Glu Ala
    1175                1180                1185
Leu Ala Ile Ala Met Ala Met Ser Ala Ser Gln Asp Ala Leu Pro
    1190                1195                1200
Ile Val Pro Gln Leu Gln Val Glu Asn Gly Glu Asp Ile Ile Ile
    1205                1210                1215
Ile Gln Gln Asp Thr Pro Glu Thr Leu Pro Gly His Thr Lys Ala
    1220                1225                1230
Lys Gln Pro Tyr Arg Glu Asp Thr Glu Trp Leu Lys Gly Gln Gln
    1235                1240                1245
Ile Gly Leu Gly Ala Phe Ser Ser Cys Tyr Gln Ala Gln Asp Val
    1250                1255                1260
Gly Thr Gly Thr Leu Met Ala Val Lys Gln Val Thr Tyr Val Arg
    1265                1270                1275
Asn Thr Ser Ser Glu Gln Glu Glu Val Val Glu Ala Leu Arg Glu
    1280                1285                1290
Glu Ile Arg Met Met Ser His Leu Asn His Pro Asn Ile Ile Arg
    1295                1300                1305
Met Leu Gly Ala Thr Cys Glu Lys Ser Asn Tyr Asn Leu Phe Ile
    1310                1315                1320
Glu Trp Met Ala Gly Gly Ser Val Ala His Leu Leu Ser Lys Tyr
    1325                1330                1335
Gly Ala Phe Lys Glu Ser Val Val Ile Asn Tyr Thr Glu Gln Leu
    1340                1345                1350
Leu Arg Gly Leu Ser Tyr Leu His Glu Asn Gln Ile Ile His Arg
    1355                1360                1365
Asp Val Lys Gly Ala Asn Leu Leu Ile Asp Ser Thr Gly Gln Arg
    1370                1375                1380
Leu Arg Ile Ala Asp Phe Gly Ala Ala Ala Arg Leu Ala Ser Lys
    1385                1390                1395
```

```
Gly Thr Gly Ala Gly Glu Phe Gln Gly Gln Leu Leu Gly Thr Ile
1400                 1405                 1410

Ala Phe Met Ala Pro Glu Val Leu Arg Gly Gln Gln Tyr Gly Arg
    1415                 1420                 1425

Ser Cys Asp Val Trp Ser Val Gly Cys Ala Ile Ile Glu Met Ala
    1430                 1435                 1440

Cys Ala Lys Pro Pro Trp Asn Ala Glu Lys His Ser Asn His Leu
    1445                 1450                 1455

Ala Leu Ile Phe Lys Ile Ala Ser Ala Thr Thr Ala Pro Ser Ile
    1460                 1465                 1470

Pro Ser His Leu Ser Pro Gly Leu Arg Asp Val Ala Leu Arg Cys
    1475                 1480                 1485

Leu Glu Leu Gln Pro Gln Asp Arg Pro Pro Ser Arg Glu Leu Leu
    1490                 1495                 1500

Lys His Pro Val Phe Arg Thr Thr Trp
    1505                 1510

<210> SEQ ID NO 3
<211> LENGTH: 1495
<212> TYPE: PRT
<213> ORGANISM: partial human MEKK1 protein

<400> SEQUENCE: 3

Pro Ser Pro Glu Ala Gly Gly Gly Gly Ala Leu Lys Ala Ser Ser
1               5                   10                  15

Ala Arg Ala Ala Ala Gly Leu Leu Arg Glu Ala Gly Ser Gly Gly
            20                  25                  30

Arg Glu Arg Ala Asp Trp Arg Arg Gln Leu Arg Lys Val Arg Ser
        35                  40                  45

Val Glu Leu Asp Gln Leu Pro Glu Gln Pro Leu Phe Leu Ala Ala Ser
    50                  55                  60

Pro Pro Ala Ser Ser Thr Ser Pro Ser Pro Glu Pro Ala Asp Ala Ala
65                  70                  75                  80

Gly Ser Gly Thr Gly Phe Gln Pro Val Ala Val Pro Pro Pro His Gly
                85                  90                  95

Ala Ala Ser Arg Arg Gly Ala His Leu Thr Glu Ser Val Ala Ala Pro
                100                 105                 110

Asp Ser Gly Ala Ser Ser Pro Ala Ala Ala Glu Pro Gly Glu Lys Arg
            115                 120                 125

Ala Pro Ala Ala Glu Pro Ser Pro Ala Ala Ala Pro Ala Gly Arg Glu
            130                 135                 140

Met Glu Asn Lys Glu Thr Leu Lys Gly Leu His Lys Met Asp Asp Arg
145                 150                 155                 160

Pro Glu Glu Arg Met Ile Arg Glu Lys Leu Lys Ala Thr Cys Met Pro
                165                 170                 175

Ala Trp Lys His Glu Trp Leu Glu Arg Arg Asn Arg Arg Gly Pro Val
            180                 185                 190

Val Val Lys Pro Ile Pro Val Lys Gly Asp Gly Ser Glu Met Asn His
        195                 200                 205

Leu Ala Ala Glu Ser Pro Gly Glu Val Gln Ala Ser Ala Ala Ser Pro
    210                 215                 220

Ala Ser Lys Gly Arg Arg Ser Pro Ser Pro Gly Asn Ser Pro Ser Gly
225                 230                 235                 240

Arg Thr Val Lys Ser Glu Ser Pro Gly Val Arg Arg Lys Arg Val Ser
                245                 250                 255
```

```
Pro Val Pro Phe Gln Ser Gly Arg Ile Thr Pro Pro Arg Arg Ala Pro
        260                 265                 270

Ser Pro Asp Gly Phe Ser Pro Tyr Ser Pro Glu Glu Thr Asn Arg Arg
        275                 280                 285

Val Asn Lys Val Met Arg Ala Arg Leu Tyr Leu Leu Gln Gln Ile Gly
        290                 295                 300

Pro Asn Ser Phe Leu Ile Gly Gly Asp Ser Pro Asp Asn Lys Tyr Arg
305                 310                 315                 320

Val Phe Ile Gly Pro Gln Asn Cys Ser Cys Ala His Gly Thr Phe Cys
                325                 330                 335

Ile His Leu Leu Phe Val Met Leu Arg Val Phe Gln Leu Glu Pro Ser
                340                 345                 350

Asp Pro Met Leu Trp Arg Lys Thr Leu Lys Asn Phe Glu Val Glu Ser
                355                 360                 365

Leu Phe Gln Lys Tyr His Ser Arg Arg Ser Ser Arg Ile Lys Ala Pro
        370                 375                 380

Ser Arg Asn Thr Ile Gln Lys Phe Val Ser Arg Met Ser Asn Ser His
385                 390                 395                 400

Thr Leu Ser Ser Ser Ser Thr Ser Thr Ser Ser Glu Asn Ser Ile
                405                 410                 415

Lys Asp Glu Glu Glu Gln Met Cys Pro Ile Cys Leu Leu Gly Met Leu
                420                 425                 430

Asp Glu Glu Ser Leu Thr Val Cys Glu Asp Gly Cys Arg Asn Lys Leu
                435                 440                 445

His His His Cys Met Ser Ile Trp Ala Glu Glu Cys Arg Arg Asn Arg
        450                 455                 460

Glu Pro Leu Ile Cys Pro Leu Cys Arg Ser Lys Trp Arg Ser His Asp
465                 470                 475                 480

Phe Tyr Ser His Glu Leu Ser Ser Pro Val Asp Ser Pro Ser Ser Leu
                485                 490                 495

Arg Ala Ala Gln Gln Gln Thr Val Gln Gln Gln Pro Leu Ala Gly Ser
                500                 505                 510

Arg Arg Asn Gln Glu Ser Asn Phe Asn Leu Thr His Tyr Gly Thr Gln
        515                 520                 525

Gln Ile Pro Pro Ala Tyr Lys Asp Leu Ala Glu Pro Trp Ile Gln Val
        530                 535                 540

Phe Gly Met Glu Leu Val Gly Cys Leu Phe Ser Arg Asn Trp Asn Val
545                 550                 555                 560

Arg Glu Met Ala Leu Arg Arg Leu Ser His Asp Val Ser Gly Ala Leu
                565                 570                 575

Leu Leu Ala Asn Gly Glu Ser Thr Gly Asn Ser Gly Gly Ser Ser Gly
                580                 585                 590

Ser Ser Pro Ser Gly Gly Ala Thr Ser Gly Ser Ser Gln Thr Ser Ile
        595                 600                 605

Ser Gly Asp Val Val Glu Ala Cys Cys Ser Val Leu Ser Met Val Cys
        610                 615                 620

Ala Asp Pro Val Tyr Lys Val Tyr Val Ala Ala Leu Lys Thr Leu Arg
625                 630                 635                 640

Ala Met Leu Val Tyr Thr Pro Cys His Ser Leu Ala Glu Arg Ile Lys
                645                 650                 655

Leu Gln Arg Leu Leu Gln Pro Val Val Asp Thr Ile Leu Val Lys Cys
        660                 665                 670
```

-continued

```
Ala Asp Ala Asn Ser Arg Thr Ser Gln Leu Ser Ile Ser Thr Leu Leu
            675                 680                 685

Glu Leu Cys Lys Gly Gln Ala Gly Glu Leu Ala Val Gly Arg Glu Ile
        690                 695                 700

Leu Lys Ala Gly Ser Ile Gly Ile Gly Gly Val Asp Tyr Val Leu Asn
705                 710                 715                 720

Cys Ile Leu Gly Asn Gln Thr Glu Ser Asn Asn Trp Gln Glu Leu Leu
                725                 730                 735

Gly Arg Leu Cys Leu Ile Asp Arg Leu Leu Glu Phe Pro Ala Glu
                740                 745                 750

Phe Tyr Pro His Ile Val Ser Thr Asp Val Ser Gln Ala Glu Pro Val
        755                 760                 765

Glu Ile Arg Tyr Lys Lys Leu Leu Ser Leu Leu Thr Phe Ala Leu Gln
    770                 775                 780

Ser Ile Asp Asn Ser His Ser Met Val Gly Lys Leu Ser Arg Arg Ile
785                 790                 795                 800

Tyr Leu Ser Ser Ala Arg Met Val Thr Thr Val Pro His Val Phe Ser
                805                 810                 815

Lys Leu Leu Glu Met Leu Ser Val Ser Ser Val Ser Thr His Phe Thr
            820                 825                 830

Arg Met Arg Arg Arg Leu Met Ala Tyr Ala Asp Glu Val Glu Ile Ala
        835                 840                 845

Glu Ala Ile Gln Leu Gly Val Glu Asp Thr Leu Gln Arg Gln His
    850                 855                 860

Asn Ser Phe Cys Arg His Leu Phe Pro Thr Thr Ile Trp Lys Pro Gln
865                 870                 875                 880

Arg Thr Val Pro Leu Glu Cys Thr Val His Leu Glu Lys Thr Gly Lys
                885                 890                 895

Gly Leu Cys Ala Thr Lys Leu Ser Ala Ser Ser Glu Asp Ile Ser Glu
            900                 905                 910

Arg Leu Ala Arg Ile Ser Val Gly Pro Ser Ser Thr Thr Thr Thr
        915                 920                 925

Thr Thr Thr Thr Glu Gln Pro Lys Pro Met Val Gln Thr Lys Gly Arg
930                 935                 940

Pro His Ser Gln Cys Leu Asn Ser Ser Pro Leu Ser His His Ser Gln
945                 950                 955                 960

Leu Met Phe Pro Ala Leu Ser Thr Pro Ser Ser Ser Thr Pro Ser Val
            965                 970                 975

Pro Ala Gly Thr Ala Thr Asp Val Ser Lys His Arg Leu Gln Gly Phe
        980                 985                 990

Ile Pro Cys Arg Ile Pro Ser Ala Ser Pro Gln Thr Gln Arg Lys Phe
    995                 1000                1005

Ser Leu Gln Phe His Arg Asn Cys Pro Glu Asn Lys Asp Ser Asp
    1010                1015                1020

Lys Leu Ser Pro Val Phe Thr Gln Ser Arg Pro Leu Pro Ser Ser
    1025                1030                1035

Asn Ile His Arg Pro Lys Pro Ser Arg Pro Thr Pro Gly Asn Thr
    1040                1045                1050

Ser Lys Gln Gly Asp Pro Ser Lys Asn Ser Met Thr Leu Asp Leu
    1055                1060                1065

Asn Ser Ser Ser Lys Cys Asp Asp Ser Phe Gly Leu Ser Ser Asn
    1070                1075                1080

Ser Ser Asn Cys Cys Tyr Thr Ser Asp Glu Thr Val Phe Thr Pro
```

-continued

```
            1085                1090                1095
Val Glu Glu Lys Cys Arg Leu Asp Val Asn Thr Glu Leu Asn Ser
        1100                1105                1110
Ser Ile Glu Asp Leu Leu Glu Ala Ser Met Pro Ser Ser Asp Thr
        1115                1120                1125
Thr Val Thr Phe Lys Ser Glu Val Ala Val Leu Ser Pro Glu Lys
        1130                1135                1140
Ala Glu Asn Asp Asp Thr Tyr Lys Asp Val Asn His Asn Gln
        1145                1150                1155
Lys Cys Lys Glu Lys Met Glu Ala Glu Glu Glu Ala Leu Ala
        1160                1165                1170
Ile Ala Met Ala Met Ser Ala Ser Gln Val Ala Leu Pro Ile Val
        1175                1180                1185
Pro Gln Leu Gln Val Glu Asn Gly Glu Asp Ile Ile Ile Ile Gln
        1190                1195                1200
Gln Asp Thr Pro Glu Thr Leu Pro Gly His Thr Lys Ala Lys Gln
        1205                1210                1215
Pro Tyr Arg Glu Asp Thr Glu Trp Leu Lys Gly Gln Gln Ile Gly
        1220                1225                1230
Leu Gly Ala Phe Ser Ser Cys Tyr Gln Ala Gln Asp Val Gly Thr
        1235                1240                1245
Gly Thr Leu Met Ala Val Lys Gln Val Thr Tyr Val Arg Asn Thr
        1250                1255                1260
Ser Ser Glu Gln Glu Glu Val Val Glu Ala Leu Arg Glu Glu Ile
        1265                1270                1275
Arg Met Met Ser His Leu Asn His Pro Asn Ile Ile Arg Met Leu
        1280                1285                1290
Gly Ala Thr Cys Glu Lys Ser Asn Tyr Asn Leu Phe Ile Glu Trp
        1295                1300                1305
Met Ala Gly Gly Ser Val Ala His Leu Leu Ser Lys Tyr Gly Ala
        1310                1315                1320
Phe Lys Glu Ser Val Val Ile Asn Tyr Thr Glu Gln Leu Leu Arg
        1325                1330                1335
Gly Leu Ser Tyr Leu His Glu Asn Gln Ile Ile His Arg Asp Val
        1340                1345                1350
Lys Gly Ala Asn Leu Leu Ile Asp Ser Thr Gly Gln Arg Leu Arg
        1355                1360                1365
Ile Ala Asp Phe Gly Ala Ala Ala Arg Leu Ala Ser Lys Gly Thr
        1370                1375                1380
Gly Ala Gly Glu Phe Gln Gly Gln Leu Leu Gly Thr Ile Ala Phe
        1385                1390                1395
Met Ala Pro Glu Val Leu Arg Gly Gln Gln Tyr Gly Arg Ser Cys
        1400                1405                1410
Asp Val Trp Ser Val Gly Cys Ala Ile Ile Glu Met Ala Cys Ala
        1415                1420                1425
Lys Pro Pro Trp Asn Ala Glu Lys His Ser Asn His Leu Ala Leu
        1430                1435                1440
Ile Phe Lys Ile Ala Ser Ala Thr Thr Ala Pro Ser Ile Pro Ser
        1445                1450                1455
His Leu Ser Pro Gly Leu Arg Asp Val Ala Leu Arg Cys Leu Glu
        1460                1465                1470
Leu Gln Pro Gln Asp Arg Pro Pro Ser Arg Glu Leu Leu Lys His
        1475                1480                1485
```

-continued

```
Pro Val Phe Arg Thr Thr Trp
    1490            1495

<210> SEQ ID NO 4
<211> LENGTH: 1492
<212> TYPE: PRT
<213> ORGANISM: rat MEKK1

<400> SEQUENCE: 4

Met Ala Ala Ala Gly Asp Arg Ala Ser Ser Gly Phe Pro Gly
1               5                   10                  15

Ala Ala Ala Ala Ser Pro Glu Ala Gly Gly Gly Gly Ala Leu Gln
                20                  25                  30

Gly Ser Gly Ala Pro Ala Ala Gly Ala Gly Leu Leu Arg Glu Thr Gly
            35                  40                  45

Ser Ala Gly Arg Glu Arg Ala Asp Trp Arg Arg Gln Gln Leu Arg Lys
50                  55                  60

Val Arg Ser Val Glu Leu Asp Gln Leu Pro Glu Gln Pro Leu Phe Leu
65                  70                  75                  80

Thr Ala Ser Pro Pro Cys Pro Ser Thr Ser Pro Ser Pro Glu Pro Ala
                85                  90                  95

Asp Ala Ala Ala Gly Ala Ser Gly Phe Gln Pro Ala Ala Gly Pro Pro
                100                 105                 110

Pro Pro Gly Ala Ala Ser Arg Cys Gly Ser His Ser Ala Glu Leu Ala
            115                 120                 125

Ala Ala Arg Asp Ser Gly Ala Arg Ser Pro Ala Gly Ala Glu Pro Pro
        130                 135                 140

Ser Ala Ala Ala Pro Ser Gly Arg Glu Met Glu Asn Lys Glu Thr Leu
145                 150                 155                 160

Lys Gly Leu His Lys Met Asp Asp Arg Pro Glu Glu Arg Met Ile Arg
                165                 170                 175

Glu Lys Leu Lys Ala Thr Cys Met Pro Ala Trp Lys His Glu Trp Leu
                180                 185                 190

Glu Arg Arg Asn Arg Arg Gly Pro Val Val Val Lys Pro Ile Pro Ile
            195                 200                 205

Lys Gly Asp Gly Ser Glu Met Ser Asn Leu Ala Ala Glu Leu Gln Gly
        210                 215                 220

Glu Gly Gln Ala Gly Ser Ala Ala Pro Ala Pro Lys Gly Arg Arg Ser
225                 230                 235                 240

Pro Ser Pro Gly Ser Ser Pro Ser Gly Arg Ser Gly Lys Pro Glu Ser
                245                 250                 255

Pro Gly Val Arg Arg Lys Arg Val Ser Pro Val Pro Phe Gln Ser Gly
                260                 265                 270

Arg Ile Thr Pro Pro Arg Arg Ala Pro Ser Pro Asp Gly Phe Ser Pro
            275                 280                 285

Ser Pro Glu Glu Thr Ser Arg Arg Val Asn Lys Val Met Arg Ala Arg
        290                 295                 300

Leu Tyr Leu Leu Gln Gln Ile Gly Pro Asn Ser Phe Leu Ile Gly Gly
305                 310                 315                 320

Asp Ser Pro Asp Asn Lys Tyr Arg Val Phe Ile Gly Pro Gln Asn Cys
                325                 330                 335

Ser Cys Gly Arg Gly Thr Phe Cys Ile His Leu Leu Phe Val Met Leu
                340                 345                 350

Arg Val Phe Gln Leu Glu Pro Ser Asp Pro Met Leu Trp Arg Lys Thr
```

-continued

```
                355                 360                 365
Leu Lys Asn Phe Glu Val Glu Ser Leu Phe Gln Lys Tyr His Ser Arg
    370                 375                 380
Arg Ser Ser Arg Ile Lys Ala Pro Ser Arg Asn Thr Ile Gln Lys Phe
385                 390                 395                 400
Val Ser Arg Met Ser Asn Cys His Thr Leu Ser Ser Ser Thr Ser
                405                 410                 415
Thr Ser Ser Ser Glu Asn Ser Ile Lys Asp Glu Glu Gln Met Cys
                420                 425                 430
Pro Ile Cys Leu Leu Gly Met Leu Asp Glu Glu Ser Leu Thr Val Cys
            435                 440                 445
Glu Asp Gly Cys Arg Asn Lys Leu His His Cys Met Ser Ile Trp
450                 455                 460
Ala Glu Glu Cys Arg Arg Asn Arg Glu Pro Leu Ile Cys Pro Leu Cys
465                 470                 475                 480
Arg Ser Lys Trp Arg Ser His Asp Phe Tyr Ser His Glu Leu Ser Ser
                485                 490                 495
Pro Val Asp Ser Pro Thr Ser Leu Arg Gly Val Gln Gln Pro Ser Ser
            500                 505                 510
Pro Gln Gln Pro Val Ala Gly Ser Gln Arg Asn Gln Glu Ser Asn
515                 520                 525
Phe Asn Leu Thr His Tyr Gly Thr Gln Gln Ile Pro Pro Ala Tyr Lys
    530                 535                 540
Asp Leu Ala Glu Pro Trp Ile Gln Ala Phe Gly Met Glu Leu Val Gly
545                 550                 555                 560
Cys Leu Phe Ser Arg Asn Trp Asn Val Arg Glu Met Ala Leu Arg Arg
                565                 570                 575
Leu Ser His Asp Val Ser Gly Ala Leu Leu Ala Asn Gly Glu Ser
            580                 585                 590
Thr Gly Thr Ser Gly Gly Gly Ser Gly Ser Leu Ser Ala Gly Ala
        595                 600                 605
Ala Ser Gly Ser Ser Gln Pro Ser Ile Ser Gly Asp Val Val Glu Ala
    610                 615                 620
Phe Cys Ser Val Leu Ser Ile Val Cys Ala Asp Pro Val Tyr Lys Val
625                 630                 635                 640
Tyr Val Ala Ala Leu Lys Thr Leu Arg Ala Met Leu Val Tyr Thr Pro
                645                 650                 655
Cys His Ser Leu Ala Glu Arg Ile Lys Leu Gln Arg Leu Leu Arg Pro
                660                 665                 670
Val Val Asp Thr Ile Leu Val Lys Cys Ala Asp Ala Asn Ser Arg Thr
            675                 680                 685
Ser Gln Leu Ser Ile Ser Thr Leu Leu Glu Leu Cys Lys Gly Gln Ala
    690                 695                 700
Gly Glu Leu Ala Val Gly Arg Glu Ile Leu Lys Ala Gly Ser Ile Gly
705                 710                 715                 720
Val Gly Gly Val Asp Tyr Val Leu Ser Cys Ile Leu Gly Asn Gln Ala
                725                 730                 735
Glu Ser Asn Asn Trp Gln Glu Leu Leu Gly Arg Leu Cys Leu Ile Asp
                740                 745                 750
Arg Leu Leu Leu Glu Ile Ser Ala Glu Phe Tyr Pro His Ile Val Ser
            755                 760                 765
Thr Asp Val Ser Gln Ala Glu Pro Val Glu Ile Arg Tyr Lys Lys Leu
770                 775                 780
```

-continued

```
Leu Ser Leu Leu Ala Phe Ala Leu Gln Ser Ile Asp Asn Ser His Ser
785                 790                 795                 800

Met Val Gly Lys Leu Ser Arg Arg Ile Tyr Leu Ser Ser Ala Arg Met
                805                 810                 815

Val Thr Thr Val Pro Pro Leu Phe Ser Lys Leu Val Thr Met Leu Ser
                820                 825                 830

Ala Ser Gly Ser Ser His Phe Ala Arg Met Arg Arg Arg Leu Met Ala
                835                 840                 845

Ile Ala Asp Glu Val Glu Ile Ala Glu Val Ile Gln Leu Gly Ser Glu
850                 855                 860

Asp Thr Leu Asp Gly Gln Gln Asp Ser Ser Gln Ala Leu Ala Pro Pro
865                 870                 875                 880

Arg Tyr Pro Glu Ser Ser Leu Glu His Thr Ala His Val Glu Lys
                885                 890                 895

Thr Gly Lys Gly Leu Lys Ala Thr Arg Leu Ser Ala Ser Ser Glu Asp
                900                 905                 910

Ile Ser Asp Arg Leu Ala Gly Val Ser Val Gly Leu Pro Ser Ser Ala
                915                 920                 925

Thr Thr Glu Gln Pro Lys Pro Thr Val Gln Thr Lys Gly Arg Pro His
930                 935                 940

Ser Gln Cys Leu Asn Ser Ser Pro Leu Ser Pro Pro Gln Leu Met Phe
945                 950                 955                 960

Pro Ala Ile Ser Ala Pro Cys Ser Ser Ala Pro Ser Val Pro Ala Gly
                965                 970                 975

Ser Val Thr Asp Ala Ser Lys His Arg Pro Arg Ala Phe Val Pro Cys
                980                 985                 990

Lys Ile Pro Ser Ala Ser Pro Gln Thr Gln Arg Lys Phe Ser Leu Gln
                995                 1000                1005

Phe Gln Arg Thr Cys Ser Glu Asn Arg Asp Ser Glu Lys Leu Ser
    1010                1015                1020

Pro Val Phe Thr Gln Ser Arg Pro Pro Pro Ser Asn Ile His
    1025                1030                1035

Arg Ala Lys Ala Ser Arg Pro Val Pro Gly Ser Thr Ser Lys Leu
    1040                1045                1050

Gly Asp Ala Ser Lys Asn Ser Met Thr Leu Asp Leu Asn Ser Ala
    1055                1060                1065

Ser Gln Cys Asp Asp Ser Phe Gly Ser Gly Ser Asn Ser Gly Ser
    1070                1075                1080

Ala Val Ile Pro Ser Glu Glu Thr Ala Phe Thr Pro Ala Glu Asp
    1085                1090                1095

Lys Cys Arg Leu Asp Val Asn Pro Glu Leu Asn Ser Ser Ile Glu
    1100                1105                1110

Asp Leu Leu Glu Ala Ser Met Pro Ser Ser Asp Thr Thr Val Thr
    1115                1120                1125

Phe Lys Ser Glu Val Ala Val Leu Ser Pro Glu Lys Ala Glu Ser
    1130                1135                1140

Asp Asp Thr Tyr Lys Asp Asp Val Asn His Asn Gln Lys Cys Lys
    1145                1150                1155

Glu Lys Met Glu Ala Glu Glu Glu Ala Leu Ala Ile Ala Met
    1160                1165                1170

Ala Met Ser Ala Ser Gln Asp Ala Leu Pro Ile Val Pro Gln Leu
    1175                1180                1185
```

-continued

```
Gln Val Glu Asn Gly Glu Asp Ile Ile Ile Ile Gln Gln Asp Thr
1190            1195                1200

Pro Glu Thr Leu Pro Gly His Thr Lys Ala Asn Glu Pro Tyr Arg
1205            1210                1215

Glu Asp Thr Glu Trp Leu Lys Gly Gln Gln Ile Gly Leu Gly Ala
1220            1225                1230

Phe Ser Ser Cys Tyr Gln Ala Gln Asp Val Gly Thr Gly Thr Leu
1235            1240                1245

Met Ala Val Lys Gln Val Thr Tyr Val Arg Asn Thr Ser Ser Glu
1250            1255                1260

Gln Glu Glu Val Val Glu Ala Leu Arg Glu Glu Ile Arg Met Met
1265            1270                1275

Ser His Leu Asn His Pro Asn Ile Ile Arg Met Leu Gly Ala Thr
1280            1285                1290

Cys Glu Lys Ser Asn Tyr Asn Leu Phe Ile Glu Trp Met Ala Gly
1295            1300                1305

Ala Ser Val Ala His Leu Leu Ser Lys Tyr Gly Ala Phe Lys Glu
1310            1315                1320

Ser Val Val Ile Asn Tyr Thr Glu Gln Leu Leu Arg Gly Leu Ser
1325            1330                1335

Tyr Leu His Glu Asn Gln Ile Ile His Arg Asp Val Lys Gly Ala
1340            1345                1350

Asn Leu Leu Ile Asp Ser Thr Gly Gln Arg Leu Arg Ile Ala Asp
1355            1360                1365

Phe Gly Ala Ala Ala Arg Leu Ala Ser Lys Gly Thr Gly Ala Gly
1370            1375                1380

Glu Phe Gln Gly Gln Leu Leu Gly Thr Ile Ala Phe Met Ala Pro
1385            1390                1395

Glu Val Leu Arg Gly Gln Gln Tyr Gly Arg Ser Cys Asp Val Trp
1400            1405                1410

Ser Val Gly Cys Ala Ile Ile Glu Met Ala Cys Ala Lys Pro Pro
1415            1420                1425

Trp Asn Ala Glu Lys His Ser Asn His Leu Ala Leu Ile Phe Lys
1430            1435                1440

Ile Ala Ser Ala Thr Thr Ala Pro Ser Ile Pro Ser His Leu Ser
1445            1450                1455

Pro Gly Leu Arg Asp Val Ala Leu Arg Cys Leu Glu Leu Gln Pro
1460            1465                1470

Gln Asp Arg Pro Pro Ser Arg Glu Leu Leu Lys His Pro Val Phe
1475            1480                1485

Arg Thr Thr Trp
1490

<210> SEQ ID NO 5
<211> LENGTH: 1492
<212> TYPE: PRT
<213> ORGANISM: mouse MEKK1

<400> SEQUENCE: 5

Met Ala Ala Ala Ala Gly Asp Arg Ala Ser Ser Ser Gly Phe Pro Gly
1               5                   10                  15

Ala Ala Ala Ala Ser Pro Glu Ala Gly Gly Gly Gly Gly Gly Gly
            20                  25                  30

Ala Leu Gln Gly Ser Gly Ala Pro Ala Ala Gly Ala Ala Gly Leu Leu
        35                  40                  45
```

```
Arg Glu Pro Gly Ser Ala Gly Arg Glu Arg Ala Asp Trp Arg Arg Arg
     50                  55                  60
Gln Leu Arg Lys Val Arg Ser Val Glu Leu Asp Gln Leu Pro Glu Gln
 65                  70                  75                  80
Pro Leu Phe Leu Ala Ala Ser Pro Pro Cys Pro Ser Thr Ser Pro
                 85                  90                  95
Ser Pro Glu Pro Ala Asp Ala Ala Gly Ala Ser Arg Phe Gln Pro
            100                 105                 110
Ala Ala Gly Pro Pro Pro Gly Ala Ala Ser Arg Cys Gly Ser His
        115                 120                 125
Ser Ala Glu Leu Ala Ala Arg Asp Ser Gly Ala Arg Ser Pro Ala
        130                 135                 140
Gly Ala Glu Pro Pro Ser Ala Ala Pro Ser Gly Arg Glu Met Glu
145                 150                 155                 160
Asn Lys Glu Thr Leu Lys Gly Leu His Lys Met Glu Asp Arg Pro Glu
                165                 170                 175
Glu Arg Met Ile Arg Glu Lys Leu Lys Ala Thr Cys Met Pro Ala Trp
            180                 185                 190
Lys His Glu Trp Leu Glu Arg Arg Asn Arg Arg Gly Pro Val Val Val
        195                 200                 205
Lys Pro Ile Pro Ile Lys Gly Asp Gly Ser Glu Val Asn Asn Leu Ala
210                 215                 220
Ala Glu Pro Gln Gly Glu Gly Gln Ala Gly Ser Ala Ala Pro Ala Pro
225                 230                 235                 240
Lys Gly Arg Arg Ser Pro Ser Pro Gly Ser Ser Pro Ser Gly Arg Ser
                245                 250                 255
Val Lys Pro Glu Ser Pro Gly Val Arg Arg Lys Arg Val Ser Pro Val
            260                 265                 270
Pro Phe Gln Ser Gly Arg Ile Thr Pro Pro Arg Arg Ala Pro Ser Pro
        275                 280                 285
Asp Gly Phe Ser Pro Tyr Ser Pro Glu Glu Thr Ser Arg Arg Val Asn
290                 295                 300
Lys Val Met Arg Ala Arg Leu Tyr Leu Leu Gln Gln Ile Gly Pro Asn
305                 310                 315                 320
Ser Phe Leu Ile Gly Gly Asp Ser Pro Asp Asn Lys Tyr Arg Val Phe
                325                 330                 335
Ile Gly Pro Gln Asn Cys Ser Cys Gly Arg Gly Ala Phe Cys Ile His
            340                 345                 350
Leu Leu Phe Val Met Leu Arg Val Phe Gln Leu Glu Pro Ser Asp Pro
        355                 360                 365
Met Leu Trp Arg Lys Thr Leu Lys Asn Phe Glu Val Glu Ser Leu Phe
    370                 375                 380
Gln Lys Tyr His Ser Arg Arg Ser Ser Arg Ile Lys Ala Pro Ser Arg
385                 390                 395                 400
Asn Thr Ile Gln Lys Phe Val Ser Arg Met Ser Asn Ser His Thr Leu
                405                 410                 415
Ser Ser Ser Ser Thr Ser Thr Ser Ser Ser Glu Asn Ser Ile Lys Asp
            420                 425                 430
Glu Glu Glu Gln Met Cys Pro Ile Cys Leu Leu Gly Met Leu Asp Glu
        435                 440                 445
Glu Ser Leu Thr Val Cys Glu Asp Gly Cys Arg Asn Lys Leu His His
450                 455                 460
```

```
His Cys Met Ser Ile Trp Ala Glu Glu Cys Arg Arg Asn Arg Glu Pro
465                 470                 475                 480

Leu Ile Cys Pro Leu Cys Arg Ser Trp Arg Ser His Asp Phe Tyr Ser
                485                 490                 495

His Glu Leu Ser Ser Pro Val Glu Ser Pro Ala Ser Leu Arg Ala Val
            500                 505                 510

Gln Gln Pro Ser Ser Pro Gln Gln Pro Val Ala Gly Ser Gln Arg Arg
        515                 520                 525

Asn Gln Glu Ser Ser Phe Asn Leu Thr His Phe Gly Thr Gln Gln Ile
    530                 535                 540

Pro Ser Ala Tyr Lys Asp Leu Ala Glu Pro Trp Ile Gln Val Phe Gly
545                 550                 555                 560

Met Glu Leu Val Gly Cys Leu Phe Ser Arg Asn Trp Asn Val Arg Glu
                565                 570                 575

Met Ala Leu Arg Arg Leu Ser His Asp Val Ser Gly Ala Leu Leu Leu
                580                 585                 590

Ala Asn Gly Glu Ser Thr Gly Asn Ser Gly Gly Ser Gly Gly Ser
        595                 600                 605

Leu Ser Ala Gly Ala Ala Ser Gly Ser Ser Gln Pro Ser Ile Ser Gly
    610                 615                 620

Asp Val Glu Ala Cys Cys Ser Val Leu Ser Ile Val Cys Ala Asp
625                 630                 635                 640

Pro Val Tyr Lys Val Tyr Val Ala Ala Leu Lys Thr Leu Arg Ala Met
                645                 650                 655

Leu Val Tyr Thr Pro Cys His Ser Leu Ala Glu Arg Ile Lys Leu Gln
                660                 665                 670

Arg Leu Leu Arg Pro Val Val Asp Thr Ile Leu Val Lys Cys Ala Asp
            675                 680                 685

Ala Asn Ser Arg Thr Ser Gln Leu Ser Ile Ser Thr Val Leu Glu Leu
    690                 695                 700

Cys Lys Gly Gln Ala Gly Glu Leu Ala Val Gly Arg Glu Ile Leu Lys
705                 710                 715                 720

Ala Gly Ser Ile Gly Val Gly Val Asp Tyr Val Leu Ser Cys Ile
                725                 730                 735

Leu Gly Asn Gln Ala Glu Ser Asn Asn Trp Gln Glu Leu Leu Gly Arg
            740                 745                 750

Leu Cys Leu Ile Asp Arg Leu Leu Glu Phe Pro Ala Glu Phe Tyr
            755                 760                 765

Pro His Ile Val Ser Thr Asp Val Ser Gln Ala Glu Pro Val Glu Ile
    770                 775                 780

Arg Tyr Lys Lys Leu Leu Ser Leu Leu Thr Phe Ala Leu Gln Ser Ile
785                 790                 795                 800

Asp Asn Ser His Ser Met Val Gly Lys Leu Ser Arg Arg Ile Tyr Leu
                805                 810                 815

Ser Ser Ala Arg Met Val Thr Ala Val Pro Ala Val Phe Ser Lys Leu
            820                 825                 830

Val Thr Met Leu Asn Ala Ser Gly Ser Thr His Phe Thr Arg Met Arg
        835                 840                 845

Arg Arg Leu Met Ala Ile Ala Asp Glu Val Glu Ile Ala Glu Val Ile
        850                 855                 860

Gln Leu Gly Val Glu Asp Thr Val Asp Gly His Gln Asp Ser Leu Gln
865                 870                 875                 880

Ala Val Ala Pro Thr Ser Cys Leu Glu Asn Ser Ser Leu Glu His Thr
```

-continued

```
                885                 890                 895
Val His Arg Glu Lys Thr Gly Lys Gly Leu Ser Ala Thr Arg Leu Ser
                900                 905                 910
Ala Ser Ser Glu Asp Ile Ser Asp Arg Leu Ala Gly Val Ser Val Gly
                915                 920                 925
Leu Pro Ser Ser Thr Thr Thr Glu Gln Pro Lys Pro Ala Val Gln Thr
            930                 935                 940
Lys Gly Arg Pro His Ser Gln Cys Leu Asn Ser Ser Pro Leu Ser His
945                 950                 955                 960
Ala Gln Leu Met Phe Pro Ala Pro Ser Ala Pro Cys Ser Ser Ala Pro
                965                 970                 975
Ser Val Pro Asp Ile Ser Lys His Arg Pro Gln Ala Phe Val Pro Cys
                980                 985                 990
Lys Ile Pro Ser Ala Ser Pro Gln Thr Gln Arg Lys Phe Ser Leu Gln
            995                 1000                1005
Phe Gln Arg Asn Cys Ser Glu His Arg Asp Ser Asp Gln Leu Ser
        1010                1015                1020
Pro Val Phe Thr Gln Ser Arg Pro Pro Ser Ser Asn Ile His
        1025                1030                1035
Arg Pro Lys Pro Ser Arg Pro Val Pro Gly Ser Thr Ser Lys Leu
        1040                1045                1050
Gly Asp Ala Thr Lys Ser Ser Met Thr Leu Asp Leu Gly Ser Ala
        1055                1060                1065
Ser Arg Cys Asp Asp Ser Phe Gly Gly Gly Gly Asn Ser Gly Asn
        1070                1075                1080
Ala Val Ile Pro Ser Asp Glu Thr Val Phe Thr Pro Val Glu Asp
        1085                1090                1095
Lys Cys Arg Leu Asp Val Asn Thr Glu Leu Asn Ser Ser Ile Glu
        1100                1105                1110
Asp Leu Leu Glu Ala Ser Met Pro Ser Ser Asp Thr Thr Val Thr
        1115                1120                1125
Phe Lys Ser Glu Val Ala Val Leu Ser Pro Glu Lys Ala Glu Asn
        1130                1135                1140
Asp Asp Thr Tyr Lys Asp Asp Val Asn His Asn Gln Lys Cys Lys
        1145                1150                1155
Glu Lys Met Glu Ala Glu Glu Glu Ala Leu Ala Ile Ala Met
        1160                1165                1170
Ala Met Ser Ala Ser Gln Asp Ala Leu Pro Ile Val Pro Gln Leu
        1175                1180                1185
Gln Val Glu Asn Gly Glu Asp Ile Ile Ile Ile Gln Gln Asp Thr
        1190                1195                1200
Pro Glu Thr Leu Pro Gly His Thr Lys Ala Lys Gln Pro Tyr Arg
        1205                1210                1215
Glu Asp Ala Glu Trp Leu Lys Gly Gln Gln Ile Gly Leu Gly Ala
        1220                1225                1230
Phe Ser Ser Cys Tyr Gln Ala Gln Asp Val Gly Thr Gly Thr Leu
        1235                1240                1245
Met Ala Val Lys Gln Val Thr Tyr Val Arg Asn Thr Ser Ser Glu
        1250                1255                1260
Gln Glu Glu Val Val Glu Ala Leu Arg Glu Glu Ile Arg Met Met
        1265                1270                1275
Gly His Leu Asn His Pro Asn Ile Ile Arg Met Leu Gly Ala Thr
        1280                1285                1290
```

```
Cys Glu Lys Ser Asn Tyr Asn Leu Phe Ile Glu Trp Met Ala Gly
    1295                1300                1305

Gly Ser Val Ala His Leu Leu Ser Lys Tyr Gly Ala Phe Lys Glu
    1310                1315                1320

Ser Val Val Ile Asn Tyr Thr Glu Gln Leu Leu Arg Gly Leu Ser
    1325                1330                1335

Tyr Leu His Glu Asn Gln Ile Ile His Arg Asp Val Lys Gly Ala
    1340                1345                1350

Asn Leu Leu Ile Asp Ser Thr Gly Gln Arg Leu Arg Ile Ala Asp
    1355                1360                1365

Phe Gly Ala Ala Ala Arg Leu Ala Ser Lys Gly Thr Gly Ala Gly
    1370                1375                1380

Glu Phe Gln Gly Gln Leu Leu Gly Thr Ile Ala Phe Met Ala Pro
    1385                1390                1395

Glu Val Leu Arg Gly Gln Gln Tyr Gly Arg Ser Cys Asp Val Trp
    1400                1405                1410

Ser Val Gly Cys Ala Ile Ile Glu Met Ala Cys Ala Lys Pro Pro
    1415                1420                1425

Trp Asn Ala Glu Lys His Ser Asn His Leu Ala Leu Ile Phe Lys
    1430                1435                1440

Ile Ala Ser Ala Thr Thr Ala Pro Ser Ile Pro Ser His Leu Ser
    1445                1450                1455

Pro Gly Leu Arg Asp Val Ala Val Arg Cys Leu Glu Leu Gln Pro
    1460                1465                1470

Gln Asp Arg Pro Pro Ser Arg Glu Leu Leu Lys His Pro Val Phe
    1475                1480                1485

Arg Thr Thr Trp
    1490

<210> SEQ ID NO 6
<211> LENGTH: 55
<212> TYPE: DNA
<213> ORGANISM: Human

<400> SEQUENCE: 6
atggcggcgg cggcggggaa tcgcgcctcg tcgggattcc cgggcgccag ggcta      55

<210> SEQ ID NO 7
<211> LENGTH: 61
<212> TYPE: DNA
<213> ORGANISM: Human

<400> SEQUENCE: 7
gagaaaatgg cggcggcggc ggggaatcgc gcctcgtcgg gattcccggg cgccagggct    60
a                                                                    61

<210> SEQ ID NO 8
<211> LENGTH: 11
<212> TYPE: DNA
<213> ORGANISM: Human

<400> SEQUENCE: 8
gcgcgcccgc g                                                         11

<210> SEQ ID NO 9
<211> LENGTH: 17
<212> TYPE: DNA
```

-continued

```
<213> ORGANISM: Human

<400> SEQUENCE: 9
ccgcgagccg cggcggc                                                  17

<210> SEQ ID NO 10
<211> LENGTH: 12
<212> TYPE: DNA
<213> ORGANISM: Human

<400> SEQUENCE: 10
tttggatggt ca                                                       12

<210> SEQ ID NO 11
<211> LENGTH: 10
<212> TYPE: DNA
<213> ORGANISM: Human

<400> SEQUENCE: 11
ggacagcttc                                                          10

<210> SEQ ID NO 12
<211> LENGTH: 11
<212> TYPE: DNA
<213> ORGANISM: Human

<400> SEQUENCE: 12
cccctgagtg c                                                        11

<210> SEQ ID NO 13
<211> LENGTH: 10
<212> TYPE: DNA
<213> ORGANISM: Human

<400> SEQUENCE: 13
gccagcattt                                                          10

<210> SEQ ID NO 14
<211> LENGTH: 11
<212> TYPE: DNA
<213> ORGANISM: Human

<400> SEQUENCE: 14
catctagacc t                                                        11

<210> SEQ ID NO 15
<211> LENGTH: 10
<212> TYPE: DNA
<213> ORGANISM: Human

<400> SEQUENCE: 15
ggctgtagca                                                          10

<210> SEQ ID NO 16
<211> LENGTH: 10
<212> TYPE: DNA
<213> ORGANISM: Human

<400> SEQUENCE: 16
gtaatgctgt                                                          10

<210> SEQ ID NO 17
<211> LENGTH: 15
```

```
<212> TYPE: DNA
<213> ORGANISM: Human

<400> SEQUENCE: 17
ggatgccctc cccat                                                    15

<210> SEQ ID NO 18
<211> LENGTH: 20
<212> TYPE: PRT
<213> ORGANISM: Human

<400> SEQUENCE: 18

Met Ala Ala Ala Ala Gly Asn Arg Ala Ser Ser Ser Gly Phe Pro Gly
1               5                   10                  15

Ala Arg Ala Thr
            20

<210> SEQ ID NO 19
<211> LENGTH: 22
<212> TYPE: PRT
<213> ORGANISM: Human

<400> SEQUENCE: 19

Glu Lys Met Ala Ala Ala Ala Gly Asn Arg Ala Ser Ser Ser Gly Phe
1               5                   10                  15

Pro Gly Ala Arg Ala Thr
            20

<210> SEQ ID NO 20
<211> LENGTH: 5
<212> TYPE: PRT
<213> ORGANISM: Human

<400> SEQUENCE: 20

Ser Ala Pro Ala Ala
1               5

<210> SEQ ID NO 21
<211> LENGTH: 5
<212> TYPE: PRT
<213> ORGANISM: Human

<400> SEQUENCE: 21

Ala Ser Arg Gly Gly
1               5

<210> SEQ ID NO 22
<211> LENGTH: 5
<212> TYPE: PRT
<213> ORGANISM: Human

<400> SEQUENCE: 22

Cys Ala Arg Gly Thr
1               5

<210> SEQ ID NO 23
<211> LENGTH: 6
<212> TYPE: PRT
<213> ORGANISM: Human

<400> SEQUENCE: 23

Val Ser Ser Ser Thr His
1               5
```

```
<210> SEQ ID NO 24
<211> LENGTH: 7
<212> TYPE: PRT
<213> ORGANISM: Human

<400> SEQUENCE: 24

Leu Met Ala Ile Ala Asp Glu
1               5

<210> SEQ ID NO 25
<211> LENGTH: 30
<212> TYPE: PRT
<213> ORGANISM: Human

<400> SEQUENCE: 25

Thr Leu Asp Gly Gln Gln Asp Ser Phe Leu Gln Ala Ser Val Pro Asn
1               5                   10                  15

Asn Tyr Leu Glu Thr Thr Glu Asn Ser Ser Pro Glu Cys Thr
            20                  25                  30

<210> SEQ ID NO 26
<211> LENGTH: 6
<212> TYPE: PRT
<213> ORGANISM: Human

<400> SEQUENCE: 26

Leu Ala Ser Ile Ser Val
1               5

<210> SEQ ID NO 27
<211> LENGTH: 17
<212> TYPE: PRT
<213> ORGANISM: Human

<400> SEQUENCE: 27

Ser Phe Gly Cys Ser Ser Asn Ser Ser Asn Ala Val Ile Pro Ser Asp
1               5                   10                  15

Glu

<210> SEQ ID NO 28
<211> LENGTH: 44
<212> TYPE: PRT
<213> ORGANISM: Human

<400> SEQUENCE: 28

Ser Gln Asp Ala Leu Pro Ile Val Pro Gln Leu Gln Val Glu Asn Gly
1               5                   10                  15

Glu Asp Ile Ile Ile Ile Gln Gln Asp Thr Pro Glu Thr Leu Pro Gly
            20                  25                  30

His Thr Lys Ala Lys Gln Pro Tyr Arg Glu Asp Thr
        35                  40
```